(12) United States Patent
Brotherton-Pleiss et al.

(10) Patent No.: US 8,153,809 B2
(45) Date of Patent: Apr. 10, 2012

(54) DIHYDROPYRIDONE UREAS AS P2X₇ MODULATORS

(75) Inventors: Christine E. Brotherton-Pleiss, Sunnyvale, CA (US); Joan Marie Caroon, Mountain View, CA (US); Francisco Javier Lopez-Tapia, Mahwah, NJ (US); Dov Nitzan, San Jose, CA (US); Keith Adrian Murray Walker, Los Altos Hills, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 304 days.

(21) Appl. No.: 12/637,903

(22) Filed: Dec. 15, 2009

(65) Prior Publication Data
US 2010/0160388 A1    Jun. 24, 2010

Related U.S. Application Data

(60) Provisional application No. 61/203,467, filed on Dec. 23, 2008.

(51) Int. Cl.
C07D 213/62    (2006.01)
A61K 31/44    (2006.01)

(52) U.S. Cl. ........................................ 546/298; 514/345
(58) Field of Classification Search .................. None
See application file for complete search history.

(56) References Cited

U.S. PATENT DOCUMENTS 5,399,566 A    3/1995  Katano et al.

FOREIGN PATENT DOCUMENTS

| EP | 0557843 A2 | 2/1993 |
|---|---|---|
| EP | 0569795 B1 | 4/1995 |
| EP | 0556738 B1 | 5/1995 |
| WO | 9929661 A1 | 7/1999 |
| WO | 9937304 A1 | 7/1999 |
| WO | 0196308 A1 | 12/2001 |
| WO | 03047577 A2 | 6/2003 |
| WO | 03059871 A1 | 7/2003 |
| WO | 2005082890 A1 | 9/2005 |
| WO | 2006025783 A1 | 3/2006 |
| WO | 2006056696 A2 | 6/2006 |
| WO | 2006107859 A2 | 10/2006 |
| WO | 2006109876 A1 | 10/2006 |
| WO | 2007035428 A1 | 3/2007 |
| WO | 2008104472 A1 | 9/2008 |

OTHER PUBLICATIONS

Hoffmann-Emery, F., et. al. "Efficient Synthesis of Novel NK1 Receptor Antagonists: Selective 1,4-Addition of Grignard Reagents to 6-Chloronicotinic Acid Derivatives," Journal of Organic Chemistry, 2006, vol. 71 (5) pp. 2000-2008.

Goodman, K.B., et. al. "Development of Dihydropyridone Indazole Amides as Selective Rho-Kinase Inhibitors," Journal of Medicinal Chemistry, 2007, vol. 50, pp. 6-9.

*Primary Examiner* — Janet Andres
*Assistant Examiner* — Heidi Reese
(74) *Attorney, Agent, or Firm* — Robert C. Hall

(57) ABSTRACT

Compounds of the formula I:

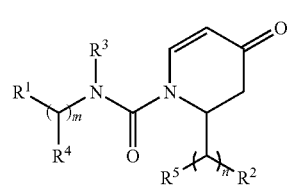

or pharmaceutically acceptable salts thereof, wherein m, n, $R^1$, $R^2$, $R^3$, $R^4$ and $R^5$ are as defined herein. Also disclosed are methods of making the compounds and using the compounds for treatment of diseases associated with the P2X7 purinergic receptor.

30 Claims, No Drawings

DIHYDROPYRIDONE UREAS AS P2X$_7$ MODULATORS

CROSS REFERENCE TO RELATED APPLICATIONS

This application is entitled to the benefit of U.S. Provisional Application Ser. No. 61/203,467, filed Dec. 23, 2008, the disclosure of which is incorporated herein by reference.

FIELD OF THE INVENTION

This invention pertains to compounds useful for treatment of diseases associated with P2X purinergic receptors, and more particularly to P2X$_7$ modulators usable for treatment of autoimmune and inflammatory diseases.

BACKGROUND OF THE INVENTION

P2X purinergic receptors are ATP-activated ionotropic receptors having seven subtypes. The P2X7 receptor subtype (also known as the P2Z receptor) is a ligand-gated ion channel found on mast cells, peripheral macrophages, lymphocytes, erythrocytes, fibroblasts and epidermal langerhans cells. Activation of P2X7 receptor on such immune system cells results in release of interleukin-1 beta. (Solle et al., *J. Biol. Chemistry* 276, 125-132, (2001)). The P2X7 receptor is also found on microglia, Schwann cells and astrocytes within the central nervous system (Donnelly-Roberts et al., *Br. J. Pharmacol.* 151, 571-579 (2007)).

Antagonists of P2X7 have been showed to block P2×7-mediated IL-1 beta release and P2×7-mediated cation flux (Stokes et al., *Br. J. Pharmacol.* 149, 880-887 (2006)). Mice lacking the P2X7 receptor show a lack of inflammatory and neuropathic hypersensitivity to mechanical and thermal stimuli (Chessell et al., *Pain* 114, 386-396 (2005)). P2X7 is thus believed to have a role in inflammatory responses (Ferrari et al., *J. Immunol.* 176, 3877-3883 (2006)) and in the onset and persistence of chronic pain (Honore et al., *J. Pharmacol. Ex. Ther.* 319, 1376-1385 (2006b)).

Modulators of the P2X7 receptor thus may have utility in the treatment of disease states such as rheumatoid arthritis, osteoarthritis, psoriasis, allergic dermatitis, asthma, chronic obstructive pulmonary disease, airways hyper-responsiveness, septic shock, glomerulonephritis, irritable bowel disease, diabetes, and Crohn's disease. P2X7 modulators may also be useful for treatment of pain, including chronic pain, neuropathic pain, and pain associated inflammatory processes and degenerative conditions.

There is accordingly a need for compounds that act as modulators of P2X receptors, including antagonists of P2X$_7$ receptor, as well as a need for methods of treating diseases, conditions and disorders mediated by P2X$_7$ The present invention satisfies these needs as well as others.

SUMMARY OF THE INVENTION

The invention provides compounds of the formula I:

I:

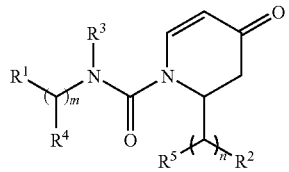

or pharmaceutically acceptable salts thereof, wherein:
m is 0 or 1;
n is 0 or 1;
R$^1$ is:
optionally substituted aryl;
optionally substituted heteroaryl;
C$_{1-6}$alkyl; or
adamantyl;
R$^2$ is:
optionally substituted aryl;
optionally substituted heteroaryl;
C$_{3-6}$cycloalkyl; or
C$_{3-6}$ branched alkyl; and
R$^3$, R$^4$ and R$^5$ each independently is:
hydrogen; or
C$_{1-6}$alkyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. C$_1$-C$_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula R$^a$—O—R$^b$—, where R$^a$ is alkyl and R$^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Alkylaminoalkoxy" means a group of the formula —O—R—NHR' wherein R is alkylene and R' is alkyl as defined herein.

"Alkylsulfonyl" means a moiety of the formula —$SO_2$—R, wherein R is alkyl as defined herein.

"Alkylsulfonylalkyl" means a moiety of the formula —R'—$SO_2$—R" where where R' is alkylene and R" is alkyl as defined herein.

"Alkylsulfonylalkoxy" means a group of the formula —O—R—$SO_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Preferred cycloalkyl are unsubstituted or substituted with alkyl. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Heteroalkyl" means an alkyl radical as defined herein wherein one, two or three hydrogen atoms have been replaced with a substituent independently selected from the group consisting of –$OR^a$, —$NR^bR^c$ and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, amino sulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

"Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, halo alkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Arthritis" means diseases or conditions damage to joints of the body and pain associated with such joint damage. Arthritis includes rheumatoid arthritis, osteoarthritis, psoriatic arthritis, septic arthritis and gouty arthritis.

"Pain" includes, without limitation, inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes.

All patents and publications identified herein are incorporated herein by reference in their entirety.

Compounds of the Invention

The invention provides compounds of the formula I:

or pharmaceutically acceptable salts thereof,
wherein:
m is 0 or 1;
n is 0 or 1;
$R^1$ is:
optionally substituted aryl;
optionally substituted heteroaryl; or
adamantyl;
$R^2$ is:
optionally substituted aryl;
optionally substituted heteroaryl;
$C_{3-6}$cycloalkyl;
$C_{1-6}$alkyl; or
$C_{3-6}$ branched alkyl; and
$R^3$ is:
hydrogen;
$C_{1-6}$alkyl;
alkylcarbonylalkyl; or
alkoxycarbonylalkyl;

$R^4$ and $R^5$ each independently is:
hydrogen; or
$C_{1-6}$alkyl.

In certain embodiments of formula I, $R^3$, $R^4$ and $R^5$ are hydrogen.

In certain embodiments of formula I, m is 0.
In certain embodiments of formula I, n is 0.
In certain embodiments of formula I, $R^3$ is hydrogen.
In certain embodiments of formula I, $R^4$ is hydrogen.
In certain embodiments of formula I, $R^5$ is hydrogen.
In certain embodiments of formula I, $R^1$ is optionally substituted aryl.
In certain embodiments of formula I, $R^1$ is optionally substituted phenyl.
In certain embodiments of formula I, $R^1$ is phenyl optionally substituted one, two, three or four times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfonyl-$C_{1-6}$alkoxy; hydroxy-$C_{1-6}$alkyl; $C_{3-6}$cycloalkyl-$C_{1-6}$alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonylC$_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$alkyl; or nitro; or two adjacent substituents may form a $C_{1-2}$alkylenedioxy or halo-$C_{1-2}$alkylenedioxy.

In certain embodiments of formula I, $R^1$ is phenyl substituted one, two, three or four times with a substituent or substituents each independently selected from: fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; or two adjacent substituents may form methylenedioxy, ethylenedioxy or difluoromethylenedioxy.

In certain embodiments of formula I, $R^1$ is phenyl substituted one, two, three or four times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; $C_{1-6}$alkoxy-$C_{1-6}$alkoxy; hydroxy-$C_{1-6}$alkoxy; $C_{1-6}$alkylsulfonyl-$C_{1-6}$alkoxy; hydroxy-$C_{1-6}$alkyl; hydroxy-$C_{1-6}$alkylamino; $C_{1-2}$alkylenedioxy; or $C_{3-6}$cycloalkyl-$C_{1-6}$alkoxy.

In certain embodiments of formula I, $R^1$ is phenyl substituted one, two, three or four times with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; or ethylenedioxy.

In certain embodiments of formula I, $R^1$ is phenyl substituted two or three times with substituents each independently selected from: fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of formula I, $R^1$ is phenyl substituted two or three times with substituents each independently selected from: fluoro; chloro; bromo; methyl; and methoxy.

In certain embodiments of formula I, $R^1$ is phenyl optionally substituted one, two or three times with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2,4-dichloro-5-methoxy-phenyl; 2-bromo-5-methoxy-4-trifluoromethyl-phenyl; 2-bromo-4,5-dichloro-phenyl; 2-bromo-4-chloro-5-iodo-phenyl; 2-bromo-4-chloro-5-trifluoromethyl-phenyl; 2-bromo-5-methoxy-4-methyl-phenyl; 2-isopropyl-4,5-dimethoxy-phenyl; 2-bromo-4-chloro-5-methanesulfanyl-phenyl; 2-bromo-4-chloro-5-methanesulfonyl-phenyl; 2-bromo-4-chloro-5-methanesulfinyl-phenyl; 2-bromo-4-chloro-5-fluoro-phenyl; 2-bromo-5-methoxy-phenyl; 2-bromo-5-methoxy-4-methoxycarbonyl-phenyl; 2-bromo-4-chloro-5-hydroxy-phenyl; 2-bromo-4-chloro-5-(methylamino-carbonyl-methyoxy)-phenyl; 2-methyl-4,5-dimethoxy-phenyl; 2-bromo-4-chloro-5-methoxycarbonyl-phenyl; 2-bromo-4-methanesulfonyl-5-methoxy-phenyl; 2-bromo-4-methyl-5-methoxy-phenyl; 2-bromo-4-chloro-5-(methoxycarbonyl-methoxy)-phenyl; 2-bromo-4-chloro-5-(hydroxycarbonyl-methoxy)-phenyl; 2-bromo-4-chloro-5-(2-methoxyethoxy)-phenyl; 4,5-dimethoxy-phenyl; 2-fluoro-4-chloro-5-methoxy-phenyl; 2-bromo-4-methoxycarbonyl-5-methoxy-phenyl; 6-bromo-benzo[1,3]dioxol-5-yl; 2-bromo-4-chloro-5-(2-hydroxyethoxy)-phenyl; 2-bromo-4-difluoromethoxy-5-methoxy-phenyl; 5-methoxy-4-methyl-phenyl; 2-bromo-4-chloro-5-(2-methylamino-ethoxy)-phenyl; 2-bromo-4-cyano-5-methyl-phenyl; 2-fluoro-4-methyl-5-methoxy-phenyl; 2-bromo-4-chloro-5-acetyl-phenyl; 5-methoxy-2-methyl-phenyl; 2-bromo-4-chloro-5-(3-methanesulfonyl-propoxy)-phenyl; 2-bromo-5-methoxy-4-(tert-butoxycarbonyl)-phenyl; 5-methanesulfonyl-2-methoxy-phenyl; 2-bromo-4-chloro-5-(1-hydroxyethyl)-phenyl; 2-fluoro-5-(2-hydroxyethoxy)-4-methyl-phenyl; 2-bromo-5-methoxy-4-amino carbonyl-phenyl; 6-bromo-2,2-difluoro-benzo[1,3]dioxol-5-yl; 2,6-difluoro-phenyl; 2-bromo-4-cyano-5-methoxy-phenyl; 2,5-dimethoxy-phenyl; 3-methoxycarbonyl-2-methyl-phenyl; 3-methoxy-phenyl; 4-methoxy-phenyl; 2,4-dimethoxy-phenyl; 4-chloro-5-methoxy-phenyl; 4-fluoro-5-methoxy-phenyl; 2-bromo-4-methyl-5-(tert-butoxycarbonyl)-phenyl; 3,4,5-trimethoxy-phenyl; 2-bromo-4,6-difluoro-phenyl; 2-ethyl-4,5-dimethoxy-phenyl; 2-bromo-4-methoxy-phenyl; 4-chloro-5-(2-hydroxyethoxy)-2-methyl-phenyl; 3-methoxycarbonyl-2-methyl-phenyl; 2,5-dimethyl-phenyl; 2-bromo-5-methoxy-phenyl; 2,3-dimethyl-phenyl; 2-bromo-4-chloro-5-hydroxymethyl-phenyl; 2-bromo-3,5-dimethyl-phenyl; 4-methoxy-2-methyl-phenyl; 2,4-dimethyl-phenyl; 2-iodo-4,5-dimethoxy-phenyl; 2-chloro-4,5-dimethoxy-phenyl; 7-bromo-2,3-dihydrobenzo[1,4]dioxin-6-yl; 4,5-dimethoxy-2-trifluoromethyl-phenyl; 2-bromo-5-ethoxy-4-methoxy-phenyl; 2-bromo-4-ethoxy-5-methoxy-phenyl; 2-bromo-5-cyclopropylmethoxy-4-methoxy-phenyl; 2-bromo-4-cyclopropylmethoxy-5-methoxy-phenyl; 2-cyano-4,5-dimethoxyphenyl; 2-bromo-5-difluoromethoxy-4-methoxy-phenyl; 2-bromo-4,5-bis-difluoromethoxy-phenyl; 2-bromo-4-fluoro-5-(2-methoxyethoxy)-phenyl; 2-bromo-4-fluoro-5-(2-hydroxyethoxy)-phenyl; 4-fluoro-4,5-dimethoxy-phenyl; 2,4-dimethylphenyl; 3,5-dimethylphenyl; 4,5-dimethoxy-2-morpholin-4-yl-phenyl; 3-methoxy-2-methyl-phenyl; 2,3-dimethoxy-phenyl; 4-fluoro-5-(2-hydroxy-ethoxy)-2-methyl-phenyl; 4-chloro-4-(3-hydroxypropyl)-2-methyl-phenyl; 2-dimethylamino-4,5-dimethoxyphenyl; 4-chloro-5-hydroxymethyl-2-methyl-phenyl; 2-bromo-4-trifluoromethoxy-phenyl; 2-bromo-4-chloro-5-dimethylaminocarbonylmethoxy-phenyl; 4-chloro-5-{[(2-methoxy-ethyl)-methyl-amino]-methyl}-2-methyl-phenyl; 5-(tert-butoxycarbonylaminomethyl)-2-methyl-4-chlorophenyl; 5-aminomethyl-4-chloro-2-methyl-phenyl; 4-chloro-2-methyl-5-(methylcarbonylaminomethyl)-phenyl; 5-{[bis-(2-hydroxy-ethyl)-amino]-methyl}-4-chloro-2-methyl-phenyl; 4-chloro-2-methyl-5-morpholin-4-ylmethyl-phenyl; 3-methyl-phenyl; 4-chloro-5-(2-hydroxy-ethyl)-2-methyl-phenyl; 2-bromo-3,4-ethylenedioxy-phenyl (7-bromo-2,3-dihydro-benzo[1,4]dioxin-6-yl)); 3-chloro-2-methyl-phenyl; 3-hydroxymethyl-2-methyl-phenyl; 2-methyl-3-methylaminocarbonyl-phenyl; 4-chloro-2-methyl-5-(piperidin-4-yloxy)-phenyl; 2-methyl-3-(tert-butoxycarbonylmethyl)-phenyl; 3-(2-hydroxy-ethyl)-2-methyl-phenyl; 4,5-difluoro-2-methyl-phenyl; 2-bromo-4,5-difluoro-phenyl; 3,4-dimethyl-phenyl; 2-chloro-3-methyl-phenyl; 2-bromo-4-(2-hydroxy-ethyl)-phenyl; 2-bromo-4-isopropyl-phenyl; 3-fluoro-2-methyl-phenyl; 2-bromo-5-(2-hydroxy-ethoxy)-4-methyl-phenyl; 2-(2-hydroxy-ethyl)-4,5-dimethoxy-phenyl; 4-chloro-5-dimethylaminomethyl-2-methyl-phenyl; 2-ethyl-phenyl; 2-propyl-phenyl; 5-methoxy-2,3-dimethyl-phenyl; and 3-(hydroxycarbonylmethyl)-2-methyl-phenyl.

In certain embodiments of formula I, $R^1$ is: 2-bromo-4,5-dimethoxy-phenyl; 2-bromo-4-chloro-5-methoxy-phenyl; 2-bromo-4-fluoro-5-methoxy-phenyl; 2,4-dichloro-5-methoxy-phenyl; 2-bromo-5-methoxy-4-trifluoromethyl-phenyl; 2-bromo-4,5-dichloro-phenyl; 2-bromo-4-chloro-5-iodo-phenyl; 2-bromo-4-chloro-5-trifluoromethyl-phenyl; 2-bromo-5-methoxy-4-methyl-phenyl; 2-isopropyl-4,5-dimethoxy-phenyl; 2-bromo-4-chloro-5-methanesulfanyl-phenyl; 2-bromo-4-chloro-5-methanesulfonyl-phenyl; 2-bromo-4-chloro-5-methanesulfinyl-phenyl; 2-bromo-4-chloro-5-fluoro-phenyl; 2-bromo-5-methoxy-phenyl; 2-bromo-5-methoxy-4-methoxycarbonyl-phenyl; 2-bromo-4-chloro-5-hydroxy-phenyl; 2-bromo-4-chloro-5-(methylamino-carbonyl-methyoxy)-phenyl; 2-methyl-4,5-dimethoxy-phenyl; 2-bromo-4-chloro-5-methoxycarbonyl-phenyl; 2-bromo-4-methanesulfonyl-5-methoxy-phenyl; 2-bromo-4-methyl-5-methoxy-phenyl; 2-bromo-4-chloro-5-(methoxycarbonyl-methoxy)-phenyl; 2-bromo-4-chloro-5-(hydroxycarbonyl-methoxy)-phenyl; 2-bromo-4-chloro-5-(2-methoxyethoxy)-phenyl; 4,5-dimethoxy-phenyl; 2-fluoro-4-chloro-5-methoxy-phenyl; 2-bromo-4-methoxycarbonyl-5-methoxy-phenyl; 6-bromo-benzo[1,3]dioxol-5-yl; 2-bromo-4-chloro-5-(2-hydroxyethoxy)-phenyl; 2-bromo-4-difluoromethoxy-5-methoxy-phenyl; 5-methoxy-4-methyl-phenyl; 2-bromo-4-chloro-5-(2-methylamino-ethoxy)-phenyl; 2-bromo-4-cyano-5-methyl-phenyl; 2-fluoro-4-methyl-5-methoxy-phenyl; 2-bromo-4-chloro-5-acetyl-phenyl; 5-methoxy-2-methyl-phenyl; 2-bromo-4-chloro-5-(3-methanesulfonyl-propoxy)-phenyl; 2-bromo-5-methoxy-4-(tert-butoxycarbonyl)-phenyl; 5-methanesulfonyl-2-methoxy-phenyl; 2-bromo-4-chloro-5-(1-hydroxyethyl)-phenyl; 2-fluoro-5-(2-hydroxyethoxy)-4-methyl-phenyl; 2-bromo-5-methoxy-4-amino carbonyl-phenyl; 6-bromo-2,2-difluoro-benzo[1,3]dioxol-5-yl; 2,6-difluoro-phenyl; 2-bromo-4-cyano-5-methoxy-phenyl; 2,5-dimethoxy-phenyl; 3-methoxycarbonyl-2-methyl-phenyl; 3-methoxy-phenyl; 4-methoxy-phenyl; 2,4-dimethoxy-phenyl; 4-chloro-5-methoxy-phenyl; 4-fluoro-5-methoxy-phenyl; 2-bromo-4-methyl-5-(tert-butoxycarbonyl)-phenyl; 3,4,5-trimethoxy-phenyl; 2-bromo-4,6-difluoro-phenyl; 2-ethyl-4,5-dimethoxy-phenyl; 2-bromo-4-methoxy-phenyl; 4-chloro-5-(2-hydroxyethoxy)-2-methyl-phenyl; 3-methoxycarbonyl-2-methyl-phenyl; 2,5-dimethyl-phenyl; 2-bromo-5-methoxy-phenyl; 2,3-dimethyl-phenyl; 2-bromo-4-chloro-5-hydroxymethyl-phenyl; 2-bromo-3,5-dimethyl-phenyl; 4-methoxy-2-methyl-phenyl; or 2,4-dimethyl-phenyl.

In certain embodiments of formula I, R$^1$ is: 2-bromo-4,5-dimethoxy-phenyl; 2-bromo-4-chloro-5-methoxy-phenyl; 2-bromo-4-fluoro-5-methoxy-phenyl; 2-bromo-5-methoxy-4-methyl-phenyl; 2-methyl-4,5-dimethoxy-phenyl; 2-bromo-4-chloro-5-(2-methoxy-ethyl-phenyl; 2-bromo-4-chloro-5-(2-hydroxy-ethyl-phenyl; 2-bromo-4-difluoromethoxy-5-methoxy-phenyl; 2,5-dimethoxy-phenyl; 2-ethyl-4,5-dimethoxy-phenyl; 2-methyl-5-(2-hydroxy-ethoxy)-4-chloro-phenyl; 2,5-dimethyl-phenyl; 2-bromo-5-methoxy-phenyl; or 2-bromo-4,5-dimethyl-phenyl.

In certain embodiments of formula I, R$^1$ is: 2-bromo-4,5-dimethoxy-phenyl; 2-bromo-4-chloro-5-methoxy-phenyl; 2-bromo-4-fluoro-5-methoxy-phenyl; 2-bromo-5-methoxy-4-methyl-phenyl; 4,5-dimethoxy-2-methyl-phenyl; 2-bromo-4,5-methylenedioxy-phenyl (6-bromo-benzo[1,3]dioxol-5-yl); 2-bromo-4-chloro-5-(2-hydroxy-ethoxy)-phenyl; 2-bromo-4-difluoromethoxy-5-methoxy-phenyl; 5-methoxy-2-methyl-phenyl; 2-bromo-4-chloro-5-(1-hydroxy-ethyl)-phenyl; 2-bromo-4-chloro-5-((S)-1-hydroxyethyl)-phenyl; 2-ethyl-4,5-dimethoxy-phenyl; 2-bromo-4-methoxy-phenyl; 4-chloro-5-(2-hydroxy-ethoxy)-2-methyl-phenyl; 2,5-dimethyl-phenyl; 2-bromo-5-methoxy-phenyl; 2,3-dimethyl-phenyl; 2-bromo-4-chloro-5-hydroxymethyl-phenyl; 2-bromo-3,5-dimethyl-phenyl; 2,4-dimethyl-phenyl; 3-methoxy-2-methyl-phenyl; 4-fluoro-5-(2-hydroxy-ethoxy)-2-methyl-phenyl; 4-chloro-5-(3-hydroxy-propoxy)-2-methyl-phenyl; 4-chloro-5-hydroxymethyl-2-methyl-phenyl; 5-{[bis-(2-hydroxy-ethyl)-amino]-methyl}-4-chloro-2-methyl-phenyl; 4-chloro-5-(2-hydroxy-ethyl)-2-methyl-phenyl; 2-bromo-4,5-ethylenedioxy-phenyl (7-bromo-2,3-dihydro-benzo[1,4]dioxin-6-yl); 3-chloro-2-methyl-phenyl; 3-hydroxymethyl-2-methyl-phenyl; or 3-(2-hydroxy-ethyl)-2-methyl-phenyl;

In certain embodiments of formula I, R$^1$ is 2-bromo-4,5-dimethoxy-phenyl.

In certain embodiments of formula I, R$^1$ is 2-bromo-4-chloro-5-methoxy-phenyl.

In certain embodiments of formula I, R$^1$ is 2-bromo-4-fluoro-5-methoxy-phenyl.

In certain embodiments of formula I, R$^1$ is 2-bromo-5-methoxy-4-methyl-phenyl.

In certain embodiments of formula I, R$^1$ is 2-methyl-4,5-dimethoxy-phenyl.

In certain embodiments of formula I, R$^1$ is 2-bromo-4-chloro-5-(2-methoxy-ethyl-phenyl.

In certain embodiments of formula I, R$^1$ is 2-bromo-4-chloro-5-(2-hydroxy-ethyl-phenyl.

In certain embodiments of formula I, R$^1$ is 2-bromo-4-difluoromethoxy-5-methoxy-phenyl.

In certain embodiments of formula I, R$^1$ is 2,5-dimethoxy-phenyl.

In certain embodiments of formula I, R$^1$ is 2-ethyl-4,5-dimethoxy-phenyl.

In certain embodiments of formula I, R$^1$ is 2-methyl-5-(2-hydroxy-ethoxy)-4-chloro-phenyl.

In certain embodiments of formula I, R$^1$ is 2,5-dimethyl-phenyl.

In certain embodiments of formula I, R$^1$ is 2-bromo-5-methoxy-phenyl.

In certain embodiments of formula I, R$^1$ is 2-bromo-4,5-dimethyl-phenyl.

In certain embodiments of formula I, R$^1$ is optionally substituted heteroaryl. In certain embodiments such heteroaryl may comprise: pyridinyl; indazolyl; indolyl; quinolinyl; quinoxalinylthiophenyl; benzimidazolyl; benzofuranyl; dihydroindolyl; tetrahydroquinolinyl; pyrazolyl; 2,3-dihydrobenzimidazolyl; benzothiazolyl; 2-oxo-1,2,3,4-tetrahydroquinolinyl; 2-oxo-2,3-dihydro-indolyl; 4-oxo-3,4-dihydro-quinazolinyl; 3,4-dihydrobenzo[1,4]oxazinyl; 2,3-dihydrobenzofuranyl; each of which may be optionally substituted once or twice with a substituent or substituents independently selected from: fluoro; chloro; bromo; methyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, R$^1$ is optionally substituted heteroaryl. In certain embodiments such heteroaryl may comprise: pyridinyl; indazolyl; indolyl; quinolinyl; quinoxalinyl; thiophenyl; benzimidazolyl; benzofuranyl; dihydroindolyl; tetrahydroquinolinyl; pyrazolyl; 2-oxo-2,3-dihydro-benzimidazolyl; 2,3-dihydrobenzimidazolyl; benzothiazolyl; 2-oxo-1,2,3,4-tetrahydroquinolinyl; 2-oxo-3,4-dihydro-indolyl; 4-oxo-3,4-dihydro-quinazolinyl; 3,4-dihydroquinolinyl; 3,4-dihydrobenzo[1,4]oxazinyl; 2,3-dihydrobenzo furanyl; each of which may be optionally substituted once or twice with a substituent or substituents independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; or hydroxyethyl.

In certain embodiments of formula I, R$^1$ is heteroaryl selected from: pyridinyl; indazolyl; indolyl; quinolinyl; quinoxalinyl; thiophenyl; benzimidazolyl; benzofuranyl; dihydroindolyl; tetrahydroquinolinyl; pyrazolyl; 2,3-dihydrobenzimidazolyl; benzothiazolyl; 2-oxo-1,2,3,4-tetrahydroquinolinyl; 2-oxo-2,3-dihydro-indolyl; 4-oxo-3,4-dihydro-quinazolinyl; 3,4-dihydrobenzo[1,4]oxazinyl; 2,3-dihydrobenzofuranyl; each of which may be optionally substituted once or twice with halo, $C_{1-6}$alkyl or $C_{1-6}$alkoxy.

In certain embodiments of formula I, R$^1$ is heteroaryl selected from: pyridinyl; indazolyl; indolyl; quinolinyl; quinoxalinyl; thiophenyl; benzimidazolyl; benzofuranyl; dihydroindolyl; tetrahydroquinolinyl; pyrazolyl; 2,3-dihydrobenzimidazolyl; benzothiazolyl; 2-oxo-1,2,3,4-tetrahydroquinolinyl; 2-oxo-2,3-dihydro-indolyl; 4-oxo-3,4-dihydro-quinazolinyl; 3,4-dihydrobenzo[1,4]oxazinyl; 2,3-dihydrobenzofuranyl; each of which may be optionally substituted once or twice with halo or $C_{1-6}$alkyl.

In certain embodiments of formula I, R$^1$ is heteroaryl selected from: pyridin-2-yl; pyridin-4-yl; indazol-6-yl; indazol-5-yl; 3,4-dihydroquinolin-1-yl; indolyl-6-yl; indolyl-5-yl; quinolin-6-yl; quinolin-7-yl; quinolin-5-yl; quinolin-6-yl;

quinoxalin-6-yl; thiophen-3-yl; benzimidazol-5-yl; benzofuran-5-yl; 2-oxo-2,3-dihydro-benzimidazol-5-yl; dihydroindolyl; tetrahydroquinolinyl; pyrazol-3-yl; 2,3-dihydrobenzimidazolyl; benzothiazol-5-yl; benzothiazol-6-yl; 2-oxo-1,2,3,4-tetrahydroquinolin-7-yl; 2-oxo-3,4-dihydro-indol-6-yl; 4-oxo-3,4-dihydro-quinazolin-6-yl; 3,4-dihydrobenzo[1,4]oxazin-7-yl; 2,3-dihydrobenzofuran-4-yl; each of which may be optionally substituted once or twice with halo or $C_{1-6}$alkyl.

In certain embodiments of formula I, $R^1$ is heteroaryl selected from: pyridin-2-yl; pyridin-4-yl; indazol-6-yl; indazol-5-yl; 3,4-dihydroquinolin-1-yl; indolyl-6-yl; indolyl-5-yl; quinolin-6-yl; quinolin-7-yl; quinolin-5-yl; quinolin-6-yl; quinoxalin-6-yl; thiophen-3-yl; benzimidazol-5-yl; benzofuran-5-yl; 2-oxo-2,3-dihydro-benzimidazol-5-yl; dihydroindolyl; tetrahydroquinolinyl; pyrazol-3-yl; 2,3-dihydrobenzimidazolyl; benzothiazol-5-yl; benzothiazol-6-yl; 2-oxo-1,2,3,4-tetrahydroquinolin-7-yl; 2-oxo-3,4-dihydro-indol-6-yl; 4-oxo-3,4-dihydro-quinazolin-6-yl; 3,4-dihydrobenzo[1,4]oxazin-7-yl; 2,3-dihydrobenzofuran-4-yl; each of which may be optionally substituted once or twice with halo or $C_{1-6}$alkyl.

In certain embodiments of formula I, $R^1$ is heteroaryl selected from: 3-bromo-6-methoxy-pyridin-2-yl; 5-bromo-3-methyl-1-(toluene-4-sulfonyl)-indazol-6-yl; 5-bromo-3-methyl-indazol-6-yl; 5-bromo-3-methyl-indazol-6-yl; 1-methyl-indol-6-yl; 7-methyl-quinolin-6-yl; 2-bromo-thiophen-3-yl; indol-6-yl; 2-methyl-benzofuran-5-yl; 1-methyl-1H-indol-6-yl; 6-methyl-quinolin-7-yl; 5-bromo-quinolin-6-yl; 7-methyl-quinoxalin-6-yl; 2,5-dimethyl-pyrazol-3-yl; 2-methyl-benzothiazol-5-yl; 6-bromo-2-oxo-2,3-dihydro-benzoimidazol-5-yl; 1-methyl-1H-indol-5-yl; benzothiazol-6-yl; 5-methyl-quinolin-6-yl; 6-bromo-1-methyl-2-oxo-1,2,3,4-tetrahydro-quinolin-7-yl; 2-oxo-2,3-dihydro-1H-indol-6-yl; 1-oxo-1,2,3,4-tetrahydro-isoquinolin-7-yl; 1,5-dimethyl-indol-6-yl; 4,6-dimethyl-3,4-dihydro-benzo[1,4]oxazin-7-yl; 1,3-dimethyl-indazol-6-yl; 2,3-dimethyl-indazol-6-yl; 2-methyl-indazol-6-yl; 2-methyl-indazol-5-yl; 5-ethyl-quinolin-6-yl; 7-bromo-2,3-dimethyl-indazol-6-yl; 2,3-dihydro-benzofuran-4-yl; 7-ethyl-quinolin-6-yl; quinolin-5-yl; 1-(2-hydroxy-ethyl)-5-methyl-1H-indol-6-yl; 1-methyl-indazol-6-yl; 7-bromo-1-methyl-indazol-6-yl; and 7-bromo-2-methyl-indazol-6-yl.

In certain embodiments of formula I, $R^1$ is indazolyl optionally substituted once or twice with halo or $C_{1-6}$alkyl.

In certain embodiments of formula I, $R^1$ is quinolinyl optionally substituted once or twice with halo or $C_{1-6}$alkyl.

In certain embodiments of formula I, $R^1$ is optionally substituted heteroaryl. In certain embodiments such heteroaryl may comprise: pyridinyl; indazolyl; indolyl; quinolinyl; or benzofuranyl; each of which may be optionally substituted one, two or three times with a substituent or substituents independently selected from: fluoro; chloro; bromo; methyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, $R^1$ is adamantyl.

In certain embodiments of formula I, $R^2$ is optionally substituted aryl.

In certain embodiments of formula I, $R^2$ is $C_{1-6}$alkyl.

In certain embodiments of formula I, $R^2$ is optionally substituted phenyl.

In certain embodiments of formula I, $R^2$ is phenyl optionally substituted one, two, three or four times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfonyl-$C_{1-6}$alkoxy; hydroxy-$C_{1-6}$alkyl; $C_{3-6}$cycloalkyl-$C_{1-6}$alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonyl$C_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$alkyl; or nitro; or two adjacent substituents may form a $C_{1-2}$alkylenedioxy or halo-$C_{1-2}$alkylenedioxy.

In certain embodiments of formula I, $R^2$ is phenyl optionally substituted once or twice with a substituent or substituents each independently selected from: fluoro; chloro; bromo; iodo; methyl; ethyl; methoxy; ethoxy; trifluoromethyl; difluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; or two adjacent substituents may form methylenedioxy, ethylenedioxy or difluoromethylenedioxy.

In certain embodiments of formula I, $R^2$ is phenyl optionally substituted once or twice with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; alkoxyalkoxy; hydroxyalkoxy; alkylsulfonylalkoxy; hydroxyalkyl; or $C_{3-6}$cycloalkyl-$C_{1-6}$alkoxy.

In certain embodiments of formula I, $R^2$ is phenyl optionally substituted once or twice with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; or cyclopropylmethoxy.

In certain embodiments of formula I, $R^2$ is phenyl optionally substituted once or twice with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

In certain embodiments of formula I, $R^2$ is phenyl substituted once or twice with a substituent or substituents each independently selected from: halo; methyl; methoxy; trifluoromethyl; difluoromethoxy; nitrile; or methanesulfonyl.

In certain embodiments of formula I, $R^2$ is phenyl substituted once or twice with a substituent or substituents each independently selected from: fluoro; chloro; methyl; methoxy; or nitrile.

In certain embodiments of formula I, $R^2$ is phenyl substituted once or twice with fluoro.

In certain embodiments of formula I, $R^2$ is: phenyl; 4-fluoro-phenyl; 3-fluoro-phenyl; 2-fluoro-phenyl; 2-chlorophenyl; 3,4-difluoro-phenyl; 3,5-difluoro-phenyl; 3-methylphenyl; 4-methyl-phenyl; or 3-cyano-phenyl.

In certain embodiments of formula I, $R^2$ is: phenyl; 4-fluoro-phenyl; 3-fluoro-phenyl; 2-fluoro-phenyl; 2-chlorophenyl; 3,4-difluoro-phenyl; or 3,5-difluoro-phenyl.

In certain embodiments of formula I, $R^2$ is 4-fluoro-phenyl.

In certain embodiments of formula I, $R^2$ is 3-fluoro-phenyl.

In certain embodiments of formula I, $R^2$ is 3,4-difluorophenyl.

In certain embodiments, the compounds of formula I may be more specifically of formula II:

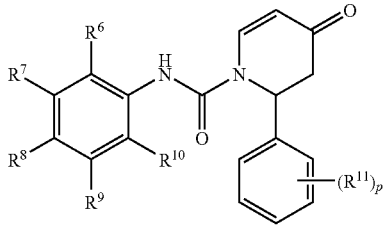

wherein:

p is from 0 to 3;

$R^6$, $R^7$, $R^8$, $R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; $C_{1-6}$alkylcarbonyl; aminocarbonyl; $C_{1-6}$alkoxycarbonyl; $C_{1-6}$alkoxycarbonyl-$C_{1-6}$alkoxy; hydroxycarbonyl; hydroxycarbonyl-$C_{1-6}$alkoxy; $C_{1-6}$alkylaminocarbonyl-$C_{1-6}$alkoxy; $C_{1-6}$alkoxy-$C_{1-6}$alkoxy; hydroxy-$C_{1-6}$alkoxy; $C_{1-6}$alkylamino-$C_{1-6}$alkoxy; $C_{1-6}$alkylsulfonyl-$C_{1-6}$alkoxy; hydroxy-$C_{1-6}$alkyl; $C_{3-6}$cycloalkyl-$C_{1-6}$alkoxy; amino; amino-$C_{1-6}$alkyl; $C_{1-6}$alkenyl; $C_{1-6}$alkynyl; morpholinyl; morpholinyl-$C_{1-6}$alkyl; piperazinyl; piperidinyloxy; aminocarbonyl-$C_{1-6}$alkoxy; $C_{1-6}$alkoxyamino-$C_{1-6}$alkyl; hydroxy-$C_{1-6}$alkylamino-$C_{1-6}$alkyl; $C_{1-6}$alkoxycarbonylamino-$C_{1-6}$alkyl; $C_{1-6}$alkylcarbonylamino-$C_{1-6}$alkyl; $C_{1-6}$alkylaminocarbonyl; $C_{1-6}$alkoxycarbonyl$C_{1-6}$alkyl; $C_{1-6}$alkylaminocarbonyl-$C_{1-6}$alkyl; $C_{1-6}$alkylamino-$C_{1-6}$alkyl; hydroxycarbonyl-$C_{1-6}$alkyl; or nitro; or two adjacent substituents may form a $C_{1-2}$alkylenedioxy or halo-$C_{1-2}$alkylenedioxy; and each $R^{11}$ independently is: halo; $C_{1-6}$alkyl; $C_{1-6}$alkoxy; halo-$C_{1-6}$alkyl; halo-$C_{1-6}$alkoxy; $C_{1-6}$alkylsulfonyl; or nitrile.

In certain embodiments of formula II, the subject compounds may be more specifically of formula IIa or formula IIb;

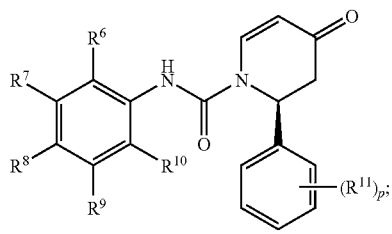

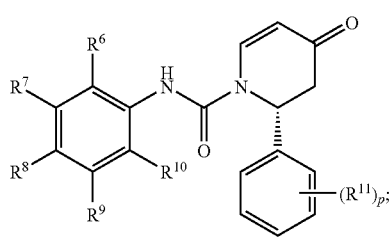

wherein p, $R^6$, $R^7$, $R^8$, $R^9$, $R^{10}$ and $R^{11}$ are as defined herein.

In certain embodiments the subject compounds are of formula IIa.

In certain embodiments the subject compounds are of formula IIb.

In certain\ embodiments of any of formulas II, IIa and IIb, at least two of $R^6$, $R^7$, $R^8$, $R^9$ and $R^{10}$ are not hydrogen.

In certain embodiments of any of formulas II, IIa and IIb, at least three of $R^6$, $R^7$, $R^8$, $R^9$ and $R^{10}$ are not hydrogen.

In certain embodiments of any of formulas II, IIa and IIb, $R^6$, $R^7$, $R^8$, $R^9$ and $R^{10}$ each independently is: hydrogen; fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; or two adjacent substituents may form methylenedioxy, ethylenedioxy or difluoromethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; or ethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; methyl; ethyl; methoxy; ethoxy; difluoromethoxy; methoxyethoxy; hydroxyethoxy; hydroxymethyl; hydroxyethyl; hydroxypropoxy; methylenedioxy; or ethylenedioxy.

In certain embodiments of any of formulas II, IIa and IIb, two of $R^6$, $R^7$, $R^8$, $R^9$ and $R^{10}$ are hydrogen, and the remaining ones of $R^6$, $R^7$, $R^8$, $R^9$ and $R^{10}$ of each independently is: hydrogen; fluoro; chloro; bromo; methyl; and methoxy.

In certain embodiments of any of formulas II, IIa and IIb, $R^6$, $R^7$, $R^8$, $R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; alkoxyalkoxy; hydroxyalkoxy; alkylsulfonylalkoxy; hydroxyalkyl; or $C_{3-6}$cycloalkyl-$C_{1-6}$alkoxy.

In certain embodiments of any of formulas II, IIa and IIb, $R^6$, $R^7$, $R^8$, $R^9$ and $R^{10}$ each independently is: hydrogen; fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; or hydroxyethyl.

In certain embodiments of any of formulas II, IIa and IIb, $R^6$, $R^7$, $R^8$, $R^9$ and $R^{10}$ each independently is: hydrogen; fluoro; chloro; bromo; methyl; ethyl; methoxy; ethoxy; trif luoromethyl; difluoromethoxy; nitrile; methoxyethoxy; hydroxyethoxy; hydroxymethyl; hydroxyethyl; or cyclopropylmethoxy.

In certain embodiments of any of formulas II, IIa and IIb, $R^7$ and $R^{10}$ are hydrogen.

In certain embodiments of any of formulas II, IIa and IIb, $R^6$ is: hydrogen; halo; or methyl.

In certain embodiments of any of formulas II, IIa and IIb, $R^8$ is: hydrogen; methoxy; halo; methyl; or difluoromethoxy.

In certain embodiments of any of formulas II, IIa and IIb, $R^9$ is: methoxy; hydrogen; 2-hydroxy-ethoxy; 2-methoxy-ethoxy; 1-hydroxy-ethyl; or cyclopropylmethyl.

In certain embodiments of any of formulas II, IIa and IIb, p is 0, 1 or 2.

In certain embodiments of any of formulas II, IIa and IIb, p is 1 or 2.

In certain embodiments of any of formulas II, IIa and IIb, p is 1.

In certain embodiments of any of formulas II, IIa and IIb, each $R^{11}$ independently is: halo; $C_{1-6}$alkyl; or $C_{1-6}$alkoxy.

In certain embodiments of any of formulas II, IIa and IIb, each $R^{11}$ independently is fluoro or methyl.

In certain embodiments of any of formulas II, IIa and IIb, $R^{11}$ is halo.

In certain embodiments of any of formulas II, IIa and IIb, $R^{11}$ is fluoro.

In certain embodiments of any of formulas II, IIa and IIb:
$R^6$ is: hydrogen; halo; methyl; or ethyl;
$R^7$ is hydrogen; methyl; methoxy; or methoxycarbonyl;
$R^8$ is: hydrogen; methoxy; halo; methyl; or difluoromethoxy;
$R^9$ is: hydrogen; methoxy; hydrogen; 2-hydroxy-ethoxy; 2-methoxy-ethoxy; or 1-hydroxy-ethyl; and
$R^{10}$ is hydrogen; or halo.

In certain embodiments of any of formulas II, IIa and IIb:
$R^6$ is: halo; or methyl;
$R^7$ is hydrogen;
$R^8$ is: methoxy; halo; methyl; or difluoromethoxy;
$R^9$ is: methoxy; 2-hydroxy-ethoxy; 2-methoxy-ethoxy; or 1-hydroxy-ethyl; and
$R^{10}$ is hydrogen; or halo.

In certain embodiments of any of formulas II, IIa and IIb:
$R^6$ is: bromo; or methyl;
$R^7$ is hydrogen;
$R^8$ is: methoxy; chloro; fluoro; methyl; or difluoromethoxy;
$R^9$ is: methoxy; 2-hydroxy-ethoxy; 2-methoxy-ethoxy; or 1-hydroxy-ethyl; and
$R^{10}$ is hydrogen.

In certain embodiments of any of formulas II, IIa and IIb, p is 1 or 2 and $R^{11}$ is halo.

In certain embodiments of any of formulas II, IIa and IIb, p is 1 or 2 and $R^{11}$ is fluoro.

In certain embodiments of any of formulas II, IIa and IIb, p is 1 and $R^{11}$ is fluoro.

In certain embodiments of any of formulas II, IIa and IIb, p is 1 and $R^{11}$ is fluoro at the 4-position.

In certain embodiments, the compounds of formula I may be more specifically of formula III:

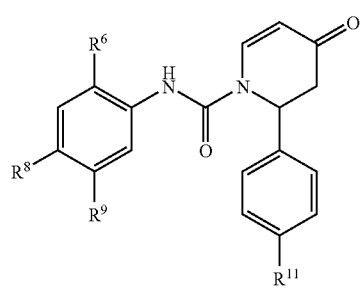

wherein $R^6$, $R^8$, $R^9$ and $R^{11}$ are as defined herein.

In certain embodiments of formula III, the subject compounds may be more specifically of formula IIIa or formula IIIb;

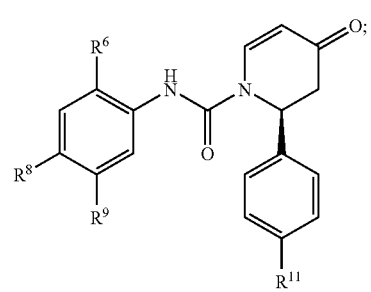

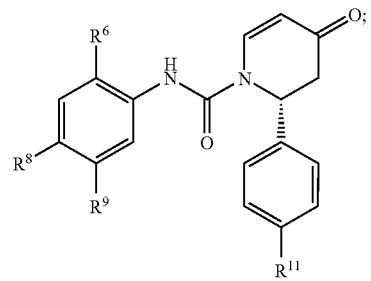

wherein $R^6$, $R^8$, $R^9$ and $R^{11}$ are as defined herein.

In certain embodiments the subject compounds are of formula IIIa.

In certain embodiments the subject compounds are of formula IIIb.

In certain embodiments of any of formulas III, IIIa and IIIb, $R^6$ is: halo; methyl; or ethyl.

In certain embodiments of any of formulas III, IIIa and IIIb, $R^8$ is: methoxy; halo; methyl; or difluoromethoxy.

In certain embodiments of any of formulas III, IIIa and IIIb, $R^9$ is: methoxy; 2-hydroxy-ethoxy; 2-methoxy-ethoxy; or 1-hydroxy-ethyl.

In certain embodiments of any of formulas III, IIIa and IIIb, $R^6$ is: bromo; or methyl;

In certain embodiments of any of formulas III, IIIa and IIIb, $R^8$ is: methoxy; chloro; fluoro; methyl; or difluoromethoxy.

In certain embodiments of any of formulas III, IIIa and IIIb, $R^9$ is: methoxy; 2-hydroxy-ethoxy; 2-methoxy-ethoxy; or 1-hydroxy-ethyl.

In certain embodiments of any of formulas III, IIIa and IIIb, $R^{11}$ is halo.

In certain embodiments of any of formulas III, IIIa and IIIb, $R^{11}$ is fluoro.

Where any of $R^1$, $R^2$, $R^3$, $R^4$, $R^5$, $R^6$, $R^7$, $R^8$, $R^9$, $R^{10}$ or $R^{11}$ is alkyl or contains an alkyl moiety, such alkyl is preferably lower alkyl, i.e. $C_1$-$C_6$alkyl, and in many embodiments is $C_1$-$C_4$alkyl.

The invention also provides methods for treating a disease or condition mediated by or otherwise associated with a $P2X_7$ receptor, the method comprising administering to a subject in need thereof an effective amount of a compound of the invention.

The invention also provides methods for treating an inflammatory, respiratory or diabetes condition, the method comprising administering to a subject in need thereof an effective amount of a compound of the invention together with an effective amount of a P2X3 inhibitor.

The disease may be an inflammatory disease such as arthritis, and more particularly rheumatoid arthritis, osteoarthritis, psoriasis, allergic dermatitis, asthma, chronic obstructive pulmonary disease, airways hyper-responsiveness, septic shock, glomerulonephritis, irritable bowel disease, and Crohn's disease.

The disease may be a pain condition, such as inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

The disease may be a respiratory disorder, such as chronic obstructive pulmonary disorder (COPD), asthma, or bronchospasm, or a gastrointestinal (GI) disorder such as Irritable Bowel Syndrome (IBS), Inflammatory Bowel Disease (IBD), biliary colic and other biliary disorders, renal colic, diarrhea-dominant IBS, pain associated with GI distension.

The disease may be diabetes.

Representative compounds in accordance with the methods of the invention are shown in Table 1, together with $pIC_{50}$ values for P2X7.

TABLE 1

| # | Structure | Name | M + H/MP | $pIC_{50}$ |
|---|---|---|---|---|
| 1 | 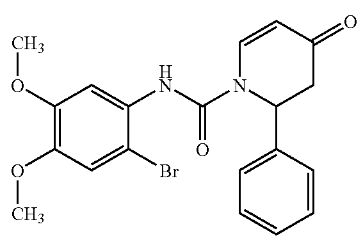 | 4-Oxo-2-phenyl-3,4-dihydro-2H-pyridine-1-carboxylic acid (2-bromo-4,5-dimethoxy-phenyl)-amide | 432 | 7.408 |
| 2 | 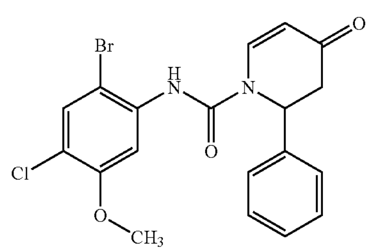 | 4-Oxo-2-phenyl-3,4-dihydro-2H-pyridine-1-carboxylic acid (2-bromo-4-chloro-5-methoxy-phenyl)-amide | 436 | 6.425 |
| 3 | 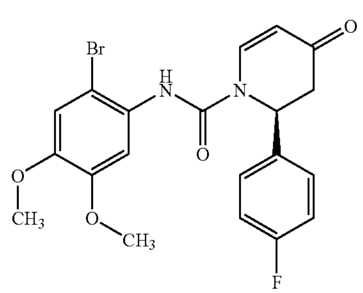 | (S)-2-(4-Fluoro-phenyl)-4-oxo-3,4-dihydro-2H-pyridine-1-carboxylic acid (2-bromo-4,5-dimethoxy-phenyl)-amide | 450 | 8.055 |
| 4 | 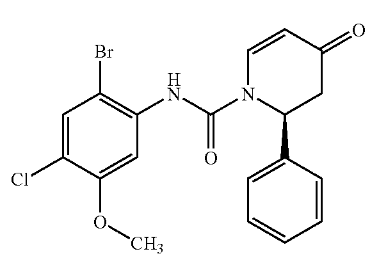 | (S)-4-Oxo-2-phenyl-3,4-dihydro-2H-pyridine-1-carboxylic acid (2-bromo-4-chloro-5-methoxy-phenyl)-amide | 436 | 7.476 |

TABLE 1-continued

| # | Structure | Name | M + H/MP | pIC$_{50}$ |
|---|---|---|---|---|
| 5 | 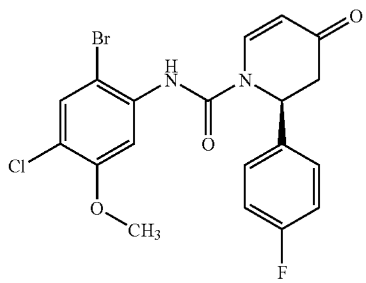 | (S)-2-(4-Fluoro-phenyl)-4-oxo-3,4-dihydro-2H-pyridine-1-carboxylic acid (2-bromo-4-chloro-5-methoxy-phenyl)-amide | 454 | 7.4325 |
| 6 | 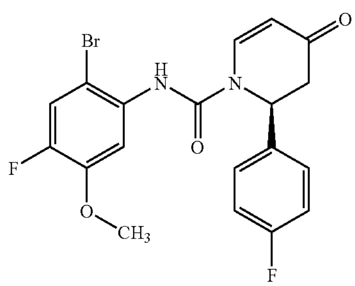 | (S)-2-(4-Fluoro-phenyl)-4-oxo-3,4-dihydro-2H-pyridine-1-carboxylic acid (2-bromo-4-fluoro-5-methoxy-phenyl)-amide | 438 | 7.5 |
| 7 | 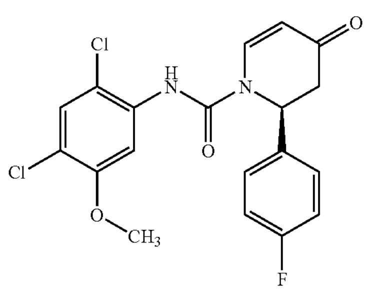 | (S)-2-(4-Fluoro-phenyl)-4-oxo-3,4-dihydro-2H-pyridine-1-carboxylic acid (2,4-dichloro-5-methoxy-phenyl)-amide | 410 | 6.73 |
| 8 | 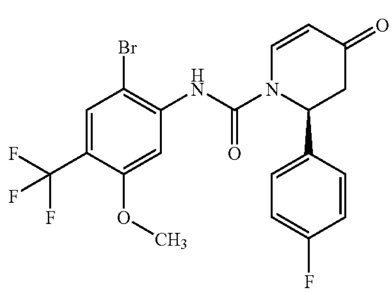 | (S)-2-(4-Fluoro-phenyl)-4-oxo-3,4-dihydro-2H-pyridine-1-carboxylic acid (2-bromo-5-methoxy-4-trifluoromethyl-phenyl)-amide | 488 | 6.09 |
| 9 | 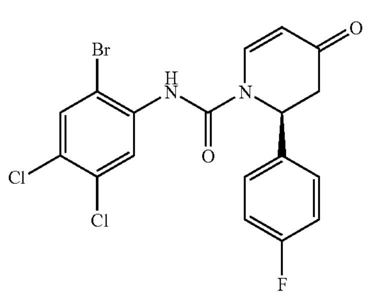 | (S)-2-(4-Fluoro-phenyl)-4-oxo-3,4-dihydro-2H-pyridine-1-carboxylic acid (2-bromo-4,5-dichloro-phenyl)-amide | 459 | 6.11 |

TABLE 1-continued

| # | Structure | Name | M + H/MP | pIC$_{50}$ |
|---|---|---|---|---|
| 10 | 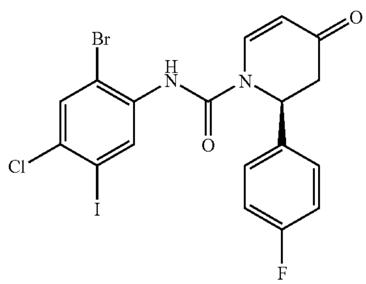 | (S)-2-(4-Fluoro-phenyl)-4-oxo-3,4-dihydro-2H-pyridine-1-carboxylic acid (2-bromo-4-chloro-5-iodo-phenyl)-amide | 550 | 6.5175 |
| 11 | 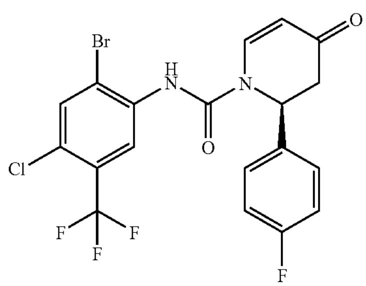 | (S)-2-(4-Fluoro-phenyl)-4-oxo-3,4-dihydro-2H-pyridine-1-carboxylic acid (2-bromo-4-chloro-5-trifluoromethyl-phenyl)-amide | 492 | 6.015 |
| 12 | 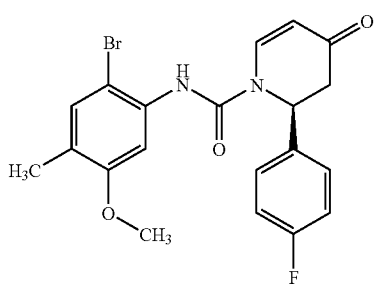 | (S)-2-(4-Fluoro-phenyl)-4-oxo-3,4-dihydro-2H-pyridine-1-carboxylic acid (2-bromo-5-methoxy-4-methyl-phenyl)-amide | 434 | 7.873333 |
| 13 | 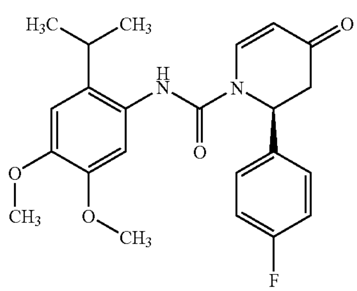 | (S)-2-(4-Fluoro-phenyl)-4-oxo-3,4-dihydro-2H-pyridine-1-carboxylic acid (2-isopropyl-4,5-dimethoxy-phenyl)-amide | 413 | 6.66 |
| 14 | 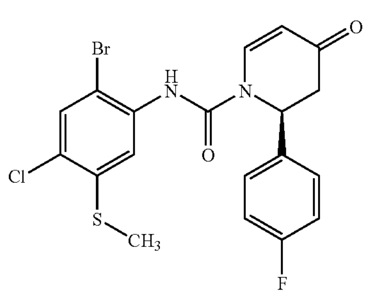 | (S)-2-(4-Fluoro-phenyl)-4-oxo-3,4-dihydro-2H-pyridine-1-carboxylic acid (2-bromo-4-chloro-5-methylsulfanyl-phenyl)-amide | 470 | 6.726 |

TABLE 1-continued

| # | Structure | Name | M + H/MP | pIC$_{50}$ |
|---|---|---|---|---|
| 15 | 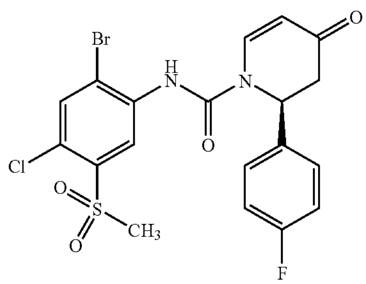 | (S)-2-(4-Fluoro-phenyl)-4-oxo-3,4-dihydro-2H-pyridine-1-carboxylic acid (2-bromo-4-chloro-5-methanesulfonyl-phenyl)-amide | 502 | 5.94 |
| 16 | 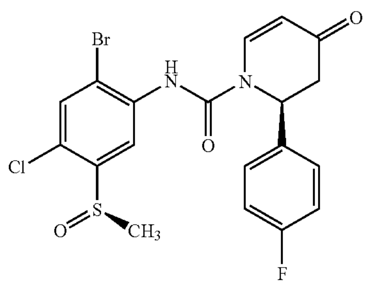 | (S)-2-(4-Fluoro-phenyl)-4-oxo-3,4-dihydro-2H-pyridine-1-carboxylic acid [2-bromo-4-chloro-5-((R)-methanesulfinyl)-phenyl]-amide | 486 | 6.623 |
| 17 | 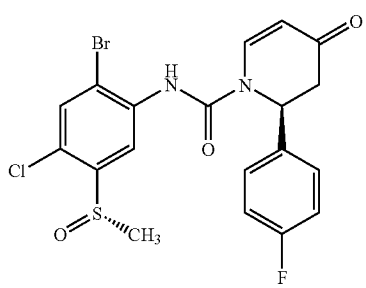 | (S)-2-(4-Fluoro-phenyl)-4-oxo-3,4-dihydro-2H-pyridine-1-carboxylic acid [2-bromo-4-chloro-5-((S)-methanesulfinyl)-phenyl]-amide | 486 | 5.86 |
| 18 | 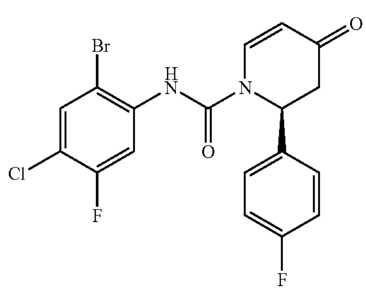 | (S)-2-(4-Fluoro-phenyl)-4-oxo-3,4-dihydro-2H-pyridine-1-carboxylic acid (2-bromo-4-chloro-5-fluoro-phenyl)-amide | 442 | 6.286 |
| 19 | 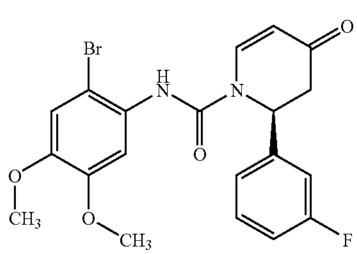 | (S)-2-(3-Fluoro-phenyl)-4-oxo-3,4-diohydro-2H-pyridine-1-carboxylic acid (2-bromo-4,5-dimethoxy-phenyl)-amide | 450 | 8.56 |

TABLE 1-continued

| # | Structure | Name | M + H/MP | pIC$_{50}$ |
|---|---|---|---|---|
| 20 | 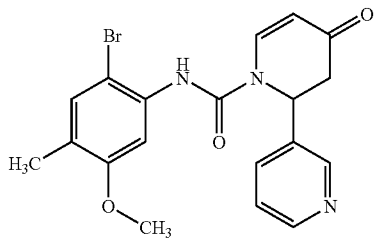 | 4-Oxo-3,4-dihydro-2H-[2,3']bipyridinyl-1-carboxylic acid (2-bromo-5-methoxy-4-methyl-phenyl)-amide | 417 | 5.995 |
| 21 | 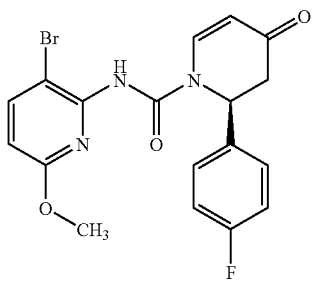 | (S)-2-(4-Fluoro-phenyl)-4-oxo-3,4-dihydro-2H-pyridine-1-carboxylic acid (3-bromo-6-methoxy-pyridin-2-yl)-amide | 421 | 6.32 |
| 22 | 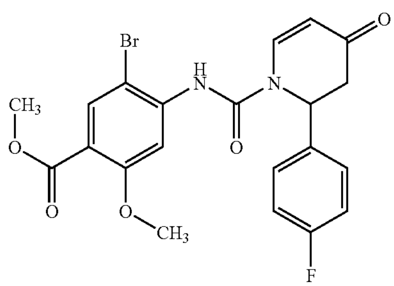 | 5-Bromo-4-{[2-(4-fluoro-phenyl)-4-oxo-3,4-dihydro-2H-pyridine-1-carbonyl]-amino}-2-methoxy-benzoic acid methyl ester | 478 | 7.15 |
| 23 | 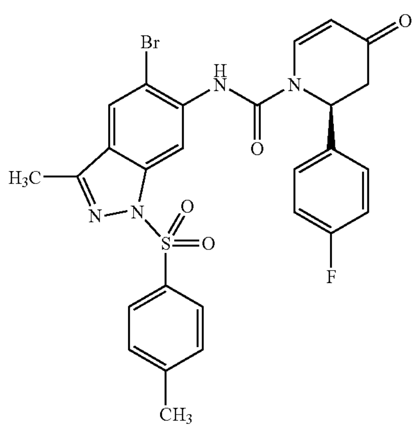 | (S)-2-(4-Fluoro-phenyl)-4-oxo-3,4-dihydro-2H-pyridine-1-carboxylic acid [5-bromo-3-methyl-1-(toluene-4-sulfonyl)-1H-indazol-6-yl]-amide | 598 | 5.245 |
| 24 | 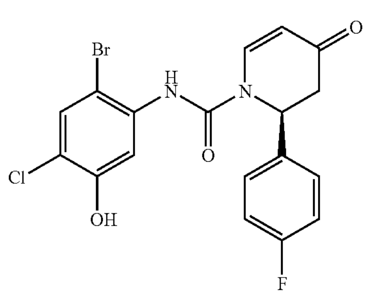 | (S)-2-(4-Fluoro-phenyl)-4-oxo-3,4-dihydro-2H-pyridine-1-carboxylic acid (2-bromo-4-chloro-5-hydroxy-phenyl)-amide | 440 | 6.71 |

TABLE 1-continued

| # | Structure | Name | M + H/MP | pIC$_{50}$ |
|---|---|---|---|---|
| 25 | 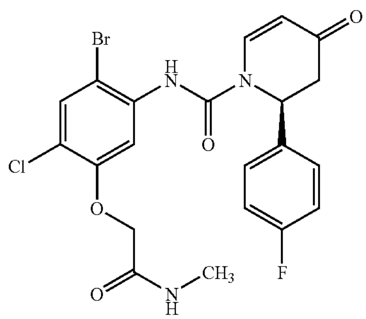 | (S)-2-(4-Fluoro-phenyl)-4-oxo-3,4-dihydro-2H-pyridine-1-carboxylic acid (2-bromo-4-chloro-5-methylcarbamoylmethoxy-phenyl)-amide | 511 | 6.785 |
| 26 | 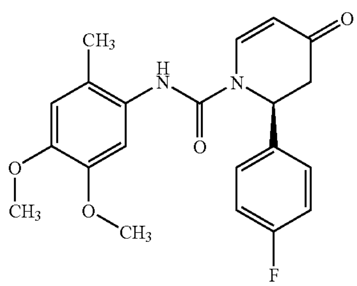 | (S)-2-(4-Fluoro-phenyl)-4-oxo-3,4-dihydro-2H-pyridine-1-carboxylic acid (4,5-dimethoxy-2-methyl-phenyl)-amide | 385 | 7.93 |
| 27 | 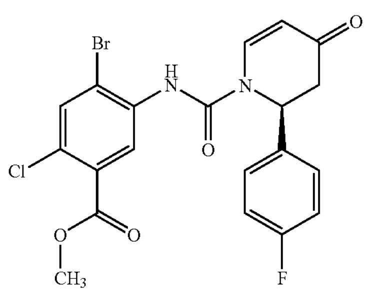 | 4-Bromo-2-chloro-5-{[(S)-2-(4-fluoro-phenyl)-4-oxo-3,4-dihydro-2H-pyridine-1-carbonyl]-amino}-benzoic acid methyl ester | 482 | 7.26 |
| 28 | 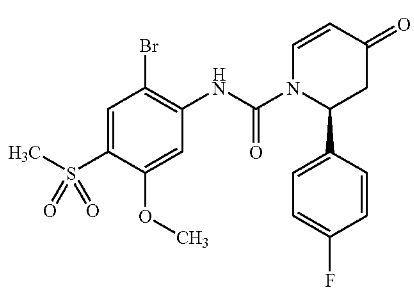 | (S)-2-(4-Fluoro-phenyl)-4-oxo-3,4-dihydro-2H-pyridine-1-carboxylic acid (2-bromo-4-methanesulfonyl-5-methoxy-phenyl)-amide | 498 | 6.435 |
| 29 | 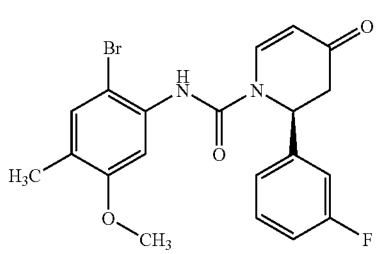 | (S)-2-(3-Fluoro-phenyl)-4-oxo-3,4-dihydro-2H-pyridine-1-carboxylic acid (2-bromo-5-methoxy-4-methyl-phenyl)-amide | 434 | 7.93 |

TABLE 1-continued

| # | Structure | Name | M + H/MP | pIC$_{50}$ |
|---|---|---|---|---|
| 30 | 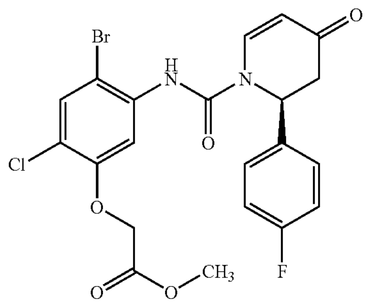 | (4-Bromo-2-chloro-5-{[(S)-2-(4-fluoro-phenyl)-4-oxo-3,4-dihydro-2H-pyridine-1-carbonyl]-amino}-phenoxy)-acetic acid methyl ester | 512 | 6.7 |
| 31 | 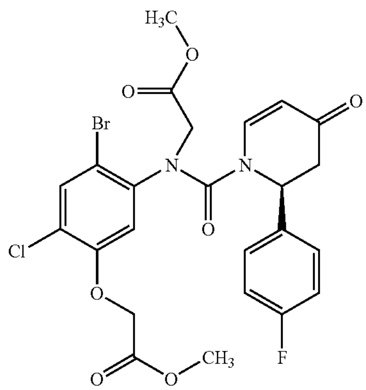 | (4-Bromo-2-chloro-5-{[(S)-2-(4-fluoro-phenyl)-4-oxo-3,4-dihydro-2H-pyridine-1-carbonyl]-methoxycarbonylmethyl-amino}-phenoxy)-acetic acid methyl ester | | 5.27 |
| 32 | 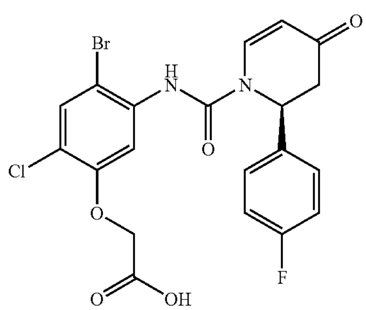 | (4-Bromo-2-chloro-5-{[(S)-2-(4-fluoro-phenyl)-4-oxo-3,4-dihydro-2H-pyridine-1-carbonyl]-amino}-phenoxy)-acetic acid | 498 | 5.365 |
| 33 | 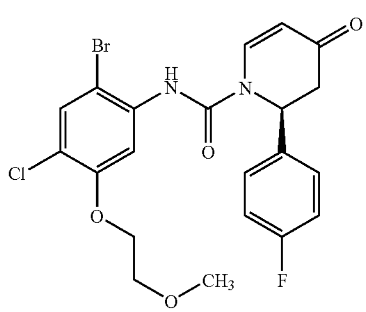 | (S)-2-(4-Fluoro-phenyl)-4-oxo-3,4-dihydro-2H-pyridine-1-carboxylic acid [2-bromo-4-chloro-5-(2-methoxy-ethoxy)-phenyl]-amide | 498 | 7.27 |
| 34 | 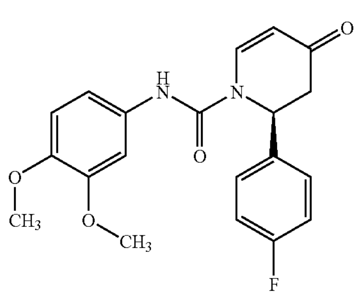 | (S)-2-(4-Fluoro-phenyl)-4-oxo-3,4-dihydro-2H-pyridine-1-carboxylic acid (3,4-dimethoxy-phenyl)-amide | 371 | 7.2425 |

TABLE 1-continued

| # | Structure | Name | M + H/MP | pIC$_{50}$ |
|---|---|---|---|---|
| 35 | 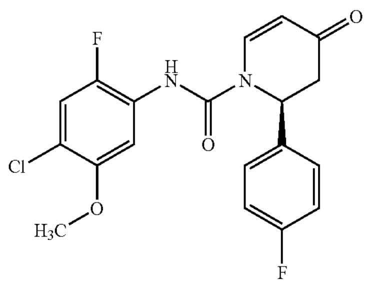 | (S)-2-(4-Fluoro-phenyl)-4-oxo-3,4-dihydro-2H-pyridine-1-carboxylic acid (4-chloro-2-fluoro-5-methoxy-phenyl)-amide | 393 | 7.195 |
| 36 | 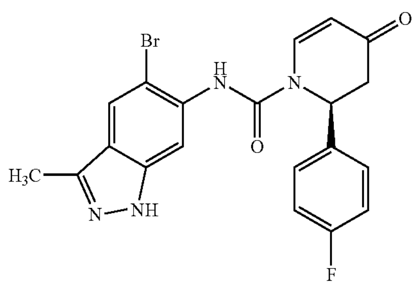 | (S)-2-(4-Fluoro-phenyl)-4-oxo-3,4-dihydro-2H-pyridine-1-carboxylic acid (5-bromo-3-methyl-1H-indazol-6-yl)-amide | 444 | 6.905 |
| 37 | 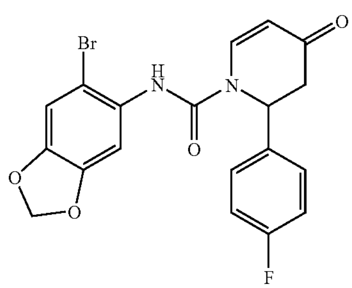 | 2-(4-Fluoro-phenyl)-4-oxo-3,4-dihydro-2H-pyridine-1-carboxylic acid (6-bromo-benzo[1,3]dioxol-5-yl)-amide | 434 | 7.456667 |
| 38 | 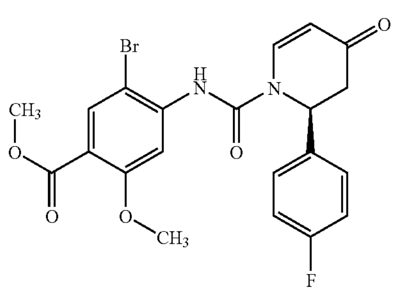 | 5-Bromo-4-{[(S)-2-(4-fluoro-phenyl)-4-oxo-3,4-dihydro-2H-pyridine-1-carbonyl]-amino}-2-methoxy-benzoic acid methyl ester | 478 | 6.89 |
| 39 | 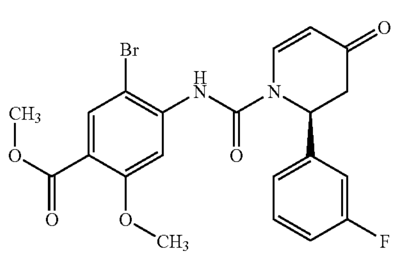 | 5-Bromo-4-{[(S)-2-(3-fluoro-phenyl)-4-oxo-3,4-dihydro-2H-pyridine-1-carbonyl]-amino}-2-methoxy-benzoic acid methyl ester | 158.8-161.8° C. | 7.06 |

TABLE 1-continued

| # | Structure | Name | M + H/MP | pIC$_{50}$ |
|---|---|---|---|---|
| 40 | 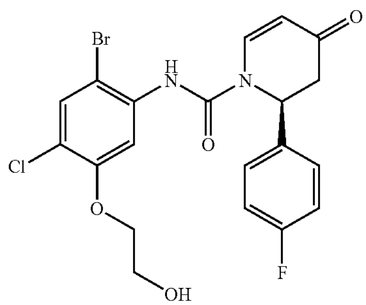 | (S)-2-(4-Fluoro-phenyl)-4-oxo-3,4-dihydro-2H-pyridine-1-carboxylic acid [2-bromo-4-chloro-5-(2-hydroxy-ethoxy)-phenyl]-amide | 484 | 7.606667 |
| 41 | 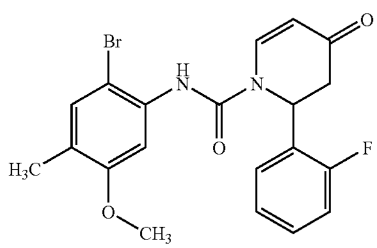 | 2-(2-Fluoro-phenyl)-4-oxo-3,4-dihydro-2H-pyridine-1-carboxylic acid (2-bromo-5-methoxy-4-methyl-phenyl)-amide | 434 | 6.43 |
| 42 | 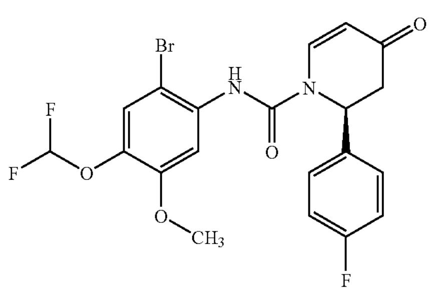 | (S)-2-(4-Fluoro-phenyl)-4-oxo-3,4-dihydro-2H-pyridine-1-carboxylic acid (2-bromo-4-difluoromethoxy-5-methoxy-phenyl)-amide | 486 | 7.503333 |
| 43 | 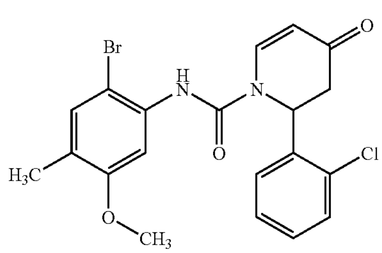 | 2-(2-Chloro-phenyl)-4-oxo-3,4-dihydro-2H-pyridine-1-carboxylic acid (2-bromo-5-methoxy-4-methyl-phenyl)-amide | 450 | |
| 44 | 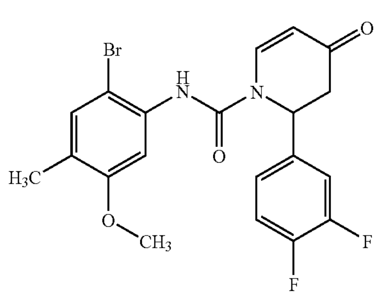 | 2-(3,4-Difluoro-phenyl)-4-oxo-3,4-dihydro-2H-pyridine-1-carboxylic acid (2-bromo-5-methoxy-4-methyl-phenyl)-amide | 452 | 7.383333 |

TABLE 1-continued

| # | Structure | Name | M + H/MP | pIC$_{50}$ |
|---|---|---|---|---|
| 45 | 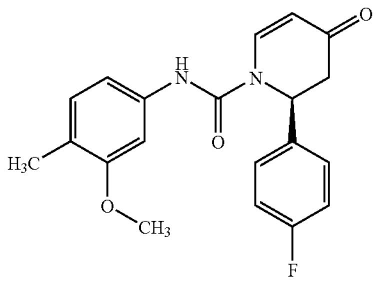 | (S)-2-(4-Fluoro-phenyl)-4-oxo-3,4-dihydro-2H-pyridine-1-carboxylic acid (3-methoxy-4-methyl-phenyl)-amide | 355 | 6.736667 |
| 46 | 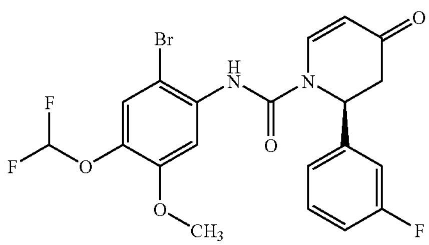 | (S)-2-(3-Fluoro-phenyl)-4-oxo-3,4-dihydro-2H-pyridine-1-carboxylic acid (2-bromo-4-difluoromethoxy-5-methoxy-phenyl)-amide | 486 | 7.293333 |
| 47 | 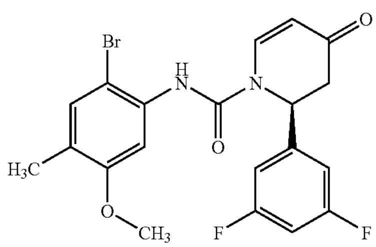 | 2-(3,5-Difluoro-phenyl)-4-oxo-3,4-dihydro-2H-pyridine-1-carboxylic acid (2-bromo-5-methoxy-4-methyl-phenyl)-amide | 452 | 6.986667 |
| 48 | 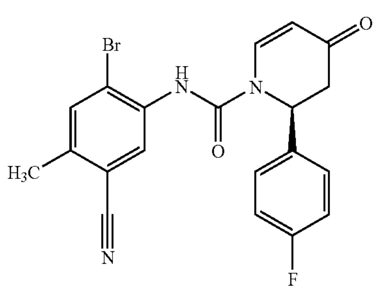 | (S)-2-(4-Fluoro-phenyl)-4-oxo-3,4-dihydro-2H-pyridine-1-carboxylic acid (2-bromo-5-cyano-4-methyl-phenyl)-amide | 429 | 6.84 |
| 49 | 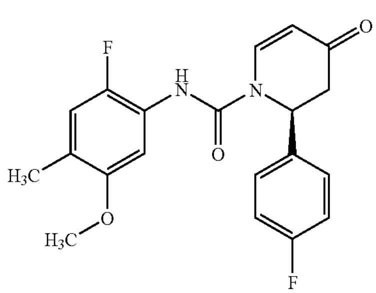 | (S)-2-(4-Fluoro-phenyl)-4-oxo-3,4-dihydro-2H-pyridine-1-carboxylic acid (2-fluoro-5-methoxy-4-methyl-phenyl)-amide | 373 | 7.21 |

TABLE 1-continued

| # | Structure | Name | M + H/MP | pIC$_{50}$ |
|---|---|---|---|---|
| 50 | 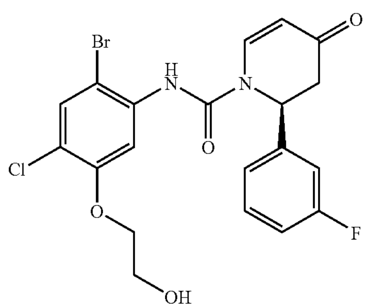 | (S)-2-(3-Fluoro-phenyl)-4-oxo-3,4-dihydro-2H-pyridine-1-carboxylic acid [2-bromo-4-chloro-5-(2-hydroxy-ethoxy)-phenyl]-amide | 484 | 7.406667 |
| 51 | 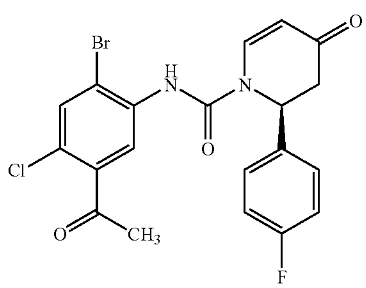 | (S)-2-(4-Fluoro-phenyl)-4-oxo-3,4-dihydro-2H-pyridine-1-carboxylic acid (5-acetyl-2-bromo-4-chloro-phenyl)-amide | 466 | 6.856667 |
| 52 | 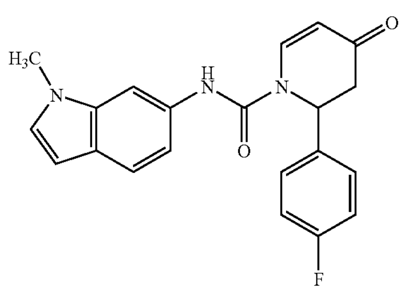 | 2-(4-Fluoro-phenyl)-4-oxo-3,4-dihydro-2H-pyridine-1-carboxylic acid (1-methyl-1H-indol-6-yl)-amide | 368 | 7.065 |
| 53 | 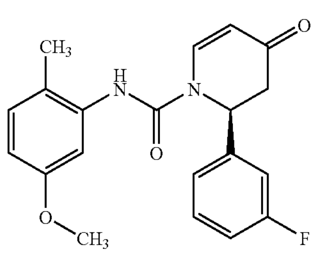 | (S)-2-(3-Fluoro-phenyl)-4-oxo-3,4-dihydro-2H-pyridine-1-carboxylic acid (5-methoxy-2-methyl-phenyl)-amide | 355 | 8.01 |
| 54 | 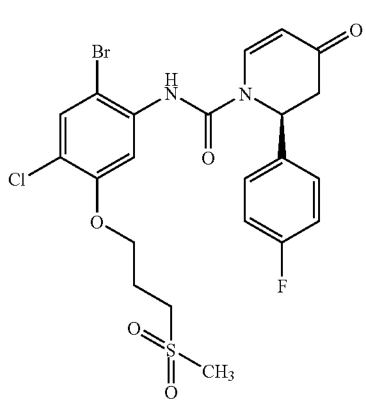 | (S)-2-(4-Fluoro-phenyl)-4-oxo-3,4-dihydro-2H-pyridine-1-carboxylic acid [2-bromo-4-chloro-5-(3-methanesulfonyl-propoxy)-phenyl]-amide | 560 | 6.38 |

TABLE 1-continued

| # | Structure | Name | M + H/MP | pIC$_{50}$ |
|---|---|---|---|---|
| 55 | 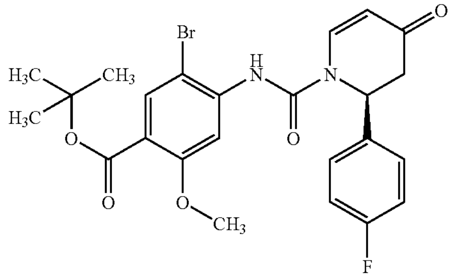 | 5-Bromo-4-{[(S)-2-(4-fluoro-phenyl)-4-oxo-3,4-dihydro-2H-pyridine-1-carbonyl]-amino}-2-methoxy-benzoic acid tert-butyl ester | 520 | 5.845 |
| 56 | 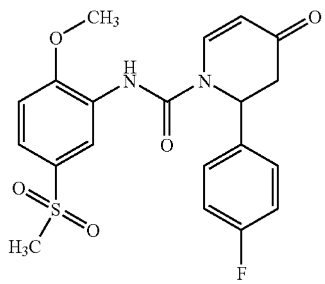 | 2-(4-Fluoro-phenyl)-4-oxo-3,4-dihydro-2H-pyridine-1-carboxylic acid (5-methanesulfonyl-2-methoxy-phenyl)-amide | 181.0-183.0° C. | 5.11 |
| 57 | 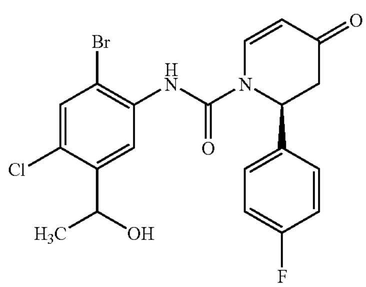 | (S)-2-(4-Fluoro-phenyl)-4-oxo-3,4-dihydro-2H-pyridine-1-carboxylic acid [2-bromo-4-chloro-5-(1-hydroxy-ethyl)-phenyl]-amide | 468 | 7.42 |
| 58 | 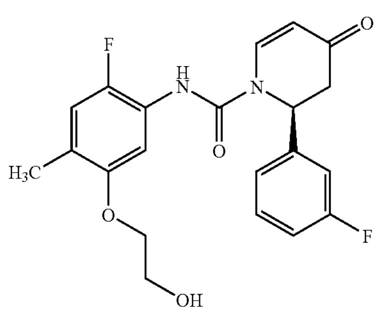 | (S)-2-(3-Fluoro-phenyl)-4-oxo-3,4-dihydro-2H-pyridine-1-carboxylic acid [2-fluoro-5-(2-hydroxy-ethoxy)-4-methyl-phenyl]-amide | 403 | 6.43 |
| 59 | 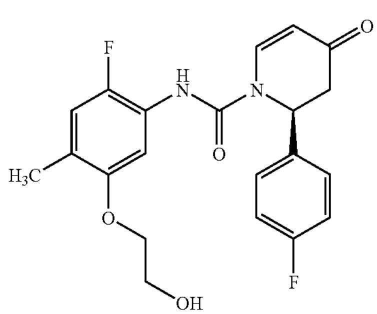 | (S)-2-(4-Fluoro-phenyl)-4-oxo-3,4-dihydro-2H-pyridine-1-carboxylic acid [2-fluoro-5-(2-hydroxy-ethoxy)-4-methyl-phenyl]-amide | 403 | 6.62 |

TABLE 1-continued

| # | Name | M + H/MP | pIC$_{50}$ |
|---|---|---|---|
| 60 | (S)-2-(4-Fluoro-phenyl)-4-oxo-3,4-dihydro-2H-pyridine-1-carboxylic acid (2-bromo-4-carbamoyl-5-methoxy-phenyl)-amide | 463 | 5.78 |
| 61 | (S)-2-(4-Fluoro-phenyl)-4-oxo-3,4-dihydro-2H-pyridine-1-carboxylic acid (6-bromo-2,2-difluoro-benzo[1,3]dioxol-5-yl)-amide | 470 | 6.365 |
| 62 | 2-(4-Fluoro-phenyl)-4-oxo-3,4-dihydro-2H-pyridine-1-carboxylic acid (2,6-difluoro-phenyl)-amide | 347 | 5.51 |
| 63 | (S)-2-(4-Fluoro-phenyl)-4-oxo-3,4-dihydro-2H-pyridine-1-carboxylic acid (2-bromo-4-cyano-5-methoxy-phenyl)-amide | 445 | 6.74 |
| 64 | 2-(4-Fluoro-phenyl)-4-oxo-3,4-dihydro-2H-pyridine-1-carboxylic acid adamantan-1-ylamide | 369 | 5.98 |

TABLE 1-continued

| # | Structure | Name | M + H/MP | pIC$_{50}$ |
|---|---|---|---|---|
| 65 | 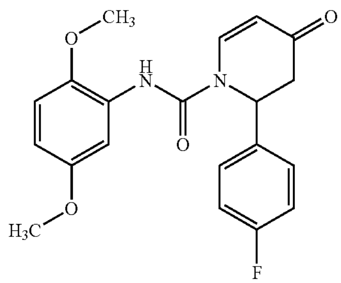 | 2-(4-Fluoro-phenyl)-4-oxo-3,4-dihydro-2H-pyridine-1-carboxylic acid (2,5-dimethoxy-phenyl)-amide | 371 | 6.23 |
| 66 | 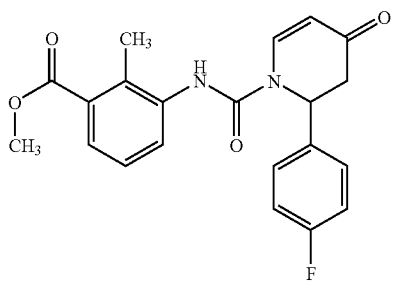 | 3-{[2-(4-Fluoro-phenyl)-4-oxo-3,4-dihydro-2H-pyridine-1-carbonyl]-amino}-2-methyl benzoic acid methyl ester | | 6.8 |
| 67 | 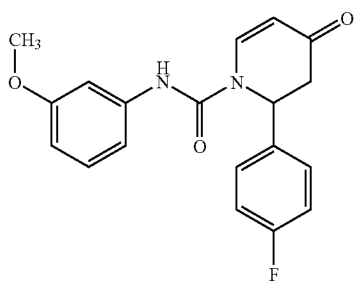 | 2-(4-Fluoro-phenyl)-4-oxo-3,4-dihydro-2H-pyridine-1-carboxylic acid (3-methoxy-phenyl)-amide | | 6.31 |
| 68 | 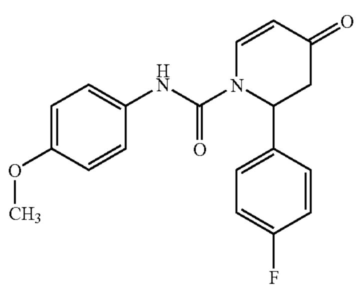 | 2-(4-Fluoro-phenyl)-4-oxo-3,4-dihydro-2H-pyridine-1-carboxylic acid (4-methoxy-phenyl)-amide | | 5.62 |
| 69 | 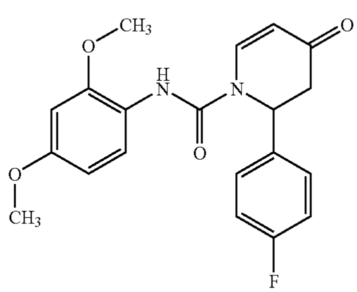 | 2-(4-Fluoro-phenyl)-4-oxo-3,4-dihydro-2H-pyridine-1-carboxylic acid (2,4-dimethoxy-phenyl)-amide | | 6.07 |

TABLE 1-continued

| # | Structure | Name | M + H/MP | pIC$_{50}$ |
|---|---|---|---|---|
| 70 | 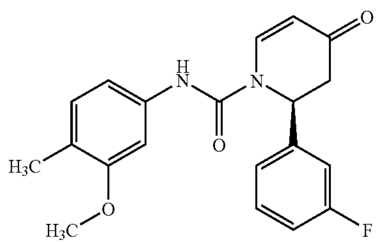 | (S)-2-(3-Fluoro-phenyl)-4-oxo-3,4-dihydro-2H-pyridine-1-carboxylic acid (3-methoxy-4-methyl-phenyl)-amide | | 6.84 |
| 71 | 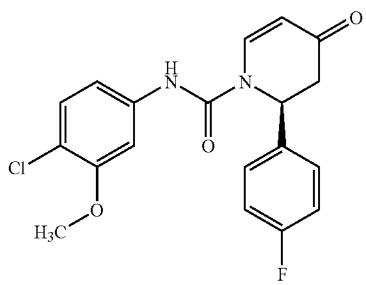 | (S)-2-(4-Fluoro-phenyl)-4-oxo-3,4-dihydro-2H-pyridine-1-carboxylic acid (4-chloro-3-methoxy-phenyl)-amide | | 6.245 |
| 72 | 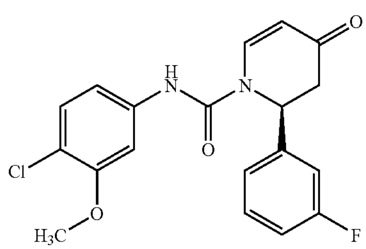 | (S)-2-(3-Fluoro-phenyl)-4-oxo-3,4-dihydro-2H-pyridine-1-carboxylic acid (4-chloro-3-methoxy-phenyl)-amide | | 6.295 |
| 73 | 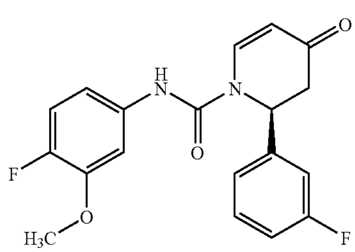 | (S)-2-(3-Fluoro-phenyl)-4-oxo-3,4-dihydro-2H-pyridine-1-carboxylic acid (4-fluoro-3-methoxy-phenyl)-amide | | 6.83 |
| 74 | 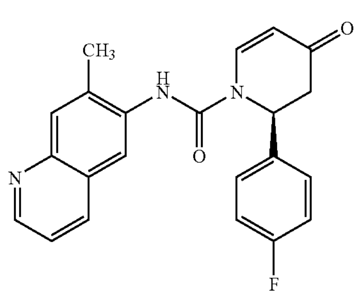 | (S)-2-(4-Fluoro-phenyl)-4-oxo-3,4-dihydro-2H-pyridine-1-carboxylic acid (7-methyl-quinolin-6-yl)-amide | | 7.35 |

| # | Structure | Name | M + H/MP | pIC₅₀ |
|---|---|---|---|---|
| 75 | 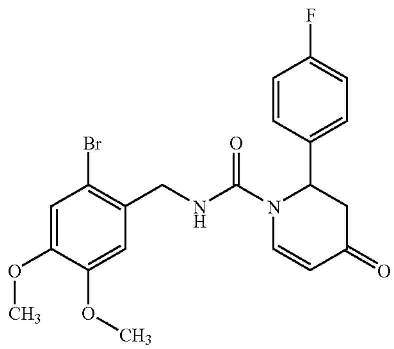 | 2-(4-Fluoro-phenyl)-4-oxo-3,4-dihydro-2H-pyridine-1-carboxylic acid 2-bromo-4,5-dimethoxy-benzylamide | | 5.075 |
| 76 | 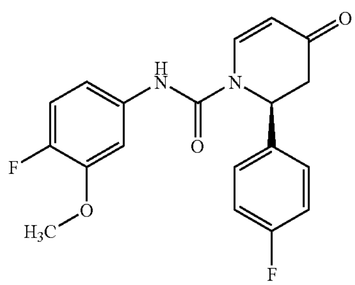 | (S)-2-(4-Fluoro-phenyl)-4-oxo-3,4-dihydro-2H-pyridine-1-carboxylic acid (4-fluoro-3-methoxy-phenyl)-amide | | 6.76 |
| 77 | 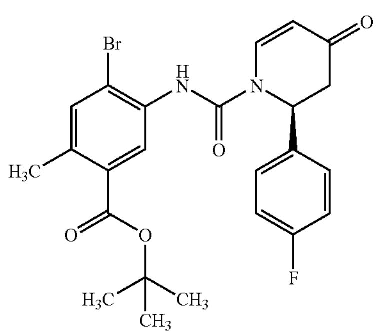 | 4-Bromo-5-{[(S)-2-(4-fluoro-phenyl)-4-oxo-3,4-dihydro-2H-pyridine-1-carbonyl]amino}-2-methyl-benzoic acid tert-butyl ester | | 6.67 |
| 78 | 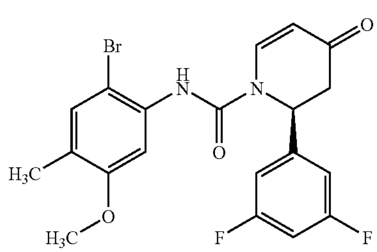 | (S)-2-(3,5-Difluoro-phenyl)-4-oxo-3,4-dihydro-2H-pyridine-1-carboxylic acid (2-bromo-5-methoxy-4-methyl-phenyl)-amide | | 7.675 |
| 79 | 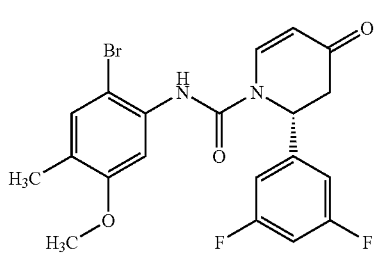 | (R)-2-(3,5-Difluoro-phenyl)-4-oxo-3,4-dihydro-2H-pyridine-1-carboxylic acid (2-bromo-5-methoxy-4-methyl-phenyl)-amide | | 5.475 |

TABLE 1-continued

| # | Structure | Name | M + H/MP | pIC$_{50}$ |
|---|---|---|---|---|
| 80 | 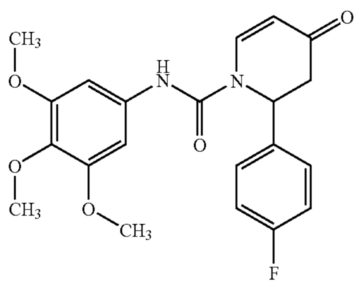 | 2-(4-Fluoro-phenyl)-4-oxo-3,4-dihydro-2H-pyridine-1-carboxylic acid (3,4,5-trimethoxy-phenyl)-amide | | 5 |
| 81 | 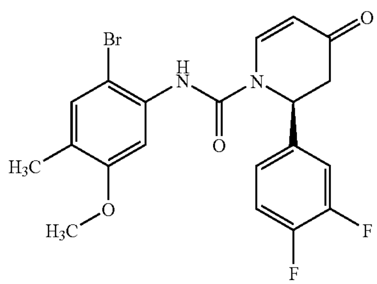 | (S)-2-(3,4-Difluoro-phenyl)-4-oxo-3,4-dihydro-2H-pyridine-1-carboxylic acid (2-bromo-5-methoxy-4-methyl-phenyl)-amide | | 7.54 |
| 82 | 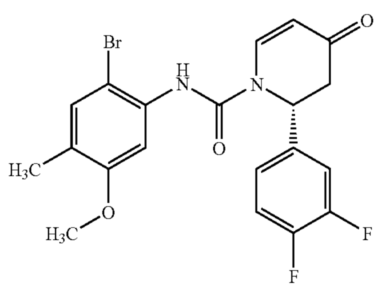 | (R)-2-(3,4-Difluoro-phenyl)-4-oxo-3,4-dihydro-2H-pyridine-1-carboxylic acid (2-bromo-5-methoxy-4-methyl-phenyl)-amide | | 5.31 |
| 83 | 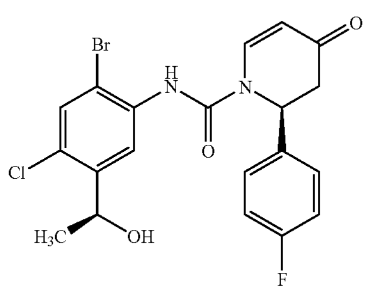 | (S)-2-(4-Fluoro-phenyl)-4-oxo-3,4-dihydro-2H-pyridine-1-carboxylic acid [2-bromo-4-chloro-5-((S)-1-hydroxy-ethyl)-phenyl]-amide | | 7.56 |
| 84 | 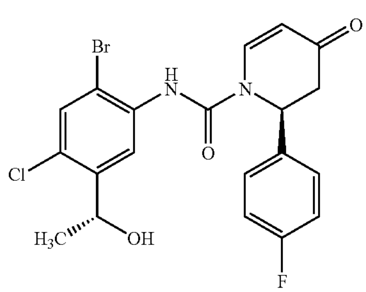 | (S)-2-(4-Fluoro-phenyl)-4-oxo-3,4-dihydro-2H-pyridine-1-carboxylic acid [2-bromo-4-chloro-5-((R)-1-hydroxy-ethyl)-phenyl]-amide | | 6.67 |

TABLE 1-continued

| # | Structure | Name | M + H/MP | pIC$_{50}$ |
|---|---|---|---|---|
| 85 | 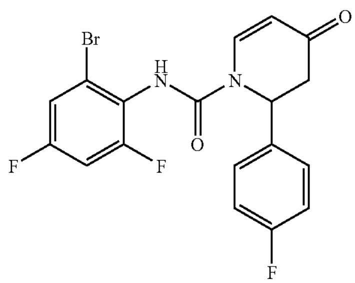 | 2-(4-Fluoro-phenyl)-4-oxo-3,4-dihydro-2H-pyridine-1-carboxylic acid (2-bromo-4,6-difluoro-phenyl)-amide | | 5 |
| 86 | 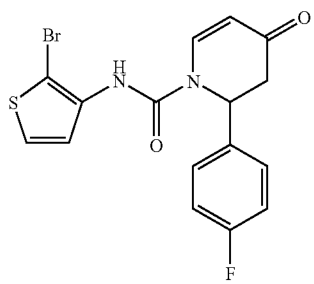 | 2-(4-Fluoro-phenyl)-4-oxo-3,4-dihydro-2H-pyridine-1-carboxylic acid (2-bromo-thiophen-3-yl)-amide | | 6.725 |
| 87 | 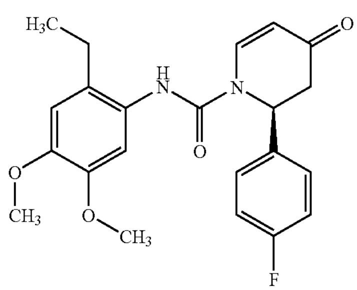 | (S)-2-(4-Fluoro-phenyl)-4-oxo-3,4-dihydro-2H-pyridine-1-carboxylic acid (2-ethyl-4,5-dimethoxy-phenyl)-amide | | 8.36 |
| 88 | 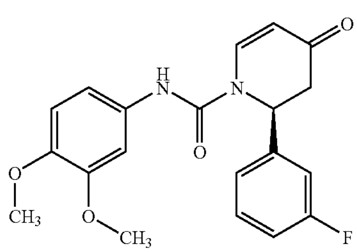 | (S)-2-(3-Fluoro-phenyl)-4-oxo-3,4-dihydro-2H-pyridine-1-carboxylic acid (3,4-dimethoxy-phenyl)-amide | | 6.32 |
| 89 | 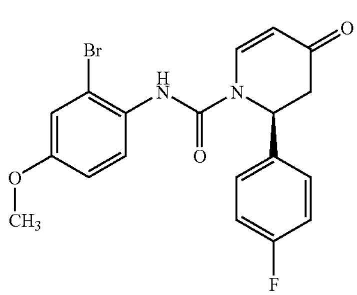 | (S)-2-(4-Fluoro-phenyl)-4-oxo-3,4-dihydro-2H-pyridine-1-carboxylic acid (2-bromo-4-methoxy-phenyl)-amide | | 7.45 |

TABLE 1-continued

| # | Structure | Name | M + H/MP | pIC$_{50}$ |
|---|---|---|---|---|
| 90 | 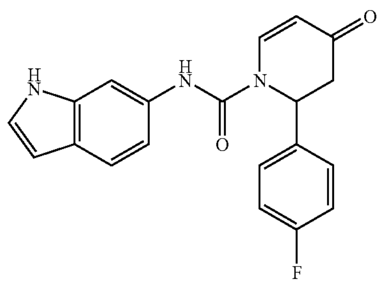 | 2-(4-Fluoro-phenyl)-4-oxo-3,4-dihydro-2H-pyridine-1-carboxylic acid (1H-indol-6-yl)-amide | | 6.615 |
| 91 | 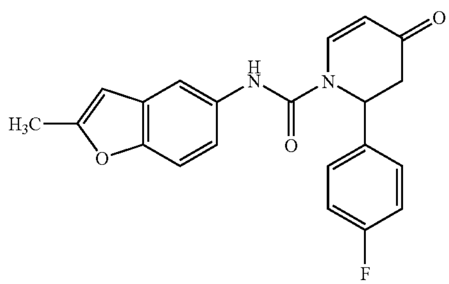 | 2-(4-Fluoro-phenyl)-4-oxo-3,4-dihydro-2H-pyridine-1-carboxylic acid (2-methyl-benzofuran-5-yl)-amide | | 6.315 |
| 92 | 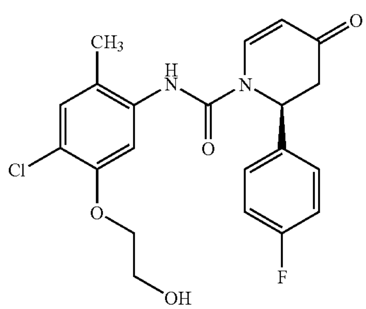 | (S)-2-(4-Fluoro-phenyl)-4-oxo-3,4-dihydro-2H-pyridine-1-carboxylic acid [4-chloro-5-(2-hydroxy-ethoxy)-2-methyl-phenyl]-amide | | 8.023333 |
| 93 | 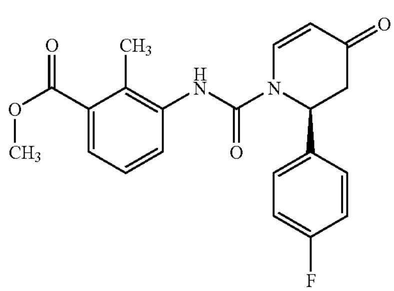 | 3-{[(S)-2-(4-Fluoro-phenyl)-4-oxo-3,4-dihydro-2H-pyridine-1-carbonyl]-amino}-2-methyl-benzoic acid methyl ester | | 7.44 |
| 94 | 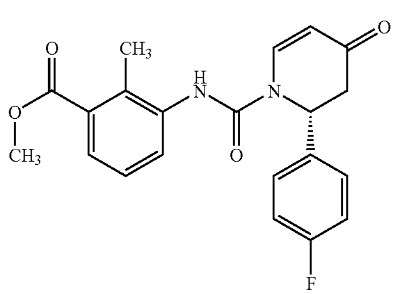 | 3-{[(R)-2-(4-Fluoro-phenyl)-4-oxo-3,4-dihydro-2H-pyridine-1-carbonyl]-amino}-2-methyl-benzoic acid methyl ester | | 6.13 |

TABLE 1-continued

| # | Structure | Name | M + H/MP | pIC$_{50}$ |
|---|---|---|---|---|
| 95 | 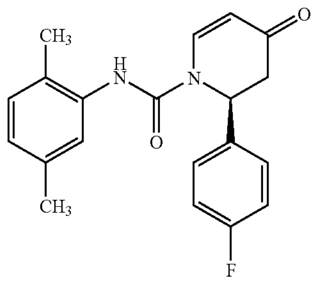 | (S)-2-(4-Fluoro-phenyl)-4-oxo-3,4-dihydro-2H-pyridine-1-carboxylic acid (2,5-dimethyl-phenyl)-amide | | 7.9775 |
| 96 | 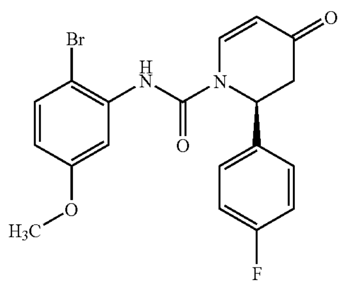 | (S)-2-(4-Fluoro-phenyl)-4-oxo-3,4-dihydro-2H-pyridine-1-carboxylic acid (2-bromo-5-methoxy-phenyl)-amide | | 7.875 |
| 97 | 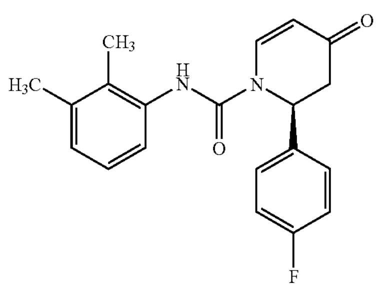 | (S)-2-(4-Fluoro-phenyl)-4-oxo-3,4-dihydro-2H-pyridine-1-carboxylic acid (2,3-dimethyl-phenyl)-amide | | 7.74 |
| 98 | 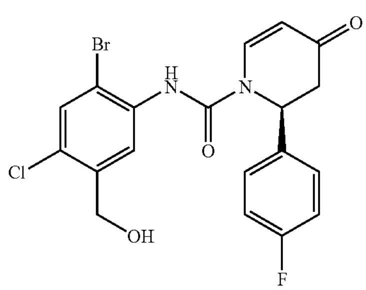 | (S)-2-(4-Fluoro-phenyl)-4-oxo-3,4-dihydro-2H-pyridine-1-carboxylic acid (2-bromo-4-chloro-5-hydroxymethyl-phenyl)-amide | | 7.475 |
| 99 | 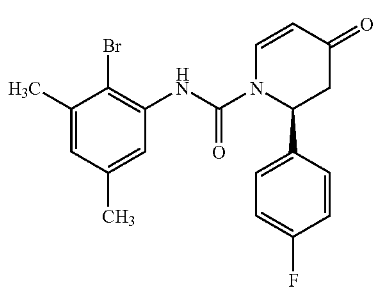 | (S)-2-(4-Fluoro-phenyl)-4-oxo-3,4-dihydro-2H-pyridine-1-carboxylic acid (2-bromo-3,5-dimethyl-phenyl)-amide | | 7.98 |

| # | Structure | Name | M + H/MP | pIC₅₀ |
|---|---|---|---|---|
| 100 | 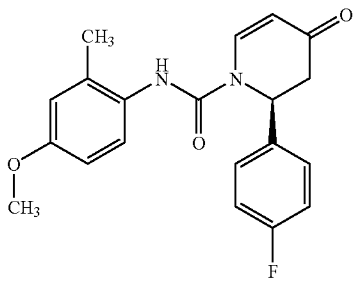 | (S)-2-(4-Fluoro-phenyl)-4-oxo-3,4-dihydro-2H-pyridine-1-carboxylic acid (4-methoxy-2-methyl-phenyl)-amide | | 7.05 |
| 101 | 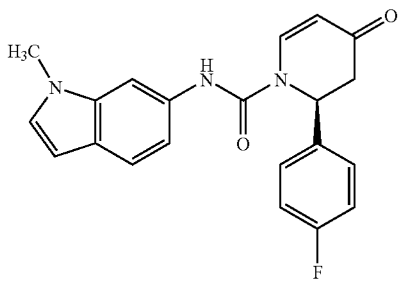 | (S)-2-(4-Fluoro-phenyl)-4-oxo-3,4-dihydro-2H-pyridine-1-carboxylic acid (1-methyl-1H-indol-6-yl)-amide | | 7.57 |
| 102 | 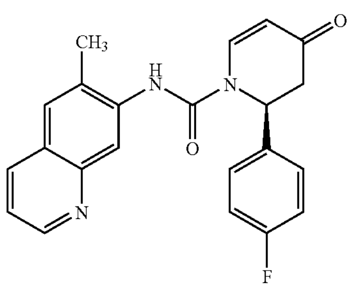 | (S)-2-(4-Fluoro-phenyl)-4-oxo-3,4-dihydro-2H-pyridine-1-carboxylic acid (6-methyl-quinolin-7-yl)-amide | | 6.56 |
| 103 | 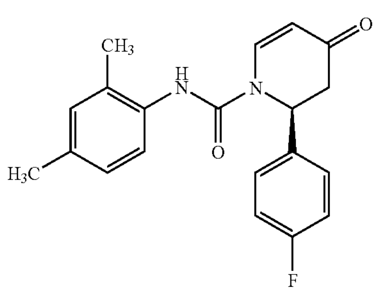 | (S)-2-(4-Fluoro-phenyl)-4-oxo-3,4-dihydro-2H-pyridine-1-carboxylic acid (2,4-dimethyl-phenyl)-amide | | 7.415 |
| 104 | 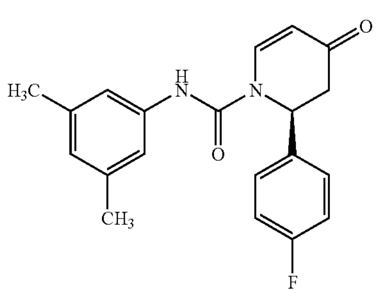 | (S)-2-(4-Fluoro-phenyl)-4-oxo-3,4-dihydro-2H-pyridine-1-carboxylic acid (3,5-dimethyl-phenyl)-amide | | 7.655 |

TABLE 1-continued

| # | Structure | Name | M + H/MP | pIC$_{50}$ |
|---|---|---|---|---|
| 105 | 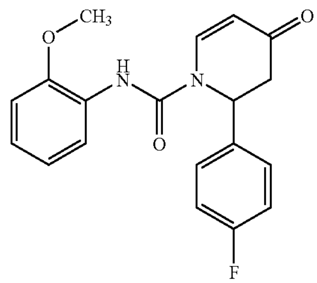 | 2-(4-Fluoro-phenyl)-4-oxo-3,4-dihydro-2H-pyridine-1-carboxylic acid (2-methoxy-phenyl)-amide | | 5.91 |
| 106 | 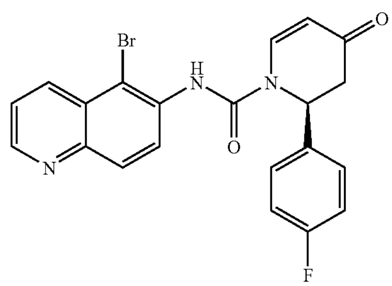 | (S)-2-(4-Fluoro-phenyl)-4-oxo-3,4-dihydro-2H-pyridine-1-carboxylic acid (5-bromo-quinolin-6-yl)-amide | | 7.785 |
| 107 | 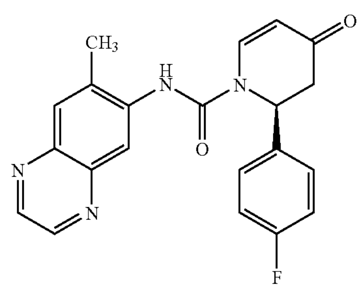 | (S)-2-(4-Fluoro-phenyl)-4-oxo-3,4-dihydro-2H-pyridine-1-carboxylic acid (7-methyl-quinoxalin-6-yl)-amide | | 7.095 |
| 108 | 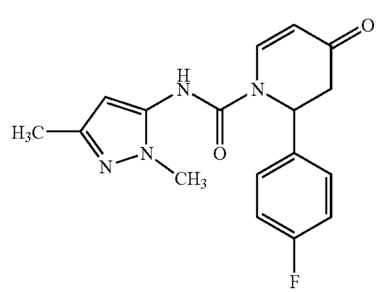 | 2-(4-Fluoro-phenyl)-4-oxo-3,4-dihydro-2H-pyridine-1-carboxylic acid (2,5-dimethyl-2H-pyrazol-3-yl)-amide | | 6.043 |
| 109 | 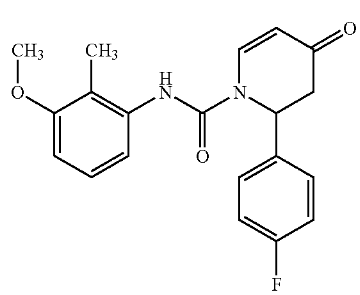 | 2-(4-Fluoro-phenyl)-4-oxo-3,4-dihydro-2H-pyridine-1-carboxylic acid (3-methoxy-2-methyl-phenyl)-amide | | 8.433 |

TABLE 1-continued

| # | Structure | Name | M + H/MP | pIC$_{50}$ |
|---|---|---|---|---|
| 110 | 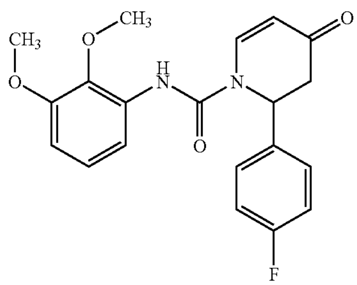 | 2-(4-Fluoro-phenyl)-4-oxo-3,4-dihydro-2H-pyridine-1-carboxylic acid (2,3-dimethoxy-phenyl)-amide | | 6.89 |
| 111 | 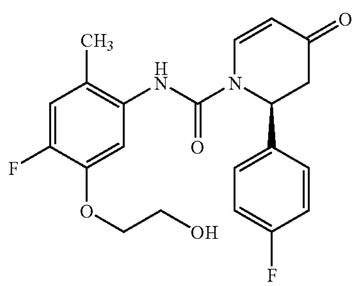 | (S)-2-(4-Fluoro-phenyl)-4-oxo-3,4-dihydro-2H-pyridine-1-carboxylic acid [4-fluoro-5-(2-hydroxy-ethoxy)-2-methyl-phenyl]-amide | | 8.12 |
| 112 | 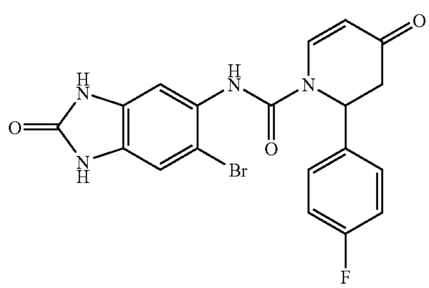 | 2-(4-Fluoro-phenyl)-4-oxo-3,4-dihydro-2H-pyridine-1-carboxylic acid (6-bromo-2-oxo-2,3-dihydro-1H-benzoimidazol-5-yl)-amide | | 5.93 |
| 113 | 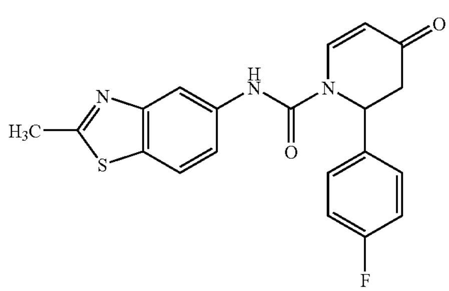 | 2-(4-Fluoro-phenyl)-4-oxo-3,4-dihydro-2H-pyridine-1-carboxylic acid (2-methyl-benzothiazol-5-yl)-amide | | 5.505 |
| 114 | 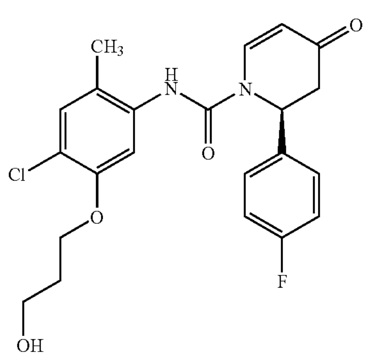 | (S)-2-(4-Fluoro-phenyl)-4-oxo-3,4-dihydro-2H-pyridine-1-carboxylic acid [4-chloro-5-(3-hydroxy-propoxy)-2-methyl-phenyl]-amide | | 7.74 |

TABLE 1-continued

| # | Structure | Name | M + H/MP | pIC$_{50}$ |
|---|---|---|---|---|
| 115 | 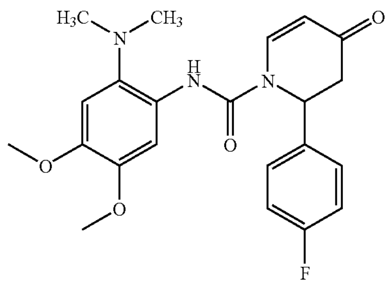 | 2-(4-Fluoro-phenyl)-4-oxo-3,4-dihydro-2H-pyridine-1-carboxylic acid (2-dimethylamino-4,5-dimethoxy-phenyl)-amide | | 5.915 |
| 116 | 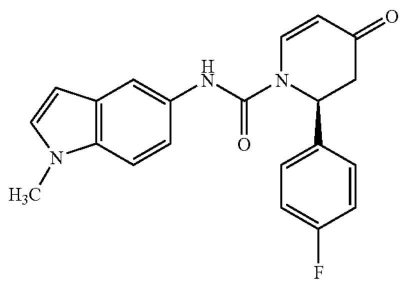 | (S)-2-(4-Fluoro-phenyl)-4-oxo-3,4-dihydro-2H-pyridine-1-carboxylic acid (1-methyl-1H-indol-5-yl)-amide | | 7.405 |
| 117 | 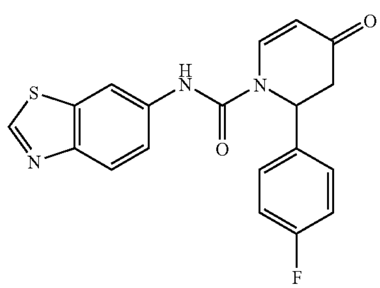 | 2-(4-Fluoro-phenyl)-4-oxo-3,4-dihydro-2H-pyridine-1-carboxylic acid benzothiazol-6-ylamide | | 6.31 |
| 118 | 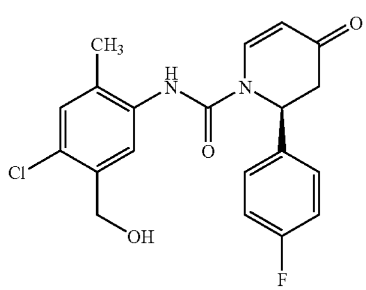 | (S)-2-(4-Fluoro-phenyl)-4-oxo-3,4-dihydro-2H-pyridine-1-carboxylic acid (4-chloro-5-hydroxymethyl-2-methyl-phenyl)-amide | | 7.735 |
| 119 | 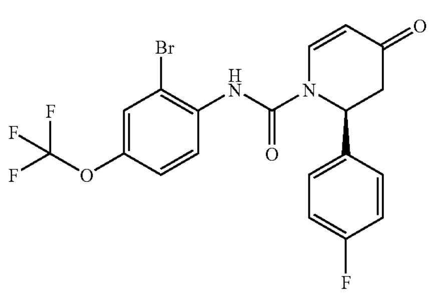 | (S)-2-(4-Fluoro-phenyl)-4-oxo-3,4-dihydro-2H-pyridine-1-carboxylic acid 92-bromo-4-trifluoromethoxy-phenyl)-amide | | 6.175 |

TABLE 1-continued

| # | Structure | Name | M + H/MP | pIC$_{50}$ |
|---|---|---|---|---|
| 120 | 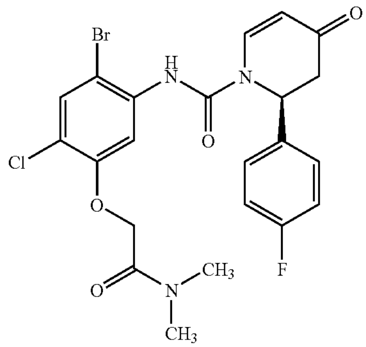 | (S)-2-(4-Fluoro-phenyl)-4-oxo-3,4-dihydro-2H-pyridine-1-carboxylic acid (2-bromo-4-chloro-5-dimethylcarbamoylmethoxy-phenyl)-amide | | 6.95 |
| 121 | 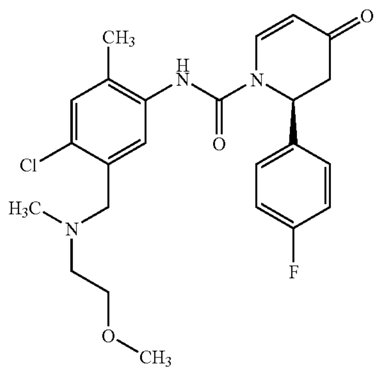 | (S)-2-(4-Fluoro-phenyl)-4-oxo-3,4-dihydro-2H-pyridine-1-carboxylic acid (4-chloro-5-{[(2-methoxy-ethyl)-methyl-amino]-methyl}-2-methyl-phenyl)-amide | | 6.43 |
| 122 | 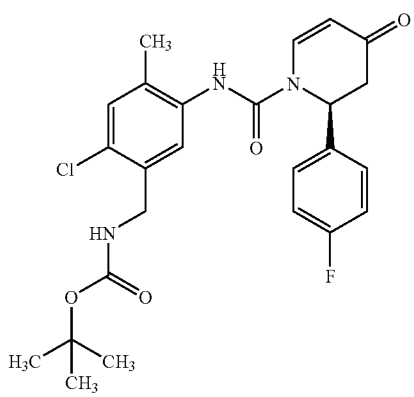 | (2-Chloro-5-{[(S)-2-(4-fluoro-phenyl)-4-oxo-3,4-dihydro-2H-pyridine-1-carbonyl]-amino}-4-methyl-benzyl)-carbamic acid tert-butyl ester | | 5.995 |
| 123 | 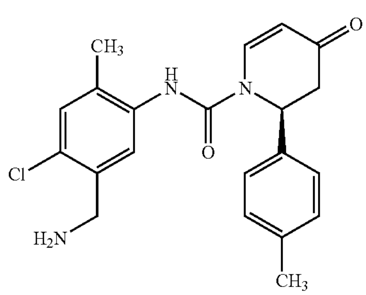 | (S)-2-(4-Fluoro-phenyl)-4-oxo-3,4-dihydro-2H-pyridine-1-carboxylic acid (5-aminomethyl-4-chloro-2-methyl-phenyl)-amide; te: replace with real name | | 6.07 |

TABLE 1-continued

| # | Structure | Name | M + H/MP | pIC$_{50}$ |
|---|---|---|---|---|
| 124 | 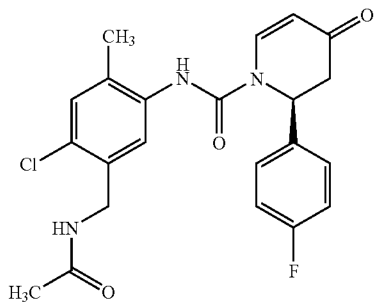 | (S)-2-(4-Fluoro-phenyl)-4-oxo-3,4-dihydro-2H-pyridine-1-carboxylic acid [5-(acetylamino-methyl)-4-chloro-2-methyl-phenyl]-amide | | 6.98 |
| 125 | 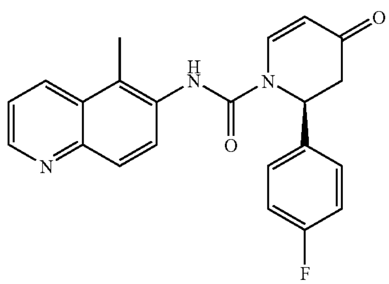 | (S)-2-(4-Fluoro-phenyl)-4-oxo-3,4-dihydro-2H-pyridine-1-carboxylic acid (5-methyl-quinolin-6-yl)-amide | | 7.16 |
| 126 | 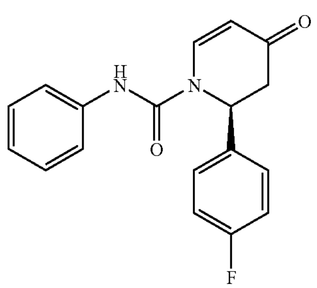 | (S)-2-(4-Fluoro-phenyl)-4-oxo-3,4-dihydro-2H-pyridine-1-carboxylic acid phenylamide | | 6.18 |
| 127 | 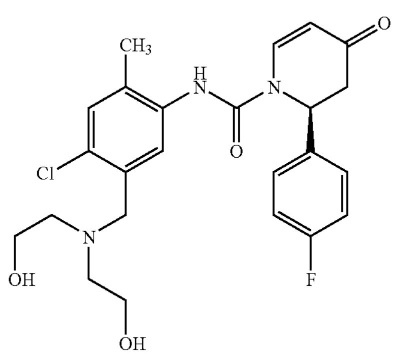 | (S)-2-(4-Fluoro-phenyl)-4-oxo-3,4-dihydro-2H-pyridine-1-carboxylic acid (5-{[bis(2-hydroxy-ethyl)-amino]-methyl}-4-chloro-2-methyl-phenyl)-amide | | 7.615 |
| 128 | 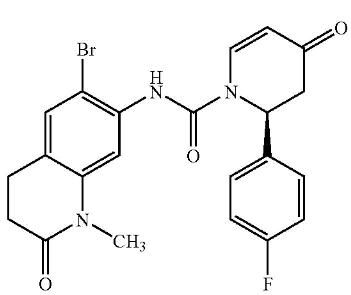 | (S)-2-(4-Fluoro-phenyl)-4-oxo-3,4-dihydro-2H-pyridine-1-carboxylic acid (6-bromo-1-methyl-2-oxo-1,2,3,4-tetrahydro-quinolin-7-yl)-amide | | 7.595 |

TABLE 1-continued

| # | Structure | Name | M + H/MP | pIC$_{50}$ |
|---|---|---|---|---|
| 129 | 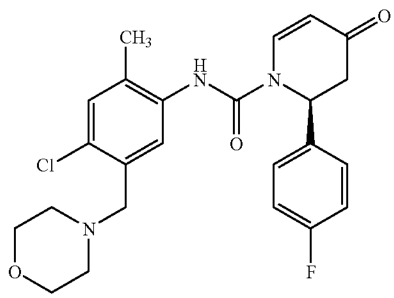 | (S)-2-(4-Fluoro-phenyl)-4-oxo-3,4-dihydro-2H-pyridine-1-carboxylic acid (4-chloro-2-methyl-5-morpholin-4-ylmethyl-phenyl)-amide | | 6.945 |
| 130 | 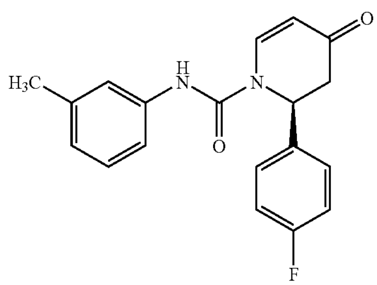 | (S)-2-(4-Fluoro-phenyl)-4-oxo-3,4-dihydro-2H-pyridine-1-carboxylic acid m-tolylamide | | 7.12 |
| 131 | 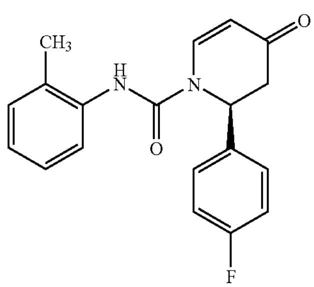 | (S)-2-(4-Fluoro-phenyl)-4-oxo-3,4-dihydro-2H-pyridine-1-carbxoylic acid o-tolylamide | | 7.53 |
| 132 | 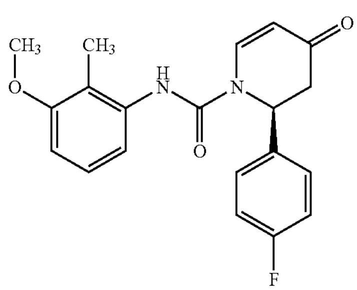 | (S)-2-(4-Fluoro-phenyl)-4-oxo-3,4-dihydro-2H-pyridine-1-carboxylic acid (3-methoxy-2-methyl-phenyl)-amide | | 8.57 |
| 133 | 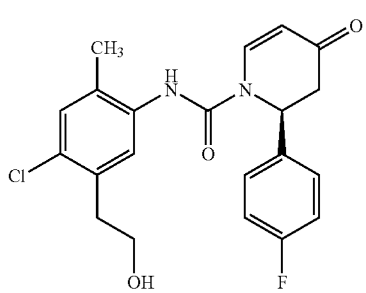 | (S)-2-(4-Fluoro-phenyl)-4-oxo-3,4-dihydro-2H-pyridine-1-carboxylic acid [4-chloro-5-(2-hydroxy-ethyl)-2-methyl-phenyl]-amide | | 8.06 |

TABLE 1-continued

| # | Structure | Name | M + H/MP | pIC$_{50}$ |
|---|---|---|---|---|
| 134 | 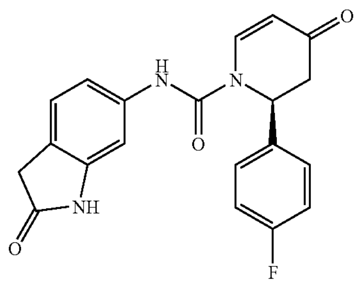 | (S)-2-(4-Fluoro-phenyl)-4-oxo-3,4-dihydro-2H-pyridine-1-carboxylic acid (2-oxo-2,3-dihydro-1H-indol-6-yl)-amide | | 5.385 |
| 135 | 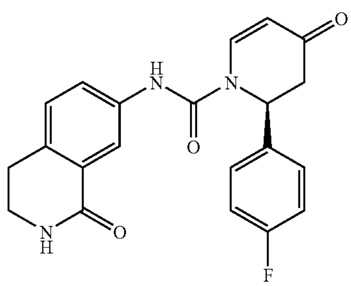 | (S)-2-(4-Fluoro-phenyl)-4-oxo-3,4-dihydro-2H-pyridine-1-carboxylic acid (1-oxo-1,2,3,4-tetrahydro-isoquinolin-7-yl)-amide | | |
| 136 | 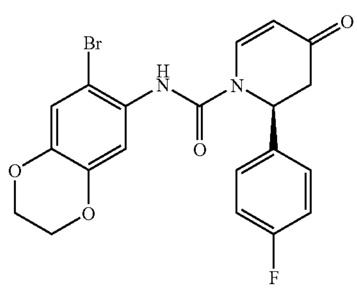 | (S)-2-(4-Fluoro-phenyl)-4-oxo-3,4-dihydro-2H-pyridine-1-carboxylic acid (7-bromo-2,3-dihydro-benzo[1,4]dioxin-6-yl)-amide | | 8.095 |
| 137 | 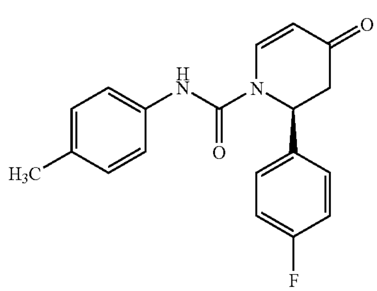 | (S)-2-(4-Fluoro-phenyl)-4-oxo-3,4-dihydro-2H-pyridine-1-carboxylic acid p-tolylamide | | 6.57 |
| 138 | 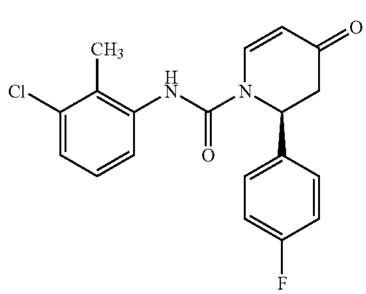 | (S)-2-(4-Fluoro-phenyl)-4-oxo-3,4-dihydro-2H-pyridine-1-carboxylic acid (3-chloro-2-methyl-phenyl)-amide | | 8.34 |

TABLE 1-continued

| # | Structure | Name | M + H/MP | pIC$_{50}$ |
|---|---|---|---|---|
| 139 | 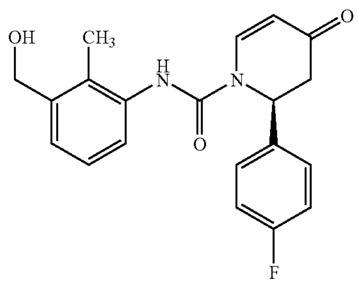 | (S)-2-(4-Fluoro-phenyl)-4-oxo-3,4-dihydro-2H-pyridine-1-carboxylic acid (3-hydroxymethyl-2-methyl-phenyl)-amide | | 7.79 |
| 140 | 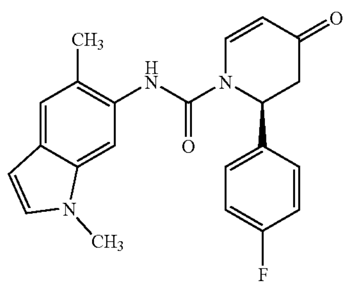 | (S)-2-(4-Fluoro-phenyl)-4-oxo-3,4-dihydro-2H-pyridine-1-carboxylic acid (1,5-dimethyl-1H-indol-6-yl)-amide | | 8.565 |
| 141 | 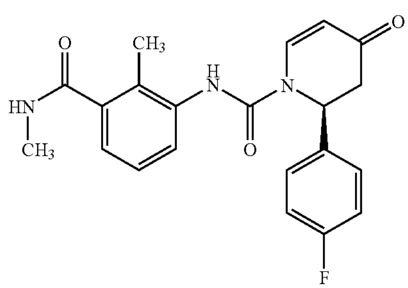 | (S)-2-(4-Fluoro-phenyl)-4-oxo-3,4-dihydro-2H-pyridine-1-carboxylic acid (2-methyl-3-methylcarbamoyl-phenyl)-amide | | 6.185 |
| 142 | 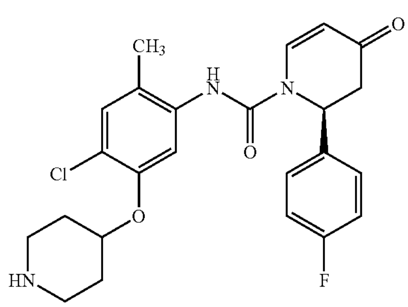 | (S)-2-(4-Fluoro-phenyl)-4-oxo-3,4-dihydro-2H-pyridine-1-carboxylic acid [4-chloro-2-methyl-5-(piperidin-4-yloxy)-phenyl]-amide | | 6.71 |
| 143 | 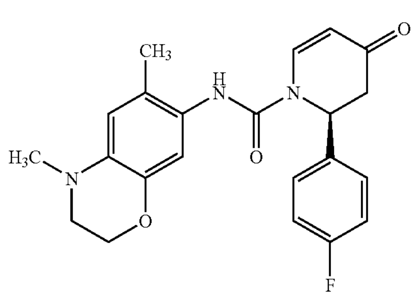 | (S)-2-(4-Fluoro-phenyl)-4-oxo-3,4-dihydro-2H-pyridine-1-carboxylic acid (4,6-dimethyl-3,4-dihydro-2H-benzo[1,4]oxazin-7-yl)-amide | | 7.825 |

TABLE 1-continued

| # | Structure | Name | M + H/MP | pIC$_{50}$ |
|---|---|---|---|---|
| 144 | 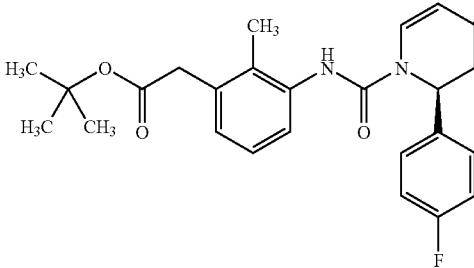 | (3-{[(S)-2-(4-Fluoro-phenyl)-4-oxo-3,4-dihydro-2H-pyridine-1-carbonyl]amino}-2-methyl-phenyl)-acetic acid tert-butyl ester | | 6.215 |
| 145 | 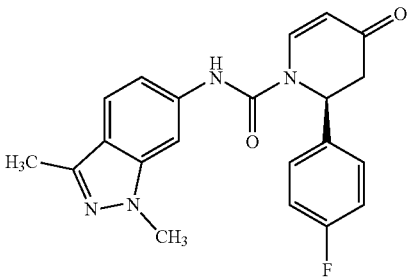 | (S)-2-(4-Fluoro-phenyl)-4-oxo-3,4-dihydro-2H-pyridine-1-carboxylic acid (1,3-dimethyl-1H-indazol-6-yl)-amide | | 6.535 |
| 146 | 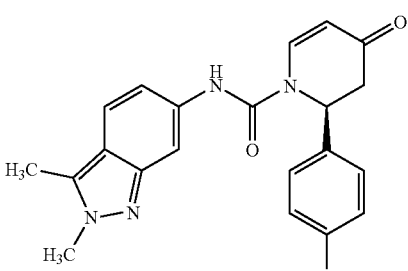 | (S)-2-(4-Fluoro-phenyl)-4-oxo-3,4-dihydro-2H-pyridine-1-carboxylic acid (2,3-dimethyl-2H-indazol-6-yl)-amide | | 5.615 |
| 147 | 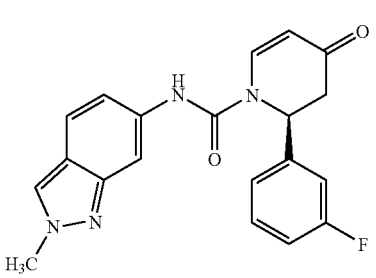 | (S)-2-(3-Fluoro-phenyl)-4-oxo-3,4-dihydro-2H-pyridine-1-carbxoylic acid (2-methyl-2H-indazol-6-yl)-amide | | 5.505 |
| 148 | 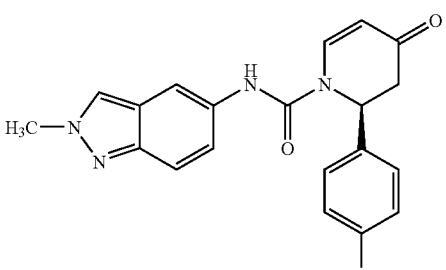 | (S)-2-(4-Fluoro-phenyl)-4-oxo-3,4-dihydro-2H-pyridine-1-carboxylic acid (2-methyl-2H-indazol-5-yl)-amide | | 6.87 |

TABLE 1-continued

| # | Structure | Name | M + H/MP | pIC$_{50}$ |
|---|---|---|---|---|
| 149 | 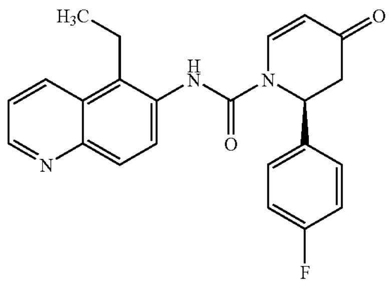 | (S)-2-(4-Fluoro-phenyl)-4-oxo-3,4-dihydro-2H-pyridine-1-carboxylic acid (5-ethyl-quinolin-6-yl)-amide | | 8.445 |
| 150 | 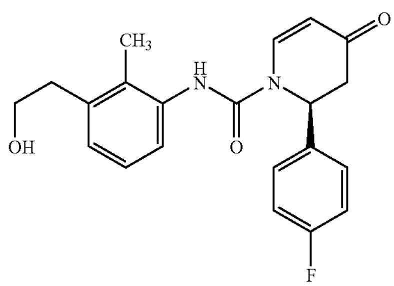 | (S)-2-(4-Fluoro-phenyl)-4-oxo-3,4-dihydro-2H-pyridine-1-carboxylic acid [3-(2-hydroxy-ethyl)-2-methyl-phenyl]-amide | | 7.835 |
| 151 | 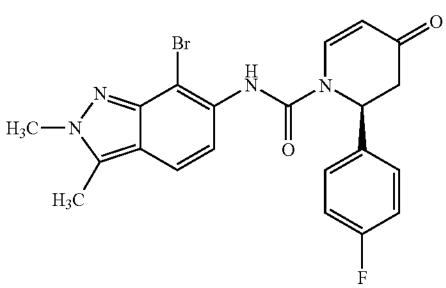 | (S)-2-(4-Fluoro-phenyl)-4-oxo-3,4-dihydro-2H-pyridine-1-carboxylic acid (7-bromo-2,3-dimethyl-2H-indazol-6-yl)-amide | | 5.975 |
| 152 | 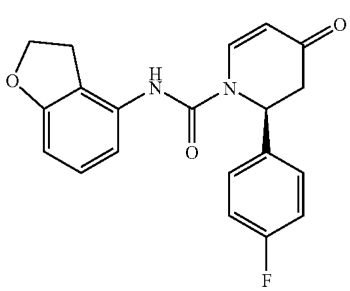 | (S)-2-(4-Fluoro-phenyl)-4-oxo-3,4-dihydro-2H-pyridine-1-carboxylic acid (2,3-dihydro-benzofuran-4-yl)-amide | | 7.355 |
| 153 | 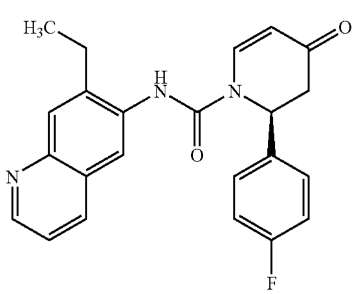 | (S)-2-(4-Fluoro-phenyl)-4-oxo-3,4-dihydro-2H-pyridine-1-carboxylic acid (7-ethyl-quinolin-6-yl)-amide | | 7.85 |

TABLE 1-continued

| # | Structure | Name | M + H/MP | pIC$_{50}$ |
|---|---|---|---|---|
| 154 | 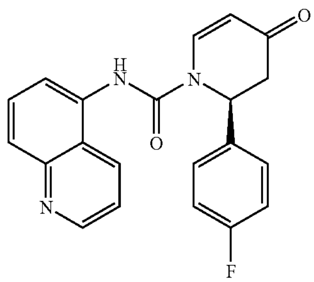 | (S)-2-(4-Fluoro-phenyl)-4-oxo-3,4-dihydro-2H-pyridine-1-carboxylic acid quinolin-5-ylamide | | 8.64 |
| 155 | 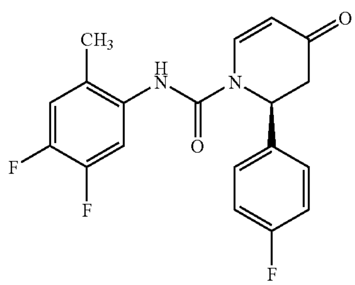 | (S)-2-(4-Fluoro-phenyl)-4-oxo-3,4-dihydro-2H-pyridine-1-carboxylic acid (4,5-difluoro-2-methyl-phenyl)-amide | | 7.12 |
| 156 | 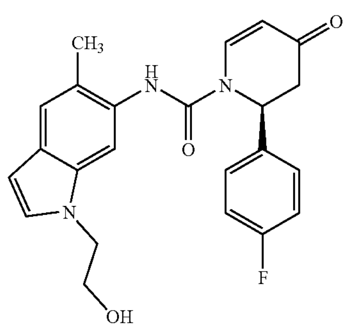 | (S)-2-(4-Fluoro-phenyl)-4-oxo-3,4-dihydro-2H-pyridine-1-carboxylic acid [1-(2-hydroxy-ethyl)-5-methyl-1H-indol-6-yl]-amide | | 8.155 |
| 157 | 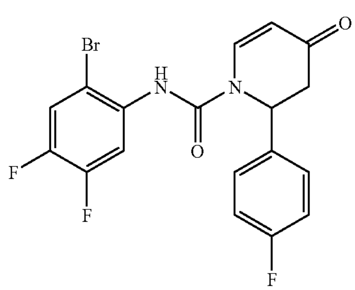 | 2-(4-Fluoro-phenyl)-4-oxo-3,4-dihydro-2H-pyridine-1-carboxylic acid (2-bromo-4,5-difluoro-phenyl)-amide | | 6.43 |
| 158 | 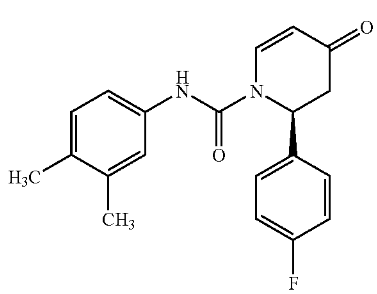 | (S)-2-(4-Fluoro-phenyl)-4-oxo-3,4-dihydro-2H-pyridine-1-carboxylic acid (3,4-dimethyl-phenyl)-amide | | 7.01 |

TABLE 1-continued

| # | Structure | Name | M + H/MP | pIC$_{50}$ |
|---|---|---|---|---|
| 159 | 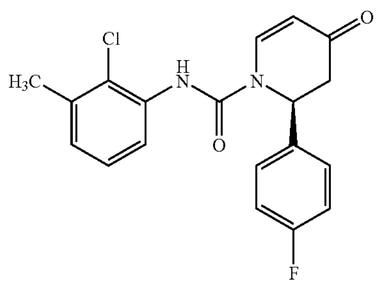 | (S)-2-(4-Fluoro-phenyl)-4-oxo-3,4-dihydro-2H-pyridine-1-carboxylic acid (2-chloro-3-methyl-phenyl)-amide | | |
| 160 | 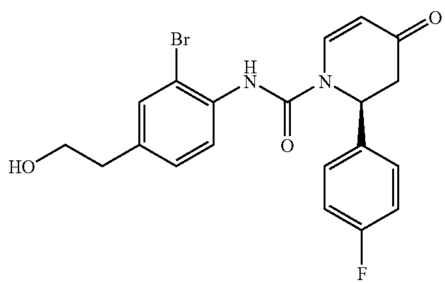 | (S)-2-(4-Fluoro-phenyl)-4-oxo-3,4-dihydro-2H-pyridine-1-carboxylic acid [2-bromo-4-(2-hydroxy-ethyl)-phenyl]-amide | | |
| 161 | 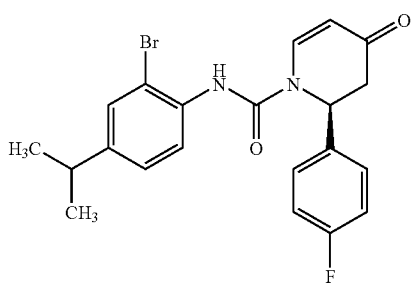 | (S)-2-(4-Fluoro-phenyl)-4-oxo-3,4-dihydro-2H-pyridine-1-carboxylic acid (2-bromo-4-isopropyl-phenyl)-amide | | |
| 162 | 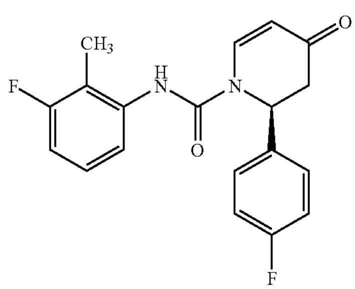 | (S)-2-(4-Fluoro-phenyl)-4-oxo-3,4-dihydro-2H-pyridine-1-carboxylic acid (3-fluoro-2-methyl-phenyl)-amide | | |
| 163 | 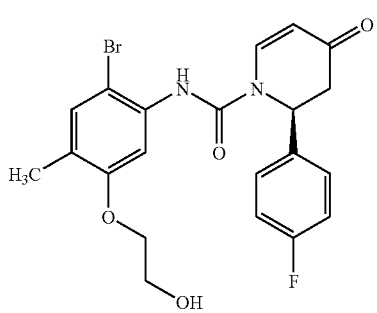 | (S)-2-(4-Fluoro-phenyl)-4-oxo-3,4-dihydro-2H-pyridine-1-carboxylic acid [2-bromo-5-(2-hydroxy-ethoxy)-4-methyl-phenyl]-amide | | |

TABLE 1-continued

| # | Structure | Name | M + H/MP | pIC$_{50}$ |
|---|---|---|---|---|
| 164 | 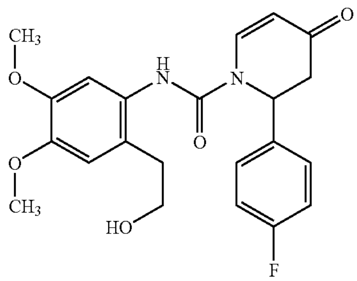 | 2-(4-Fluoro-phenyl)-4-oxo-3,4-dihydro-2H-pyridine-1-carboxylic acid [2-(2-hydroxy-ethyl)-4,5-dimethoxy-phenyl]-amide | | |
| 165 | 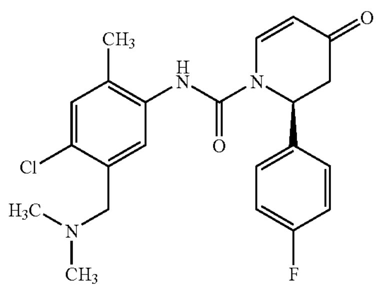 | (S)-2-(4-Fluoro-phenyl)-4-oxo-3,4-dihydro-2H-pyridine-1-carboxylic acid (4-chloro-5-dimethylaminomethyl-2-methyl-phenyl)-amide | | |
| 166 | 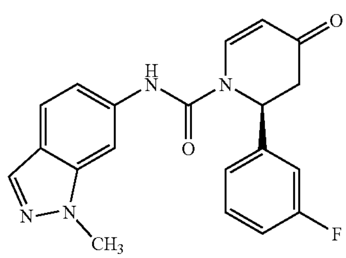 | (S)-2-(3-Fluoro-phenyl)-4-oxo-3,4-dihydro-2H-pyridine-1-carboxylic acid (1-methyl-1H-indazol-6-yl)-amide | | |
| 167 | 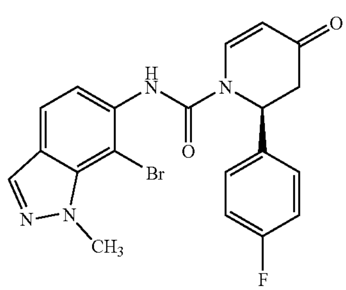 | (S)-2-(4-Fluoro-phenyl)-4-oxo-3,4-dihydro-2H-pyridine-1-carboxylic acid (7-bromo-1-methyl-1H-indazol-6-yl)-amide | | |
| 168 | 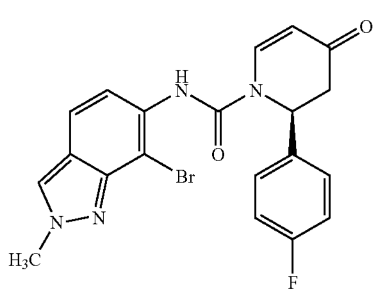 | (S)-2-(4-Fluoro-phenyl)-4-oxo-3,4-dihydro-2H-pyridine-1-carboxylic acid (7-bromo-2-methyl-2H-inbazol-6-yl)-amide | | |

TABLE 1-continued

| # | Structure | Name | M + H/MP | pIC$_{50}$ |
|---|---|---|---|---|
| 169 | 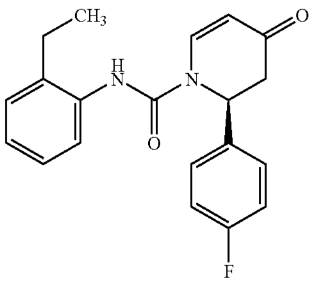 | (S)-2-(4-Fluoro-phenyl)-4-oxo-3,4-dihydro-2H-pyridine-1-carboxylic acid (2-ethyl-phenyl)-amide | | |
| 170 | 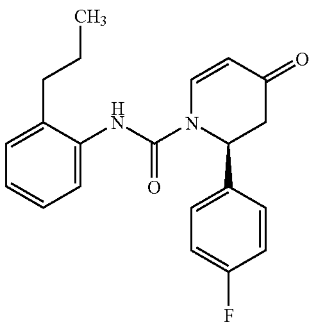 | (S)-2-(4-Fluoro-phenyl)-4-oxo-3,4-dihydro-2H-pyridine-1-carboxylic acid (2-propyl-phenyl)-amide | | |
| 171 | 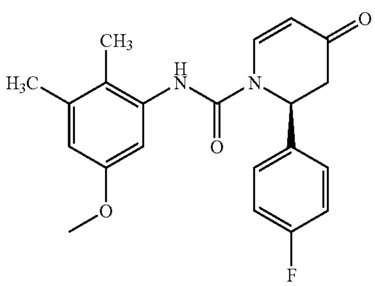 | (S)-2-(4-Fluoro-phenyl)-4-oxo-3,4-dihydro-2H-pyridine-1-carboxylic acid (5-methoxy-2,3-dimethyl-phenyl)-amide | | |
| 172 | 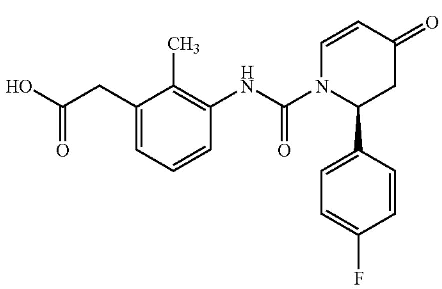 | (3-{[(S)-2-(4-Fluoro-phenyl)-4-oxo-3,4-dihydro-2H-pyridine-1-carbonyl]-amino}-2-methyl-phenyl)-acetic acid | | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula I, wherein $R^6$, $R^7$, $R^8$, $R^9$, $R^{10}$ and $R^{11}$ are as defined herein.

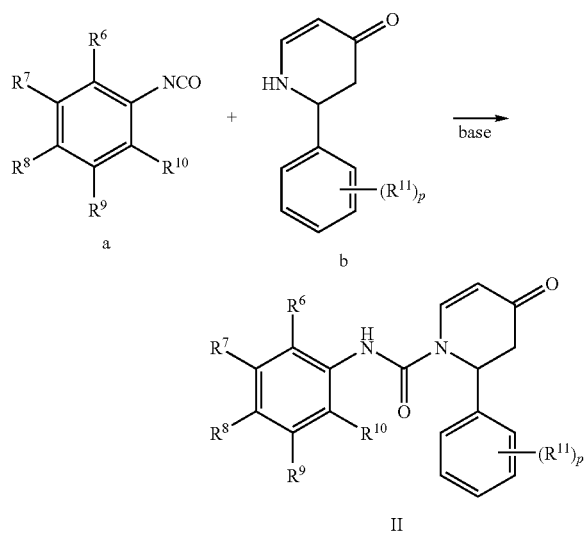

In Scheme A, aryl isocyanate compound a is reacted with the lithium salt of aryl dihydropyridone compound b, which may be prepared by treatment of b with an alkyl lithium reagent or lithium bis(trimethylsilyl)amide, to afford dihydropyridone urea compound II. Compound II is a compound of formula I as noted above.

Aryl isocyanate a may be prepared by treatment of the corresponding aryl amine with phosgene. Such aryl amine compounds may in many embodiments be made by reduction of the corresponding aryl nitro compounds, as illustrated in the experimental examples below.

Aryl dihydropyridone b may be prepared by reaction of the corresponding aryl Grignard reagent with 4-methoxy-pyridine, in the presence of benzoyl chloride, followed by hydrolysis.

In the embodiment of Scheme A, aryl isocyanate a is shown as a phenyl compound, and aryl dihydropyridone b is shown as a phenyl compound. The phenyl moieties of these compounds in many embodiments may be replaced by various heteroaryl, such as indolyl, indazolyl, pyridinyl, and the like, as demonstrated in the experimental examples below.

Many variations of Scheme A are possible and will suggest themselves to those skilled in the art. Specific details for producing compounds of the invention are described in the Examples section below.

Utility

The compounds of the invention are usable for the treatment of a wide range of inflammatory diseases and conditions such as arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. The subject compounds would be useful for the treatment of pulmonary disorders or lung inflammation, including adult respiratory distress syndrome, pulmonary sarcoidosis, asthma, silicosis, and chronic pulmonary inflammatory disease.

The compounds of the invention are also expected to find utility as analgesics in the treatment of diseases and conditions associated with pain from a wide variety of causes, including, but not limited to, inflammatory pain such as pain associated with arthritis (including rheumatoid arthritis and osteoarthritis), surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Further, compounds of the invention are useful for treating respiratory disorders, including chronic obstructive pulmonary disorder (COPD), asthma, bronchospasm, and the like.

Additionally, compounds of the invention are useful for treating gastrointestinal disorders, including Irritable Bowel Syndrome (IBS), Inflammatory Bowel Disease (IBD), biliary colic and other biliary disorders, renal colic, diarrhea-dominant IBS, pain associated with GI distension, and the like.

The compounds of the invention are also useful for the treatment of muscular sclerosis.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration.

The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

ABBREVIATIONS

BETBDMS 2-bromoethoxy tertbutyldimethylsilane
DBU 1,8-diazabicyclo[5.4.0]undec-7-ene
DCM dichloromethane/methylene chloride
DIPEA diisopropyl ethylamine (Hunig's base)
DME 1,2-dimethoxyethane (glyme)
DMF N,N-dimethylformamide
DMFDMA N,N-dimethylformamide dimethyl acetal
DMSO dimethyl sulfoxide
DMAP 4-dimethylaminopyridine
ECDI 1-ethyl-3-(3'-dimethylaminopropyl)carbodiimide
EtOAc ethyl acetate
EtOH ethanol
gc gas chromatography
HMPA hexamethylphosphoramide
HOBt N-Hydroxybenzotriazole
hplc high performance liquid chromatography
IPA isopropanol
IPBAPE isopropenylboronic acid pinacol ester
mCPBA m-chloroperbenzoic acid
MeCN acetonitrile
NMM N-methyl morpholine
NMP N-methylpyrrolidinone
Pd$_2$(dba)$_3$ Tris(dibenzylideneacetone)dipalladium(0)
TBAF tetra-n-butyl ammonium fluoride
TEA triethylamine
THF tetrahydrofuran
LDA lithium diisopropylamine
TBDMS tert-butyl dimethylsilyl chloride
TLC thin layer chromatography
Xantphos 4,5-bis(diphenylphosphino)-9,9-dimethyl-xanthene Preparation 1

(1R,2S,5R)-5-Methyl-2-(1-methyl-1-phenyl-ethyl)-cyclohexanol chloroformate

The synthetic procedure used in this preparation is outlined in Scheme B.

SCHEME B

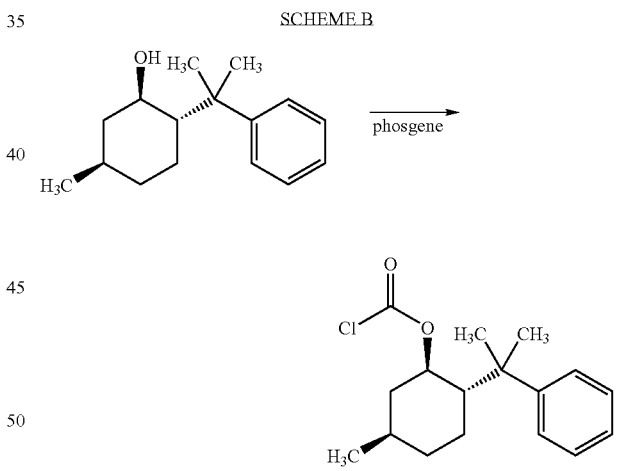

Following the procedure reported in JACS 1994, 116, 4719-4728, to a solution of (−)-8-phenylmenthol (12.66 g, 54.4 mmol) and quinoline (15.88 mL, 134.1 mmol) in toluene (210 mL) at 0° C. was added 20% phosgene in toluene (45 mL, 87.9 mmol). The mixture was stirred at 0° C. for 30 minutes and at room temperature for 16 hours. Diethyl ether and 2N HCl were added and the mixture was stirred for 5 minutes. The layers were separated and the combined organics were washed with water, brine dried over MgSO4 and concentrated to dryness. The resulting crude 5-methyl-2-(1-methyl-1-phenyl-ethyl)-cyclohexyl chloroformate (14.43 g) was used without further purification.

Preparation 2

4-methoxy-3-triisopropylsilyl-pyridine

The synthetic procedure used in this preparation is outlined in Scheme C.

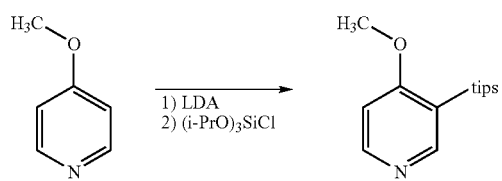

SCHEME C

Following the procedure reported in *JACS* 1994, 116, 4719-4728, to a solution of 4-methoxypyridine (14.0 g, 128.3 mmol) in THF (150 mL) was added at −25° C., 2.0M LDA in heptane/THF/ethyl benzene (76.9 mL, 153.9 mmol). The mixture was stirred at −25° C. for 30 minutes. Triisopropylsilyl chloride (35.3 mL, 166.8 mmol) was added and the mixture was stirred at −25° C. for 15 minutes and then at room temperature for 16 hours. Water was added and the mixture was extracted with EtOAc. The extract was washed with water, brine dried over MgSO4 and concentrated to dryness. Purification of the residue by flash chromatography (hexane/ethylacetate 8:2-1:1) gave 4-methoxy-3-triisopropylsilanyl-pyridine (7.56 g, 22%) as an orange solid.

Preparation 3

(S)-2-(4-Fluoro-phenyl)-2,3-dihydro-1H-pyridin-4-one

The synthetic procedure used in this preparation is outlined in Scheme D.

SCHEME D

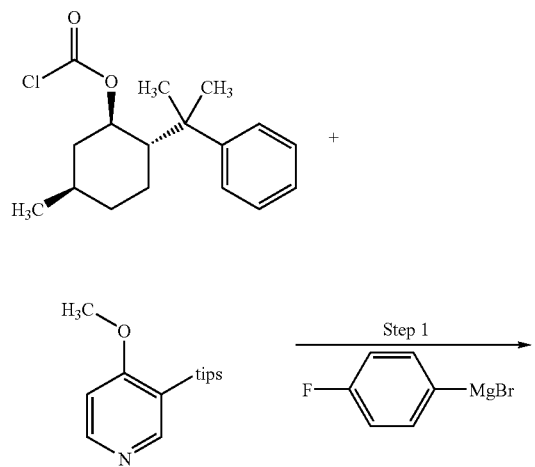

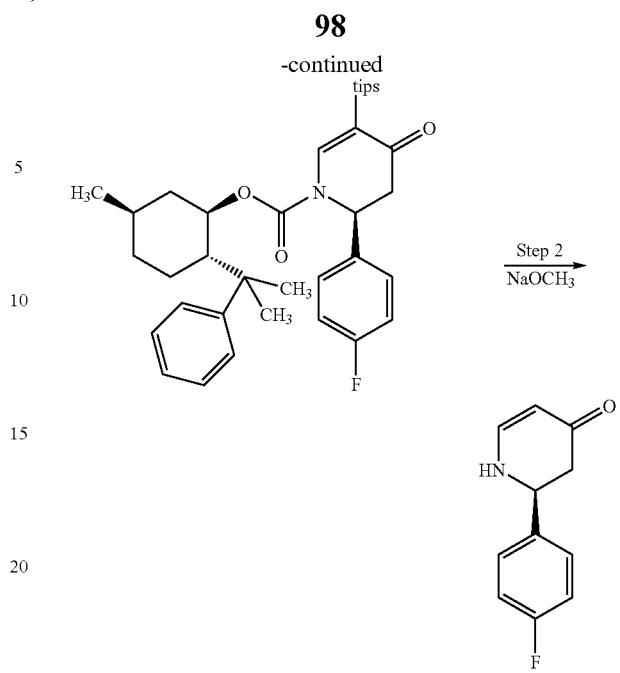

Step 1 2-(4-Fluoro-phenyl)-4-oxo-5-triisopropylsilanyl-3,4-dihydro-2H-pyridine-1-carboxylic acid 5-methyl-2-(1-methyl-1-phenyl-ethyl)-cyclohexyl ester Following the procedure reported in *JACS* 1994, 116, 4719-4728, to a solution of 4-methoxy-3-triisopropylsilanyl-pyridine (6.06 g, 22.8 mmol) in toluene (160 mL) at −25° C. was added a solution of 5-methyl-2-(1-methyl-1-phenyl-ethyl)-cyclohexyl chloroformate (6.73 g, 26.2 mmol) in toluene (140 mL). After 15 minutes the mixture was cooled to −78° C. and 1.0M 4-fluorophenyl magnesium bromide in THF (26.1 mL, 26.2 mmol) was added slowly. The mixture was stirred at −78° C. for 1 hour. 2N HCl was added and the mixture was allowed to warm to room temperature and was stirred for additional 15 minutes. The mixture was extracted with ethyl acetate, washed with water and brine, dried over MgSO4, filtered and concentrated to dryness. Purification of the residue by flash chromatography (hexane/ethyl acetate 9:1) gave 2-(4-fluoro-phenyl)-4-oxo-5-triisopropylsilanyl-3,4-dihydro-2H-pyridine-1-carboxylic acid 5-methyl-2-(1-methyl-1-phenyl-ethyl)-cyclohexyl ester (1.06 g, 48%) as a white solid.

Step 2 (S)-2-(4-Fluoro-phenyl)-2,3-dihydro-1H-pyridin-4-one

To a solution of 2-(4-fluoro-phenyl)-4-oxo-5-triisopropylsilanyl-3,4-dihydro-2H-pyridine-1-carboxylic acid 5-methyl-2-(1-methyl-1-phenyl-ethyl)-cyclohexyl ester (7.78 g, 12.8 mmol) in methanol (95 mL) was added 25% sodium methoxide in methanol (29.4 mL, 128.4 mmol). The mixture was heated at reflux for 16 h. After cooling to rt, oxalic acid (46.3 g, 512 mmol) was added and the mixture was stirred for 2 h. The solvent was evaporated to dryness. The crude was partitioned between ethyl acetate and water. The organic layer was washed with water, brine dried over MgSO4, filtered and concentrated to dryness. Purification by flash chromatography (hex:EtOAc/2:8-0:1) gave (S)-2-(4-fluoro-phenyl)-2,3-dihydro-1H-pyridin-4-one (0.886 g, 36%, ee 99.3%) as a yellow solid.

Similarly prepared, using the appropriate substituted phenyl Grignard reagents, were:
(S)-2-(3,5-difluoro-phenyl)-2,3-dihydro-1H-pyridin-4-one;
(S)-2-(3-fluoro-phenyl)-2,3-dihydro-1H-pyridin-4-one; and
(S)-2-(3,4-difluoro-phenyl)-2,3-dihydro-1H-pyridin-4-one.

Example 1

(S)-2-(4-fluoro-phenyl)-4-oxo-3,4-dihydro-2H-pyridine-1-carboxylic acid (2-bromo-4,5-dimethoxy-phenyl)-amide The synthetic procedure used in this example is outlined in Scheme E.

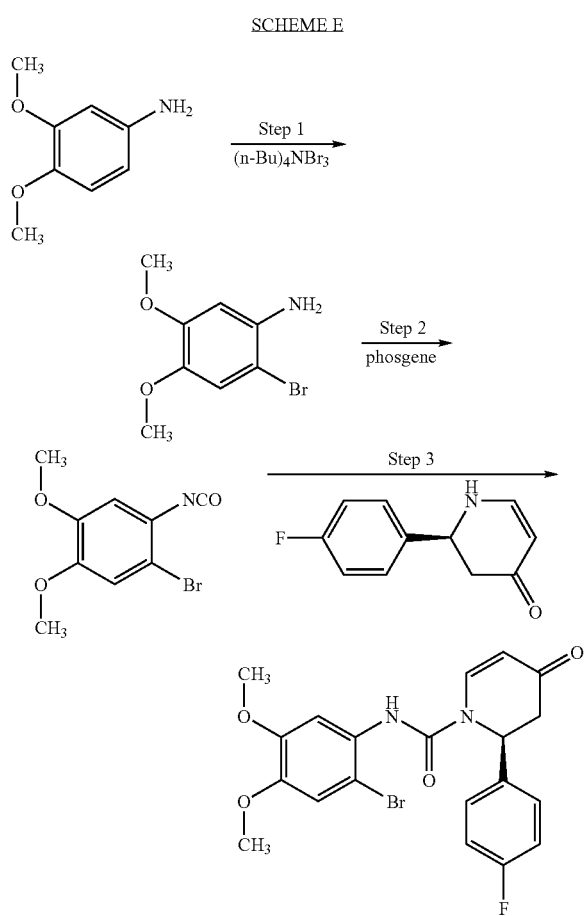

Step 1 2-Bromo-4,5-dimethoxy-aniline

Following the procedure reported in *JACS* 1996, 118, 1028-1030, 4-aminoveratrole (3.06 g, 20.0 mmol) was dissolved in a mixture of dichloromethane (80 ml) and methanol (40 ml) at room temperature. Tetrabutylammonium tribromide (1.15 eq, 11.09 g) was added and the mixture was allowed to stir for 20 minutes. The mixture was extracted with saturated aqueous sodium sulfite solution. The organic layer was washed with water, dried over anhydrous sodium sulfate, filtered and concentrated in vacuo. The residue was purified by flash chromatography (gradient 10:1 to 7:3 Hexanes/Ethyl Acetate) to give 2-Bromo-4,5-dimethoxy-aniline 1.403 g (30%) of a yellow oil.

Step 2
1-Bromo-2-isocyanato-4,5-dimethoxy-benzene

2-Bromo-4,5-dimethoxyaniline (464 mg, 2.0 mmol) was dissolved in 10 ml of toluene at room temperature. DMAP (1 eq, 245 mg), pyridine (1.3 eq, 0.22 ml) were added followed by phosgene (1.33 eq, 1.33 ml of a 20% solution in toluene). The mixture was heated to 90° C. for 4 hours. Upon cooling, the mixture was filtered and the filtrate was concentrated in vacuo to give 1-bromo-2-isocyanato-4,5-dimethoxy-benzene (542 mg, quantitative) as a light brown oil.

Step 3 (S)-2-(4-fluoro-phenyl)-4-oxo-3,4-dihydro-2H-pyridine-1-carboxylic acid (2-bromo-4,5-dimethoxy-phenyl)-amide (S)-2-(4-Fluoro-phenyl)-2,3-dihydro-1H-pyridin-4-one (57 mg, 0.30 mmol) from Preparation 3 was dissolved in 10 ml of THF and cooled to –40° C. n-BuLi (1.1 eq, 0.12 ml of a 2.5 M soln) was added dropwise, forming a purple suspension. This mixture was allowed to stir for 30 minutes until the purple color changed to white. 1-Bromo-2-isocyanato-4,5-dimethoxy-benzene (1 eq, 77 mg) was added. The mixture was allowed to stir for 15 minutes at –40° C. then allowed to warm to room temperature and stir for 2 hours. The reaction was then quenched with saturated ammonium chloride solution. The mixture was diluted with water and extracted with ethyl acetate. The combined organic extracts were washed with brine, dried over anhydrous sodium sulfate, filtered and concentrated in vacuo. The residue was purified by flash chromatography (hexanes/ethyl acetate 7:3) to obtain (S)-2-(4-fluoro-phenyl)-4-oxo-3,4-dihydro-2H-pyridine-1-carboxylic acid (2-bromo-4,5-dimethoxy-phenyl)-amide (82 mg, 61%) as a brown oil. MS (ES+) m/z 449 (M+H).

In a similar fashion, the following compounds were prepared:
(S)-2-(4-Fluoro-phenyl)-4-oxo-3,4-dihydro-2H-pyridine-1-carboxylic acid (2-bromo-4-fluoro-5-methoxy-phenyl)-amide;
(S)-2-(4-Fluoro-phenyl)-4-oxo-3,4-dihydro-2H-pyridine-1-carboxylic acid (2-bromo-4-chloro-5-methoxy-phenyl)-amide;
(S)-2-(4-Fluoro-phenyl)-4-oxo-3,4-dihydro-2H-pyridine-1-carboxylic acid (2-bromo-5-methoxy-4-methyl-phenyl)-amide;
(S)-2-(3-Fluoro-phenyl)-4-oxo-3,4-dihydro-2H-pyridine-1-carboxylic acid (2-bromo-5-methoxy-4-methyl-phenyl)-amide;
(S)-2-(4-Fluoro-phenyl)-4-oxo-3,4-dihydro-2H-pyridine-1-carboxylic acid (4,5-dimethoxy-2-methyl-phenyl)-amide;
(S)-2-(4-Fluoro-phenyl)-4-oxo-3,4-dihydro-2H-pyridine-1-carboxylic acid (3,4-dimethoxy-phenyl)-amide;
(S)-2-(4-Fluoro-phenyl)-4-oxo-3,4-dihydro-2H-pyridine-1-carboxylic acid (4-chloro-2-fluoro-5-methoxy-phenyl)-amide;
(S)-2-(3-Fluoro-phenyl)-4-oxo-3,4-dihydro-2H-pyridine-1-carboxylic acid (5-methoxy-2-methyl-phenyl)-amide;
(S)-2-(4-Fluoro-phenyl)-4-oxo-3,4-dihydro-2H-pyridine-1-carboxylic acid (3-methoxy-4-methyl-phenyl)-amide;
(S)-2-(4-Fluoro-phenyl)-4-oxo-3,4-dihydro-2H-pyridine-1-carboxylic acid (2,4-dichloro-5-methoxy-phenyl)-amide;
(S)-5-Bromo-4-{[2-(4-fluoro-phenyl)-4-oxo-3,4-dihydro-2H-pyridine-1-carbonyl]-amino}-2-methoxy-benzoic acid methyl ester;
(S)-2-(4-Fluoro-phenyl)-4-oxo-3,4-dihydro-2H-pyridine-1-carboxylic acid (2-bromo-4-difluoromethoxy-5-methoxy-phenyl)-amide;

101

(S)-2-(4-Fluoro-phenyl)-4-oxo-3,4-dihydro-2H-pyridine-1-carboxylic acid (2-bromo-4-cyano-5-methoxy-phenyl)-amide;
2-(4-Fluoro-phenyl)-4-oxo-3,4-dihydro-2H-pyridine-1-carboxylic acid (1-methyl-1H-indol-6-yl)-amide;
(S)-2-(4-Fluoro-phenyl)-4-oxo-3,4-dihydro-2H-pyridine-1-carboxylic acid (5-acetyl-2-bromo-4-chloro-phenyl)-amide;
(S)-2-(3-Fluoro-phenyl)-4-oxo-3,4-dihydro-2H-pyridine-1-carboxylic acid (2-bromo-4,5-dimethoxy-phenyl)-amide;
(S)-2-(4-Fluoro-phenyl)-4-oxo-3,4-dihydro-2H-pyridine-1-carboxylic acid (2-bromo-4,5-dichloro-phenyl)-amide;
(S)-2-(4-Fluoro-phenyl)-4-oxo-3,4-dihydro-2H-pyridine-1-carboxylic acid (2-bromo-4-chloro-5-fluoro-phenyl)-amide;
(S)-2-(4-Fluoro-phenyl)-4-oxo-3,4-dihydro-2H-pyridine-1-carboxylic acid (2-bromo-4-chloro-5-methylsulfanyl-phenyl)-amide;
(S)-2-(4-Fluoro-phenyl)-4-oxo-3,4-dihydro-2H-pyridine-1-carboxylic acid (2-bromo-4-chloro-5-trifluoromethyl-phenyl)-amide;
(S)-2-(4-Fluoro-phenyl)-4-oxo-3,4-dihydro-2H-pyridine-1-carboxylic acid (2-bromo-4-chloro-5-iodo-phenyl)-amide;
(S)-2-(4-Fluoro-phenyl)-4-oxo-3,4-dihydro-2H-pyridine-1-carboxylic acid (2-bromo-5-cyano-4-methyl-phenyl)-amide;
(S)-2-(4-Fluoro-phenyl)-4-oxo-3,4-dihydro-2H-pyridine-1-carboxylic acid (2-bromo-5-methoxy-4-trifluoromethyl-phenyl)-amide;
(S)-4-Oxo-2-phenyl-3,4-dihydro-2H-pyridine-1-carboxylic acid (2-bromo-4-chloro-5-methoxy-phenyl)-amide;
(Rac)-4-Oxo-2-phenyl-3,4-dihydro-2H-pyridine-1-carboxylic acid (2-bromo-4,5-dimethoxy-phenyl)-amide; and
(S)-4-Bromo-2-chloro-5-{[2-(4-fluoro-phenyl)-4-oxo-3,4-dihydro-2H-pyridine-1-carbonyl]-amino}-benzoic acid methyl ester.

Additional compounds prepared by the above procedure are shown in Table 1.

Example 2

(S)-2-(4-Fluoro-phenyl)-4-oxo-3,4-dihydro-2H-pyridine-1-carboxylic acid [5-bromo-3-methyl-1-(toluene-4-sulfonyl)-1H-indazol-6-yl]-amide The synthetic procedure used in this example is outlined in Scheme F.

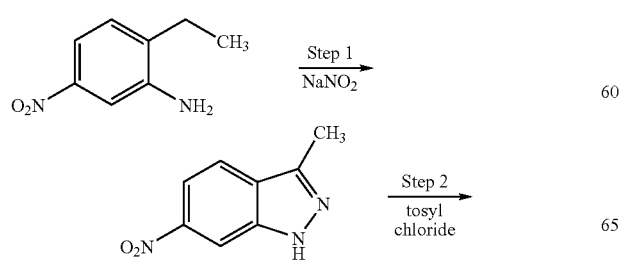

102

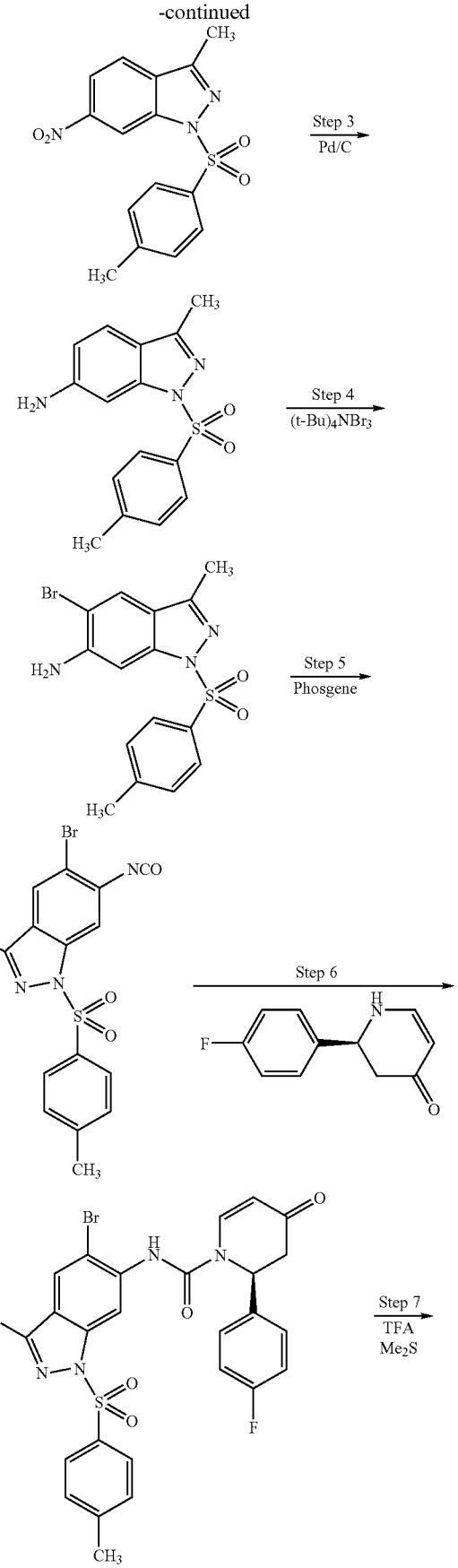

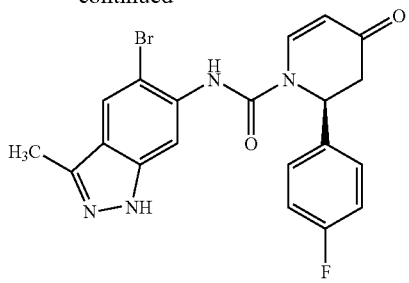

Step 1 3-Methyl-6-nitro-1H-indazole

Following generally the procedure reported by *Organic Synthesis* 1955, *Coll. Vol.* 3, 660; 1940, 20, 73, 2-ethyl-5-nitroaniline (1.021 g, 6.14 mmol) was dissolved in glacial acetic acid (40 ml) and the mixture was cooled to 0° C. A solution of sodium nitrite (1 eq, 424 mg) in water (1 ml) was added all at once. Stirring was continued for 15 minutes at 25° C. After 3 hours, residual solids were filtered off and discarded, and the filtrate was allowed to stand for 3 days at room temperature. The solution was concentrate in vacuo, and the residue was diluted with 2 ml of water and stirred vigorously. The solid product was filtered and washed thoroughly with cold water, dried and purified by flash chromatography (4:1 hexanes/ethyl acetate) to give 3-methyl-6-nitro-1H-indazole (436 mg, 40.5%) as a solid.

Step 2 3-Methyl-6-nitro-1-(toluene-4-sulfonyl)-1H-indazole

3-Methyl-6-nitro-1H-indazole (436 mg, 2.46 mmol) was dissolved in 25 ml of dichloromethane at room temperature. DMAP (5 mg) and pyridine (1.1 eq, 0.38 ml) were added followed by tosyl chloride (1.1 eq, 516 mg). The mixture was allowed to stir at room temperature overnight. The mixture was filtered and the filtrate was concentrated in vacuo. The residue was purified by flash chromatography (gradient 9:1 to 4:1 Hexanes/Ethyl Acetate) to give 3-methyl-6-nitro-1-(toluene-4-sulfonyl)-1H-indazole (850 mg, quant) as a light brown crystalline solid.

Step 3 3-Methyl-1-(toluene-4-sulfonyl)-1H-indazol-6-ylamine

3-Methyl-6-nitro-1-(toluene-4-sulfonyl)-1H-indazole (750 mg, 2.26 mmol) was dissolved in 30 ml of methanol at room temperature. 10% Palladium on Carbon (200 mg) was added and the mixture was stirred under a balloon of hydrogen overnight. The mixture was filtered through celite and the filtrate was concentrated in vacuo. The residue was purified by flash chromatography (gradient 9:1 to 4:1 Hexanes/Ethyl Acetate) to give 3-methyl-1-(toluene-4-sulfonyl)-1H-indazol-6-ylamine (265 mg, 38.9%) as a light tan crystalline solid.

Step 4 5-Bromo-3-methyl-1-(toluene-4-sulfonyl)-1H-indazol-6-ylamine

3-Methyl-1-(toluene-4-sulfonyl)-1H-indazol-6-ylamine (301 mg, 1.0 mmol) was dissolved in 1,2-dichloroethane (80 ml) and methanol (40 ml) at room temperature. The mixture was heated to 80° C. and then the tetrabutylammonium tribromide (1.0 eq, 482 mg) was added. Stirring was continued for 10 minutes, and then the mixture was partitioned between diethyl ether and saturated aqueous sodium sulfite solution. The organic layer was separated, washed with water, dried over anhydrous sodium sulfate, filtered and concentrated in vacuo. The residue was purified by flash chromatography (gradient 9:1 to 4:1 hexanes/ethyl acetate) to give 5-bromo-3-methyl-1-(toluene-4-sulfonyl)-1H-indazol-6-ylamine (280 mg, 73.7%) as a white powder.

Step 5 5-Bromo-6-isocyanato-3-methyl-1-(toluene-4-sulfonyl)-1H-indazole

5-Bromo-3-methyl-1-(toluene-4-sulfonyl)-1H-indazol-6-ylamine (138 mg, 0.36 mmol) was dissolved in 5 ml of toluene at room temperature. DMAP (1 eq, 44 mg), pyridine (1.3 eq, 0.04 ml) were added followed by phosgene (1.33 eq, 0.24 ml of a 20% solution in toluene). The mixture was allowed to stir at room temperature for 2 hours, forming a fine white precipitate. The mixture was filtered and the filtrate was concentrated in vacuo. The residue was diluted with dichloromethane and concentrated in vacuo again to give 5-bromo-6-isocyanato-3-methyl-1-(toluene-4-sulfonyl)-1H-indazole (150 mg, quantitative) as a white crystalline solid.

Step 6 (S)-2-(4-fluoro-phenyl)-4-oxo-3,4-dihydro-2H-pyridine-1-carboxylic acid [5-bromo-3-methyl-1-(toluene-4-sulfonyl)-1H-indazol-6-yl]-amide (S)-2-(4-Fluoro-phenyl)-2,3-dihydro-1H-pyridin-4-one (58 mg, 0.30 mmol) was dissolved in 10 ml of THF and cooled to −40° C. n-BuLi (1.1 eq, 0.16 ml of a 2.5M soln) was added dropwise, forming a purple suspension. This mixture was allowed to stir for 30 minutes until the purple color changed to white. 5-Bromo-6-isocyanato-3-methyl-1-(toluene-4-sulfonyl)-1H-indazole (1 eq, 146 mg) was added and the mixture was allowed to stir for 1 hour at −40° C., then warmed to warm to room temperature and stirred for 2 hours. The reaction was then quenched with saturated aqueous ammonium chloride solution. The mixture was diluted with water and extracted with ethyl acetate. The combined organic extracts were washed with brine, dried over anhydrous sodium sulfate, filtered and concentrated in vacuo. The residue was purified by flash chromatography (gradient 9:1 to 1:1 hexanes/ethyl acetate) to give (S)-2-(4-fluoro-phenyl)-4-oxo-3,4-dihydro-2H-pyridine-1-carboxylic acid [5-bromo-3-methyl-1-(toluene-4-sulfonyl)-1H-indazol-6-yl]-amide (140 mg, 65.1%) as a yellow foam.

Step 7 (S)-2-(4-Fluoro-phenyl)-4-oxo-3,4-dihydro-2H-pyridine-1-carboxylic acid [5-bromo-3-methyl-1-(toluene-4-sulfonyl)-1H-indazol-6-yl]-amide (S)-2-(4-Fluoro-phenyl)-4-oxo-3,4-dihydro-2H-pyridine-1-carboxylic acid [5-bromo-3-methyl-1-(toluene-4-sulfonyl)-1H-indazol-6-yl]-amide (40 mg, 0.07 mmol) was dissolved in dimethylsulfide (5 ml) at room temperature. Trifluoroacetic acid (1 ml) was added and the mixture was allowed to stir at room temperature overnight. The solution was concentrated in vacuo, and the residue was purified by flash chromatography (gradient 9:1 to 1:1 Hexanes/Ethyl Acetate) to give (S)-2-(4-fluoro-phenyl)-4-oxo-3,4-dihydro-2H-pyridine-1-carboxylic acid (5-bromo-3-methyl-1H-indazol-6-yl)-amide 30 mg (90.0%) of an off-white foam. MS (ES+) m/z 443 (M+H).

Example 3

2-(4-Fluoro-phenyl)-4-oxo-3,4-dihydro-2H-pyridine-1-carboxylic acid (2-fluoro-5-methoxy-4-methyl-phenyl)-amide The synthetic procedure used in this example is outlined in Scheme G.

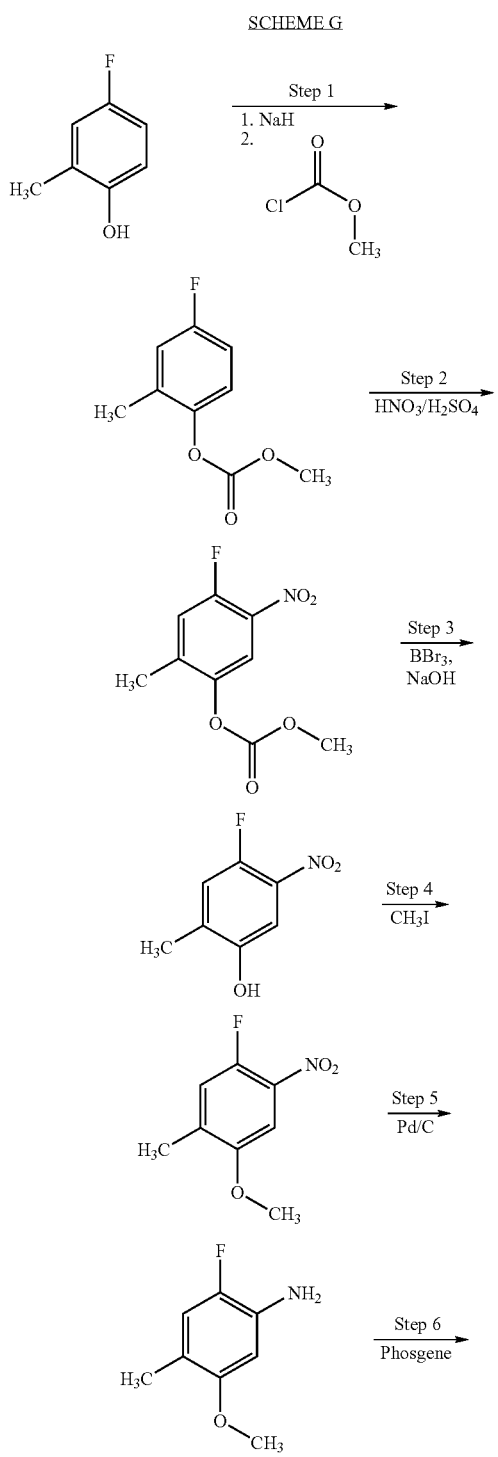

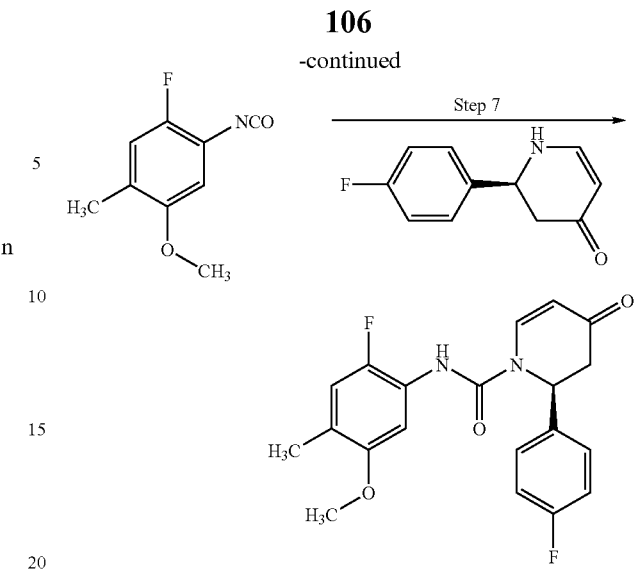

Step 1 Carbonic acid 4-fluoro-2-methyl-phenyl ester methyl ester

Following the procedure of *J. Med. Chem.* 1999, 42, 5369, 4-fluoro-2-methylphenol (10.0 g, 79.0 mmol) was dissolved in THF and the mixture was cooled to 0° C. NaH (1 eq, 3.16 g of a 60% dispersion in oil) was added carefully. After gas evolution ceased, methyl chloroformate (1 eq, 6.8 ml) was added. The mixture was allowed to warm to room temperature and stir for 3 hours. The mixture was washed with cold water, dried over anhydrous sodium sulfate, filtered and then concentrated in vacuo to give carbonic acid 4-fluoro-2-methyl-phenyl ester methyl ester (12.8 g, 88.0%) as an oil.

Step 2 Carbonic acid 4-fluoro-2-methyl-5-nitro-phenyl ester methyl ester

Carbonic acid 4-fluoro-2-methyl-phenyl ester methyl ester (12.8 g, 69.5 mmol) was suspended in 8 ml of concentrated sulfuric acid and cooled to 0° C. A mixture of concentrated nitric acid (8 ml) in concentrated sulfuric acid (8 ml) was added slowly, maintaining a reaction temperature below 50° C. After addition the mixture was stirred for 2 hours. The reaction mixture was poured into ice-water, forming a precipitate which was filtered and dried to give carbonic acid 4-fluoro-2-methyl-5-nitro-phenyl ester methyl ester (8.0 g, 50.3%) as a white powder.

Step 3 4-Fluoro-2-methyl-5-nitro-phenol

Carbonic acid 4-fluoro-2-methyl-5-nitro-phenyl ester methyl ester (1.8 g, 7.8 mmol) was dissolved in dichloromethane (100 ml) and cooled to 0° C. Boron tribromide (1 M in dichloromethane, 8 ml) was added. The mixture was allowed to warm to room temperature and was stirred overnight. To the solution was added 1N sodium hydroxide (25 ml) and the mixture was stirred vigorously for 1 hour. The layers were separated and the organic layer was dried over anhydrous sodium sulfate, and filtered and concentrated in vacuo to give 4-fluoro-2-methyl-5-nitro-phenol (1.083 g, 80.6%) as a red crystalline solid.

Step 4
1-Fluoro-4-methoxy-5-methyl-2-nitro-benzene

4-Fluoro-2-methyl-5-nitro-phenol (1.08 g, 6.3 mmol) was dissolved in acetone (100 ml). To this was added solid sodium carbonate (2 eq, 1.34 g) and iodomethane (10 eq, 3.75 ml). The mixture was allowed to stir at room temperature overnight. The mixture was filtered and the filtrate was concentrated in vacuo to give 1-fluoro-4-methoxy-5-methyl-2-nitro-benzene (1.18 g, quantitative) as a pale yellow solid.

Step 5 2-Fluoro-5-methoxy-4-methyl-phenylamine

1-Fluoro-4-methoxy-5-methyl-2-nitro-benzene (1.18 g, 6.4 mmol) was dissolved in 40 ml of methanol at room temperature. 10% Palladium on Carbon (200 mg) was added and the mixture was stirred under a balloon of hydrogen overnight. The mixture was filtered through celite. The filtrate was concentrated in vacuo to give 2-fluoro-5-methoxy-4-methyl-phenylamine (990 mg, quantitative) as a solid.

Step 6
1-Fluoro-2-isocyanato-4-methoxy-5-methyl-benzene

2-Fluoro-5-methoxy-4-methyl-phenylamine (78 mg, 0.50 mmol) was dissolved in 10 ml of toluene at room temperature. DMAP (1 eq, 61 mg), pyridine (1.3 eq, 0.06 ml) were added followed by phosgene (1.33 eq, 0.34 ml, 20% solution in toluene). The mixture was allowed to stir at room temperature for 3 hours, forming a fine white precipitate. The mixture was filtered and the filtrate was concentrated in vacuo. The residue was diluted with dichloromethane and concentrated in vacuo again to give 1-fluoro-2-isocyanato-4-methoxy-5-methyl-benzene (90 mg, quantitative) as a clear oil.

Step 7 2-(4-Fluoro-phenyl)-4-oxo-3,4-dihydro-2H-pyridine-1-carboxylic acid (2-fluoro-5-methoxy-4-methyl-phenyl)-amide (S)-2-(4-Fluoro-phenyl)-2,3-dihydro-1H-pyridin-4-one (95 mg, 0.50 mmol) was dissolved in THF and cooled to –40° C. n-BuLi (1.1 eq, 0.34 ml of 2.5M solution) was added dropwise, forming a purple suspension. The mixture was allowed to stir for 30 minutes until the purple color changed to white. 1-Fluoro-2-isocyanato-4-methoxy-5-methyl-benzene (1 eq, 90 mg) was added. The mixture was allowed to stir for 1 hour at –40° C., then allowed to warm to room temperature and stirred for 2 hours. The reaction was quenched with saturated ammonium chloride solution. The mixture was diluted with water and extracted with ethyl acetate. The combined organic extracts were washed with brine, dried over anhydrous sodium sulfate, and concentrated in vacuo. The residue was purified by flash chromatography (gradient 9:1 to 1:1 hexanes/ethyl acetate) to give 2-(4-Fluoro-phenyl)-4-oxo-3,4-dihydro-2H-pyridine-1-carboxylic acid (2-fluoro-5-methoxy-4-methyl-phenyl)-amide (46 mg, 24.7%) as a foam. MS (ES+) m/z 373 (M+H).

Example 4
(S)-5-bromo-4-{[2-(4-fluoro-phenyl)-4-oxo-3,4-dihydro-2H-pyridine-1-carbonyl]-amino}-2-methoxy-benzamide The synthetic procedure used in this example is outlined in Scheme H.

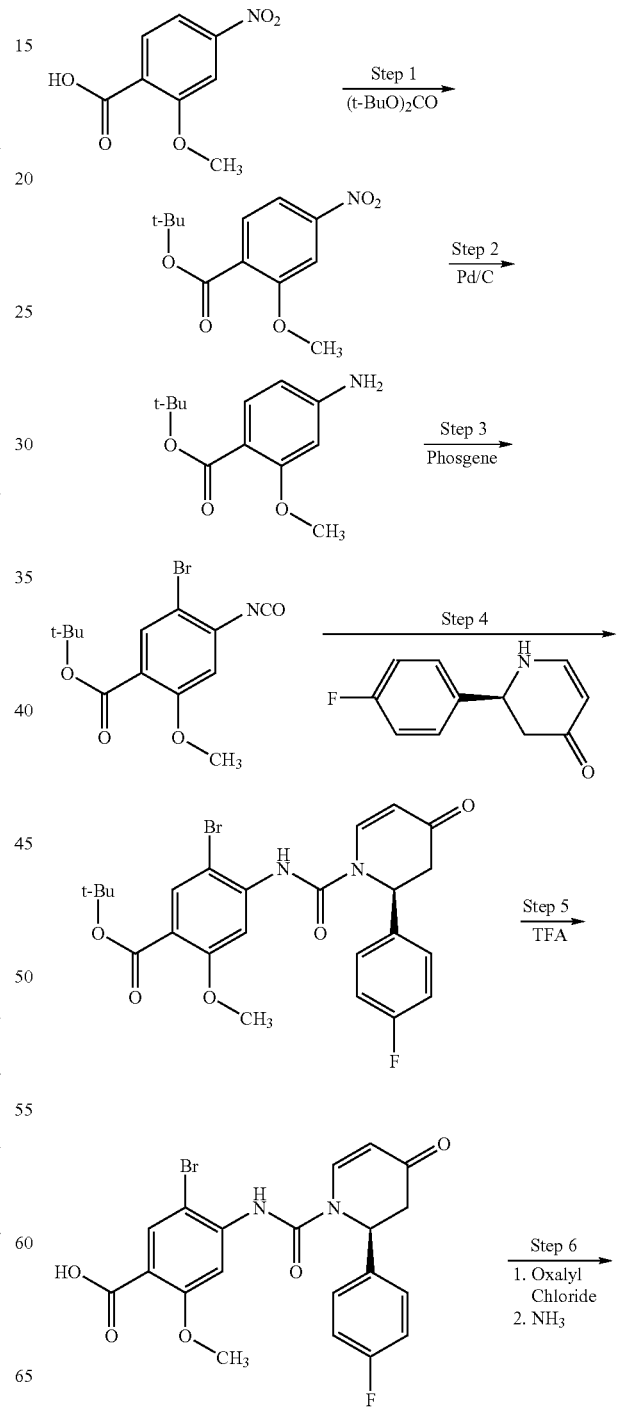

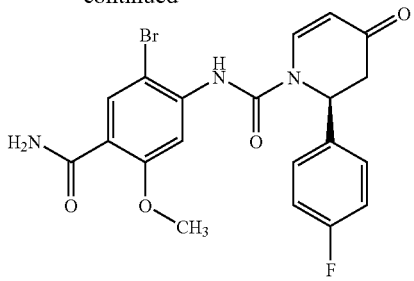

Step 1 tert-Butyl 4-nitro-2-methoxy benzoate

To 5 g 4-nitro-2-methoxy benzoic acid dissolved in 60 ml THF was added 0.84 g 4-(dimethylamino)pyridine and 20 g di-tent-butyl dicarbonate. The solution was stirred at room temperature for 72 hr under nitrogen, then poured into ice water. The pH of the mixture was adjusted to pH 10 with sodium carbonate, and the mixture was extracted with dichloromethane. The organic layer was dried over sodium sulfate, filtered and concentrated in vacuo. The residue was chromatographed over $SiO_2$ with 5% ethyl acetate in hexane to yield 6 g of tert-butyl 4-nitro-2-methoxy benzoate.

Step 2 tert-butyl 4-amino-2-methoxy-benzoate tert-Butyl 4-nitro-2-methoxy benzoate was dissolved in ethanol and 0.75 g 10% Pd on charcoal was added. The reaction mixture was stirred at room temperature under hydrogen at atmospheric pressure for 18 hours, then filtered through glass fiber paper to remove the catalyst. The filtrate was concentrated in vacuo to yield 3 g of tert-butyl 4-amino-2-methoxy-benzoate as a white powder.

Step 3 tert-butyl 4-isocyanato-2-methoxy-benzoate tert-Butyl 4-isocyanato-2-methoxy-benzoate was prepared from tert-butyl 4-amino-2-methoxy-benzoate and phosgene using the procedure of step 2 of Example 1.

Step 4 (S)-5-bromo-4-{[2-(4-fluoro-phenyl)-4-oxo-3,4-dihydro-2H-pyridine-1-carbonyl]-amino}-2-methoxy-benzoic acid tert-butyl ester (S)-5-bromo-4-{[2-(4-fluoro-phenyl)-4-oxo-3,4-dihydro-2H-pyridine-1-carbonyl]-amino}-2-methoxy-benzoic acid tert-butyl ester was prepared by reaction of tert-butyl 4-isocyanato-2-methoxy-benzoate with (S)-2-(4-Fluoro-phenyl)-2,3-dihydro-1H-pyridin-4-one following the procedure of step 3 of Example 1.

Step 5 (S)-5-bromo-4-{[2-(4-fluoro-phenyl)-4-oxo-3,4-dihydro-2H-pyridine-1-carbonyl]-amino}-2-methoxy-benzoic acid (S)-5-Bromo-4-{[2-(4-fluoro-phenyl)-4-oxo-3,4-dihydro-2H-pyridine-1-carbonyl]-amino}-2-methoxy-benzoic acid tert-butyl ester (170 mg) was stirred in 10 ml dichloromethane with 0.1 ml trifluoroacetic acid for 5 hours. Phosphate buffer (pH 7) was added, the layers separated, and the dichloromethane removed in vacuo. The residue was dissolved in acetone and recrystallized by slow addition of water. The crystals were filtered and dried to give 108 mg of (S)-5-bromo-4-{[2-(4-fluoro-phenyl)-4-oxo-3,4-dihydro-2H-pyridine-1-carbonyl]-amino}-2-methoxy-benzoic acid.

Step 6 (S)-5-bromo-4-{[2-(4-fluoro-phenyl)-4-oxo-3,4-dihydro-2H-pyridine-1-carbonyl]-amino}-2-methoxy-benzamide (S)-5-Bromo-4-{[2-(4-fluoro-phenyl)-4-oxo-3,4-dihydro-2H-pyridine-1-carbonyl]-amino}-2-methoxy-benzoic acid (72 mg) was dissolved in 2 ml dichloromethane and 0.001 ml dimethylformamide under argon. To this solution was added 0.02 ml oxalyl chloride and the solution was stirred for three hours. The solution was then slowly added at 0° C. to 0.5M $NH_3$ in dioxane. After stirring for 10 minutes, the mixture was concentrated in vacuo and chromatographed (dichloromethane) to yield 26 mg (S)-5-bromo-4-{[2-(4-fluoro-phenyl)-4-oxo-3,4-dihydro-2H-pyridine-1-carbonyl]-amino}-2-methoxy-benzamide. MS (M+H) 463.

Example 5

(S)-2-(4-Fluoro-phenyl)-4-oxo-3,4-dihydro-2H-pyridine-1-carboxylic acid [2-bromo-4-chloro-5-(2-hydroxy-ethoxy)-phenyl]-amide The synthetic procedure used in this example is outlined in Scheme I.

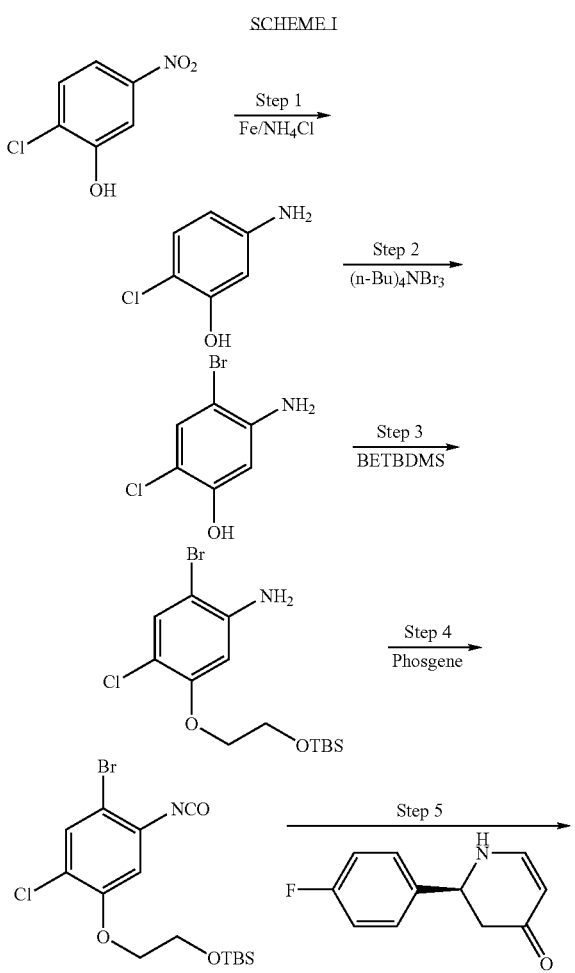

-continued

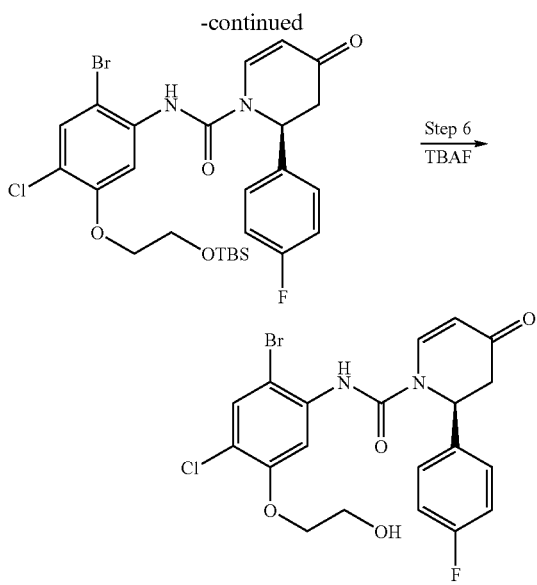

Step 1 5-Amino-2-chloro-phenol

To a solution of 2-chloro-5-nitrophenol (20.0 g, 115.2 mmol) in ethanol (150 ml) and water (150 ml) was added iron powder (32.2 g, 576.2 mmol) and ammonium chloride (32.1 g, 599.3 mmol). The mixture was heated at reflux for two hours, then cooled to room temperature and filtered. The filtrate was concentrated to dryness under reduced pressure. Purification of the residue by flash chromatography (hex:EtOAc/9:1) gave 5-amino-2-chloro-phenol (15.85 g, 96%) as a white solid.

Step 2 5-amino-4-bromo-2-chloro-phenol

To a solution of 5-amino-2-chloro-phenol (15.85 g, 110.4 mmol) in dichloromethane (300 ml) and MeOH (150 ml) was added tetrabutylammonium tribromide (58.6 g, 121.4 mmol). The mixture was stirred at room temperature for 20 minutes, and then was partitioned between saturated aqueous $Na_2SO_3$ and $Et_2O$. The organic layer was separated, washed with water and brine, dried over $MgSO_4$, filtered and concentrated to dryness under reduced pressure. Purification of the residue by flash chromatography (hex:EtOAc/7:3) gave 5-amino-4-bromo-2-chloro-phenol (4.38 g, 18%) as a white solid.

Step 3 2-bromo-5-[2-(tert-butyl-dimethyl-silanyloxy)-ethoxy]-4-chloro-phenylamine To a solution of 5-amino-4-bromo-2-chloro-phenol (0.338 g, 1.52 mmol) in NMP (5 ml) was added cesium carbonate (0.644 g, 1.97 mmol), sodium iodide (0.228 g, 1.52 mmol) and 2-bromoethoxy tertbutyldimethylsilane (0.424 g, 1.97 mmol). The mixture was heated to 100° C. for two hours, then cooled to room temperature. Water was added and the mixture was extracted with EtOAc. The combined organic extracts were washed with water and brine, dried over $MgSO_4$, filtered and concentrated to dryness under reduced pressure. Purification of the residue by flash chromatography (hex:EtOAc/8:2) gave 2-bromo-5-[2-(tert-butyl-dimethyl-silanyloxy)-ethoxy]-4-chloro-phenylamine (0.505 g, 78%) as a white solid.

Step 4 [2-(4-bromo-2-chloro-5-isocyanato-phenoxy)-ethoxy]-tert-butyl-dimethyl-silane To a solution of 2-bromo-5-[2-(tert-butyl-dimethyl-silanyloxy)-ethoxy]-4-chloro-phenylamine (0.15 g, 0.393 mmol) in toluene (3 ml) was added pyridine (0.038 ml, 0.472 mmol), DMAP (0.048 g, 0.393 mmol) and 20% phosgene in toluene (0.224 ml, 0.433 mmol). The mixture was stirred at room temperature for two hours. The mixture was filtered and the filtrate was concentrated to dryness under reduced pressure to give [2-(4-bromo-2-chloro-5-isocyanato-phenoxy)-ethoxy]-tert-butyl-dimethyl-silane (0.155 g) as a white solid, which was used directly in the next step.

Step 5 (S)-2-(4-Fluoro-phenyl)-4-oxo-3,4-dihydro-2H-pyridine-1-carboxylic acid {2-bromo-5-[2-(tert-butyl-dimethyl-silanyl)-ethoxy]-4-chloro-phenyl}-amide To a solution of (S)-2-(4-fluoro-phenyl)-2,3-dihydro-1H-pyridin-4-one (0.073 g, 0.381 mmol) in THF (3 ml) at −78° C. was added 2.5M n-BuLi in hexane (0.152 ml, 0.381 mmol). The mixture was stirred at −78° C. for 10 minutes. A solution of [2-(4-bromo-2-chloro-5-isocyanato-phenoxy)-ethoxy]-tert-butyl-dimethyl-silane (0.155 g, 0.381 mmol) in THF (2 ml) was added and the mixture was stirred at −78° C. for 30 minutes, and at room temperature for 30 minutes. Saturated aqueous ammonium chloride was added and the mixture was extracted with EtOAc. The combined organic extracts were washed with water and brine, dried over $MgSO_4$, filtered and concentrated to dryness. Purification of the residue by flash chromatography (hex:EtOAc/1:1) gave (S)-2-(4-Fluoro-phenyl)-4-oxo-3,4-dihydro-2H-pyridine-1-carboxylic acid {2-bromo-5-[2-(tert-butyl-dimethyl-silanyl)-ethoxy]-4-chloro-phenyl}-amide (0.198 g, 87%) as a white foam.

Step 6 (S)-2-(4-Fluoro-phenyl)-4-oxo-3,4-dihydro-2H-pyridine-1-carboxylic acid [2-bromo-4-chloro-5-(2-hydroxy-ethoxy)-phenyl]-amide To a solution of (S)-2-(4-Fluoro-phenyl)-4-oxo-3,4-dihydro-2H-pyridine-1-carboxylic acid {2-bromo-5-[2-(tert-butyl-dimethyl-silanyl)-ethoxy]-4-chloro-phenyl}-amide (0.095 g, 0.158 mmol) in THF (5 ml) was added 1.0 M TBAF in THF (0.35 ml, 0.348 mmol). The mixture was stirred at room temperature for three hours. Buffer (pH 2) was added and the mixture was extracted with EtOAc. The combined organic extracts were washed with water and brine, dried over $MgSO_4$, filtered and concentrated to dryness under reduced pressure. Purification of the residue by flash chromatography (hex:EtOAc/1:1) gave (S)-2-(4-fluoro-phenyl)-4-oxo-3,4-dihydro-2H-pyridine-1-carboxylic acid [2-bromo-4-chloro-5-(2-hydroxy-ethoxy)-phenyl]-amide (0.198 g) as a white foam. MS (M+H) 484.

In a similar fashion, the following compounds were prepared:
(S)-2-(3-Fluoro-phenyl)-4-oxo-3,4-dihydro-2H-pyridine-1-carboxylic acid [2-bromo-4-chloro-5-(2-hydroxy-ethoxy)-phenyl]-amide;
(S)-2-(4-Fluoro-phenyl)-4-oxo-3,4-dihydro-2H-pyridine-1-carboxylic acid [2-bromo-4-chloro-5-(3-methanesulfonyl-propoxy)-phenyl]-amide (in step 3, the alkylating agent used was toluene-4-sulfonic acid 3-methanesulfonyl-propyl ester, c.f. *J. Med. Chem.* 1995, 38, 2009);
(S)-2-(4-Fluoro-phenyl)-4-oxo-3,4-dihydro-2H-pyridine-1-carboxylic acid [2-bromo-4-chloro-5-(2-methoxy-ethoxy)-phenyl]-amide (1-bromo-2-methoxy-ethane used in step 3 in place of BETBDMS);
(S)-(4-Bromo-2-chloro-5-{[2-(4-fluoro-phenyl)-4-oxo-3,4-dihydro-2H-pyridine-1-carbonyl]-amino}-phenoxy)-acetic acid;

(S)-2-(4-Fluoro-phenyl)-4-oxo-3,4-dihydro-2H-pyridine-1-carboxylic acid (2-bromo-4-chloro-5-methylcarbamoylmethoxy-phenyl)-amide;

(S)-2-(4-Fluoro-phenyl)-4-oxo-3,4-dihydro-2H-pyridine-1-carboxylic acid (2-bromo-4-chloro-5-hydroxy-phenyl)-amide;

(S)-(4-Bromo-2-chloro-5-{[2-(4-fluoro-phenyl)-4-oxo-3,4-dihydro-2H-pyridine-1-carbonyl]-amino}-phenoxy)-acetic acid methyl ester (phenol from step 6 was alkylated with methyl bromoacetate);

(S)-(4-Bromo-2-chloro-5-{[2-(4-fluoro-phenyl)-4-oxo-3,4-dihydro-2H-pyridine-1-carbonyl]-amino}-phenoxy)-acetic acid; and (S)-2-(4-Fluoro-phenyl)-4-oxo-3,4-dihydro-2H-pyridine-1-carboxylic acid (2-bromo-4-chloro-5-methylcarbamoylmethoxy-phenyl)-amide (phenol of step 6 was alkylated with 2-chloro-N-methylacetamide).

Example 6

2-(4-fluoro-phenyl)-4-oxo-3,4-dihydro-2H-pyridine-1-carboxylic acid [2-bromo-4-chloro-5-(1-hydroxy-ethyl)-phenyl]-amide The synthetic procedure used in this example is outlined in Scheme J.

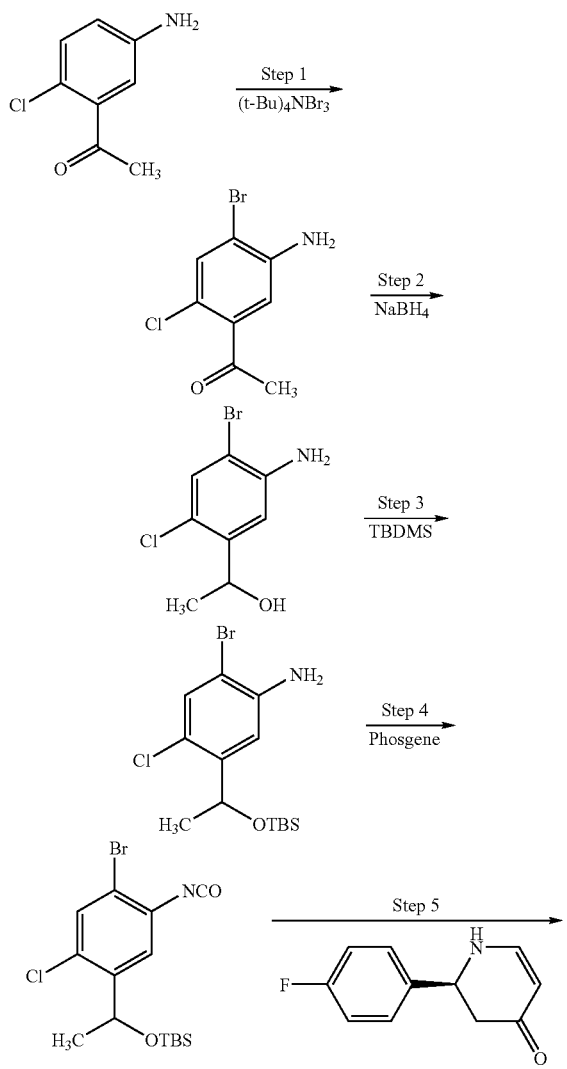

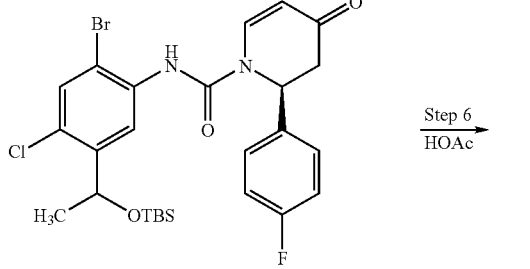

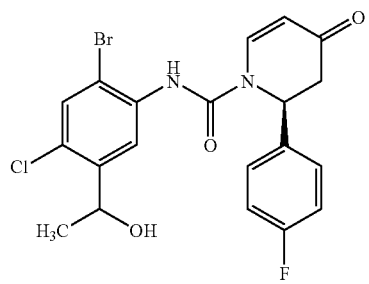

Step 1
1-(5-Amino-4-bromo-2-chloro-phenyl)-ethanone

To a solution of 1-(5-amino-2-chloro-phenyl)-ethanone (2.4 g, 14.15 mmol) in dichloromethane (30 ml) and MeOH (15 ml) was added tetrabutyl ammoniumetribromide (5.5 g, 11.3 mmol). The mixture was stirred at room temperature for 20 minutes, and then was partitioned between saturated aqueous $Na_2SO_3$ and $Et_2O$. The organic layer was separated, washed with water and brine, dried over $MgSO_4$, filtered and concentrated to dryness under reduced pressure. Purification of the residue by flash chromatography (hex:EtOAc/85:15) gave 1-(5-amino-4-bromo-2-chloro-phenyl)-ethanone (0.330 g, 9.5%) as a yellow solid.

Step 2
1-(5-Amino-4-bromo-2-chloro-phenyl)-ethanol

To a solution of 1-(5-amino-4-bromo-2-chloro-phenyl)-ethanone (0.25 g, 1.00 mmol) in methanol (5 ml) was added $NaBH_4$ (0.076 g, 2.01 mmol). The mixture was stirred at room temperature for two hours, then quenched by addition of 2N HCl and taken to neutral pH with pH7 buffer. The mixture was extracted with dichloromethane, and the combined organic layers were washed with water and brine, dried over $MgSO_4$, filtered and concentrated to dryness under reduced pressure. Purification of the residue by flash chromatography (hex:EtOAc/7:3) gave 1-(5-amino-4-bromo-2-chloro-phenyl)-ethanol 0.195 g (77%) as a clear oil.

Step 3 5-[1-(tert-butyl-dimethyl-silanyloxy)-ethyl]-4-chloro-phenylamine

To a solution of 1-(5-amino-4-bromo-2-chloro-phenyl)-ethanol (0.195 g, 0.778 mmol) in DMF (3 ml) was added tert-butyl-dimethylsilyl chloride (0.152 g, 1.011 mmol) and imidazole (0.069 g, 1.011 mmol). The mixture was stirred at room temperature for six hours. Water was added and the mixture was extracted with EtOAc. The combined organic extracts were washed with water and brine, dried over MgSO4, filtered and concentrated to dryness under reduced pressure. Purification of the residue by flash chromatography (hex:EtOAc/9:1) gave 2-bromo-5-[1-(tert-butyl-dimethyl-silanyloxy)-ethyl]-4-chloro-phenylamine (0.262 g, 92%) as a clear oil.

Step 4 1-(4-Bromo-2-chloro-5-isocyanato-phenyl)-ethoxy]-tert-butyl-dimethyl-silane 1-(4-Bromo-2-chloro-5-isocyanato-phenyl)-ethoxy]-tert-butyl-dimethyl-silane was prepared from 2-bromo-5-[1-(tert-butyl-dimethyl-silanyloxy)-ethyl]-4-chloro-phenylamine using the procedure of step 4 of Example 5.

Step 6 2-(4-Fluoro-phenyl)-4-oxo-3,4-dihydro-2H-pyridine-1-carboxylic acid {2-bromo-5-[1-(tert-butyl-dimethyl-silanyloxy)-ethyl]-4-chloro-phenyl}-amide 2-Bromo-5-[1-(tert-butyl-dimethyl-silanyloxy)-ethyl]-4-chloro-phenylamine was reacted with (S)-2-(4-fluoro-phenyl)-2,3-dihydro-1H-pyridin-4-one using the procedure of step 5 of Example 5 to give 2-(4-Fluoro-phenyl)-4-oxo-3,4-dihydro-2H-pyridine-1-carboxylic acid {2-bromo-5-[1-(tert-butyl-dimethyl-silanyloxy)-ethyl]-4-chloro-phenyl}-amide.

Step 6 2-(4-fluoro-phenyl)-4-oxo-3,4-dihydro-2H-pyridine-1-carboxylic acid [2-bromo-4-chloro-5-(1-hydroxy-ethyl)-phenyl]-amide A mixture of acetic acid (4.5 ml), water (1.5 ml) and THF (1.5 ml) was added to a flask containing 2-(4-fluoro-phenyl)-4-oxo-3,4-dihydro-2H-pyridine-1-carboxylic acid {2-bromo-5-[1-(tert-butyl-dimethyl-silanyloxy)-ethyl]-4-chloro-phenyl}-amide (0.144 g, 0.247 mmol). The mixture was stirred at room temperature for 16 hours. Water was added and the mixture was extracted with EtOAc. The combined organic extracts were washed with water and brine, dried over MgSO$_4$, filtered and concentrated to dryness under reduced pressure. Purification by flash chromatography (EtOAc) gave 2-(4-fluoro-phenyl)-4-oxo-3,4-dihydro-2H-pyridine-1-carboxylic acid [2-bromo-4-chloro-5-(1-hydroxy-ethyl)-phenyl]-amide (0.082 g, 71%) as a white foam. MS (M+H) 468.

Example 7

2-(4-Fluoro-phenyl)-4-oxo-3,4-dihydro-2H-pyridine-1-carboxylic acid (2-bromo-4-chloro-5-methane-sulfonyl-phenyl)-amide The synthetic procedure used in this example is outlined in Scheme K.

SCHEME K

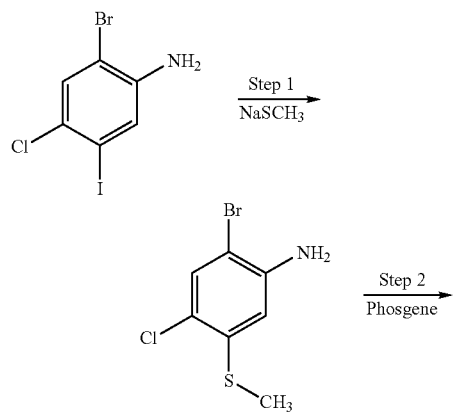

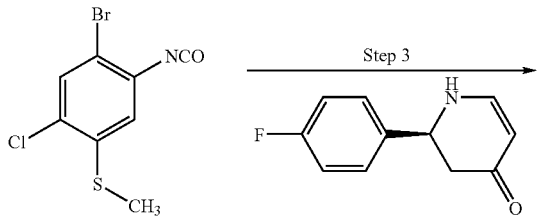

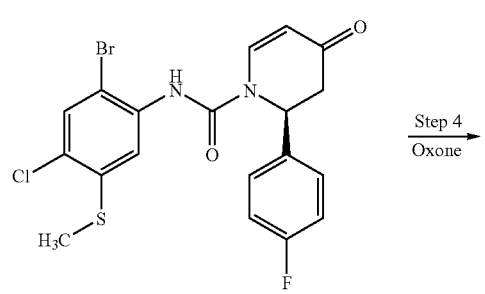

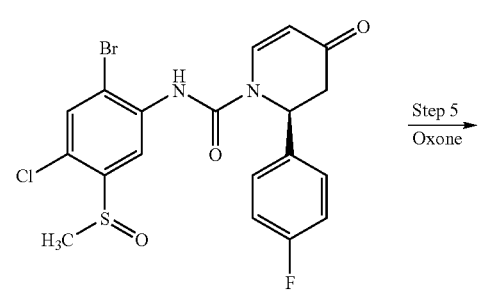

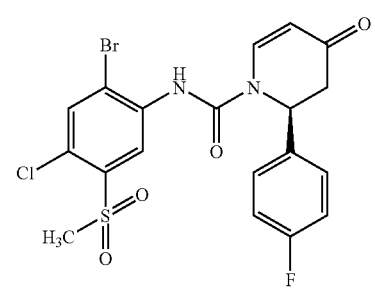

Step 1
2-Bromo-4-chloro-5-methylsulfanyl-phenylamine

To a solution of 2-bromo-4-chloro-5-iodo-phenylamine (0.573 g, 1.72 mmol) in dioxane (10 ml) was added Pd$_2$(dba)$_3$ (0.197 g, 0.2155 mmol), Xantphos (0.249 g, 0.431 mmol), Hunig base (0.60 ml, 3.448 mmol) and sodium thiomethoxide (0.133 g, 1.72 mmol). The mixture was heated at 80° C. for 6 hours. The mixture was cooled to room temperature and pH2 buffer was added. The mixture was extracted with EtOAc, and the combined organic layers were washed with water and brine, dried over MgSO$_4$, filtered and concentrated to dryness under reduced pressure. Purification of the residue by flash chromatography (hex:EtOAc/7:3) gave 2-bromo-4-chloro-5-methylsulfanyl-phenylamine (0.22 g, 50%) as an oil.

Step 2 1-Bromo-5-chloro-2-isocyanato-4-methylsulfanyl-benzene

To a solution of 2-bromo-4-chloro-5-methylsulfanyl-phenylamine (0.10 g, 0.396 mmol) in toluene (3 ml) was added pyridine (0.042 ml, 0.515 mmol), DMAP (0.048 g, 0.396 mmol) and 20% phosgene in toluene (0.225 ml, 0.436 mmol). The mixture was stirred at room temperature for two hours, then filtered. The filtrate was concentrated to dryness to give 1-bromo-5-chloro-2-isocyanato-4-methylsulfanyl-benzene (0.095 g) as a white solid that was used directly in the next step.

Step 3 (S)-2-(4-Fluoro-phenyl)-4-oxo-3,4-dihydro-2H-pyridine-1-carboxylic acid (2-bromo-4-chloro-5-methylsulfanyl-phenyl)-amide To a solution of (S)-2-(4-fluoro-phenyl)-2,3-dihydro-1H-pyridin-4-one (0.065 g, 0.341 mmol) in THF (3 ml) was added at −78 C 2.5M n-BuLi in hexane (0.150 ml, 0.341 mmol). The mixture was stirred at −78 C for 10 min. A solution of above isocyanate (0.095 g, 0.341 mmol) in THF (2 ml) was added and the mixture was stirred at −78 C for 30 min and at rt for 30 min. Sat. ammonium chloride was added and the product was extracted with EtOAc (3×). The extract was washed with water, brine dried over MgSO$_4$ and concentrated to dryness. Purification by flash chromatography (hex: EtOAc/1:1) gave (S)-2-(4-fluoro-phenyl)-4-oxo-3,4-dihydro-2H-pyridine-1-carboxylic acid (2-bromo-4-chloro-5-methylsulfanyl-phenyl)-amide (0.130 g, 81%) as a white foam.

Step 4 2-(4-Fluoro-phenyl)-4-oxo-3,4-dihydro-2H-pyridine-1-carboxylic acid (2-Bromo-4-chloro-5-methanesulfinyl-phenyl)-amide To a solution of 2-(4-fluoro-phenyl)-4-oxo-3,4-dihydro-2H-pyridine-1-carboxylic acid (2-bromo-4-chloro-5-methylsulfanyl-phenyl)-amide (0.070 g, 0.149 mmol) in methanol (2 ml) and acetonitrile (2 ml) was added oxone (potassium peroxymonosulfate, 0.064 g, 0.104 mmol) and water (0.3 ml). The mixture was stirred at room temperature for two hours. Water was added and the mixture was extracted with EtOAc. The organic extract was washed with water and brine, dried over MgSO$_4$, filtered and concentrated to dryness under reduced pressure. Purification of the residue by flash chromatography (EtOAc) gave 0.020 g and 0.021 g of the two diasteriomers 2-(4-fluoro-phenyl)-4-oxo-3,4-dihydro-2H-pyridine-1-carboxylic acid (2-bromo-4-chloro-5-methanesulfinyl-phenyl)-amide as white foams.

Step 5 2-(4-Fluoro-phenyl)-4-oxo-3,4-dihydro-2H-pyridine-1-carboxylic acid (2-bromo-4-chloro-5-methanesulfonyl-phenyl)-amide To a solution of 2-(4-fluoro-phenyl)-4-oxo-3,4-dihydro-2H-pyridine-1-carboxylic acid (2-bromo-4-chloro-5-methylsulfanyl-phenyl)-amide (0.050 g, 0.106 mmol) in methanol (2 ml) and acetonitrile (2 ml) was added oxone (0.131 g, 0.213 mmol) and water (0.3 ml). The mixture was stirred at room temperature for two hours. Water was added and the mixture was extracted with EtOAc. The organic extract was washed with water and brine, dried over MgSO$_4$, filtered and concentrated to dryness under reduced pressure. Purification of the residue by flash chromatography (EtOAc) gave 2-(4-fluoro-phenyl)-4-oxo-3,4-dihydro-2H-pyridine-1-carboxylic acid (2-bromo-4-chloro-5-methanesulfonyl-phenyl)-amide (0.009 g) as a white foam. MS (M+H) 502.

Example 8

4-Oxo-3,4-dihydro-2H-[2,3']bipyridinyl-1-carboxylic acid (2-bromo-5-methoxy-4-methyl-phenyl)-amide The synthetic procedure used in this example is outlined in Scheme L.

SCHEME L

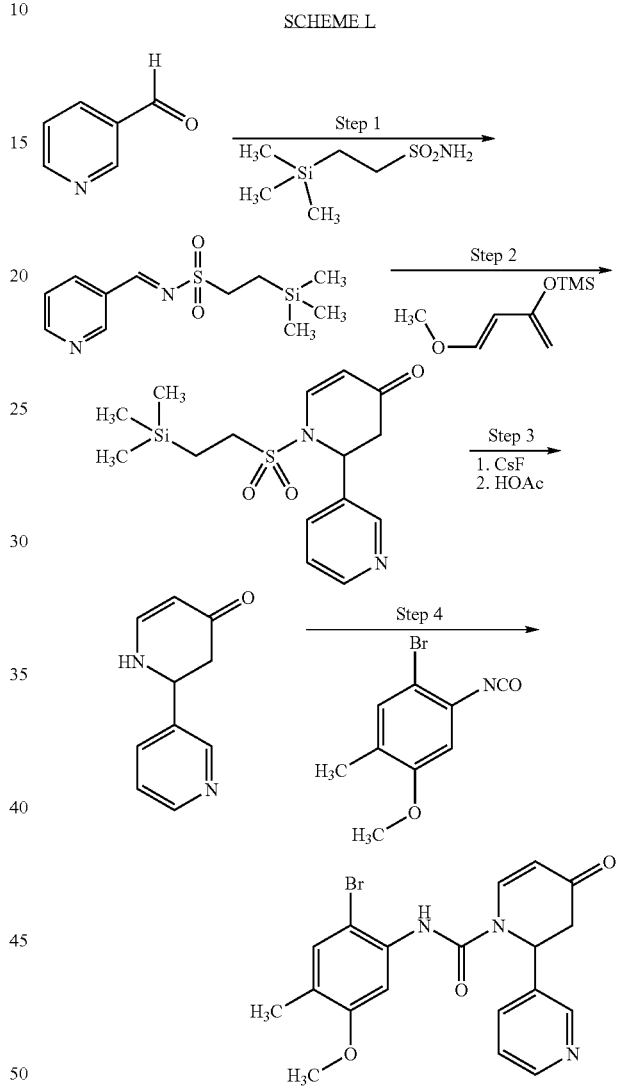

Step 1 2-Trimethylsilyl-ethanesulfonic acid pyridin-3-ylmethyleneamide

To a solution of 3-formylpyridine (0.228 mL, 2.42 mmol) and 2-(trimethylsilyl)ethanesulfonamide (0.438 g, 2.42 mmol) in toluene (30 mL) was added boron trifluoride etherate (0.02 mL, 0.15 mmol) under Ar. The mixture was heated at reflux for 20 hours using a Dean-Stark trap. After cooling, 10% aqueous sodium bicarbonate was added, and the mixture was extracted with ethyl acetate. The combined organic extracts were washed with brine, dried (Na$_2$SO$_4$), filtered and concentrated to dryness to under reduced pressure obtain crude 2-trimethylsilyl-ethanesulfonic acid pyridin-3-ylmethyleneamide (669 mg), which was used directly in the next step.

Step 2 1-(2-Trimethylsilyl-ethanesulfonyl)-2,3-dihydro-1H-[2,3']bipyridinyl-4-one To a solution of 2-trimethylsilyl-ethanesulfonic acid pyridin-3-ylmethyleneamide (665 mg) in toluene (4.5 mL) was added Danishefsky's diene (0.46 mL, 2.4 mmol) under Ar atmosphere. The mixture was heated at reflux for 90 minutes. The toluene was removed in vacuo and the residue was dissolved in dichloromethane (ca. 10 mL) and treated with 2N HCl (ca. 10 mL) for 5 minutes. 10% Aqueous sodium bicarbonate was added carefully to adjust to pH 8. The phases were separated and the aqueous phase was extracted with dichloromethane. The combined organic extracts were dried ($Na_2SO_4$), filtered and evaporated to dryness under reduced pressure. Purification of the residue by flash chromatography (gradient hexane/ethyl acetate) gave 1-(2-trimethylsilyl-ethanesulfonyl)-2,3-dihydro-1H-[2,3']bipyridinyl-4-one (322 mg, 40% overall).

Step 3 2,3-Dihydro-1H-[2,3']bipyridinyl-4-one

To a solution of 1-(2-trimethylsilyl-ethanesulfonyl)-2,3-dihydro-1H-[2,3']bipyridinyl-4-one (106.1 mg, 0.31 mmol) in DMF (0.5 mL) was added cesium fluoride (153.5 mg, 1.0 mmol) under Ar atmosphere. The mixture was heated at 90° C. for 2 hours, then cooled to room temperature. Acetic acid (0.062 mL, 1.085 mmol) was added, and the mixture was diluted with ethyl acetate and filtered. The filtrate was taken to dryness under reduced pressure. Purification of the residue by flash chromatography (dichloromethane/methanol 95:5) gave 2,3-dihydro-1H-[2,3']bipyridinyl-4-one (51 mg, 93.5%).

Step 4 4-oxo-3,4-dihydro-2H-[2,3']bipyridinyl-1-carboxylic acid (2-bromo-5-methoxy-4-methyl-phenyl)-amide 2,3-Dihydro-1H-[2,3']bipyridinyl-4-one was reacted with 1-bromo-2-isocyanato-4-methoxy-5-methyl-benzene using the procedure of step 3 of Example 1 to afford 4-oxo-3,4-dihydro-2H-[2,3']bipyridinyl-1-carboxylic acid (2-bromo-5-methoxy-4-methyl-phenyl)-amide, MS (M+H) 417.

In a similar fashion, the following compounds were prepared:
2-(2-Chloro-phenyl)-4-oxo-3,4-dihydro-2H-pyridine-1-carboxylic acid (2-bromo-5-methoxy-4-methyl-phenyl)-amide; and
2-(2-Fluoro-phenyl)-4-oxo-3,4-dihydro-2H-pyridine-1-carboxylic acid (2-bromo-5-methoxy-4-methyl-phenyl)-amide.

Example 9

(S)-2-(4-fluoro-phenyl)-4-oxo-3,4-dihydro-2H-pyridine-1-carboxylic acid (3-bromo-6-methoxy-pyridin-2-yl)-amide The synthetic procedure used in this example is outlined in Scheme M.

SCHEME M

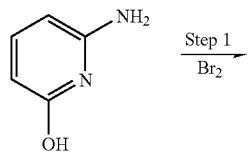

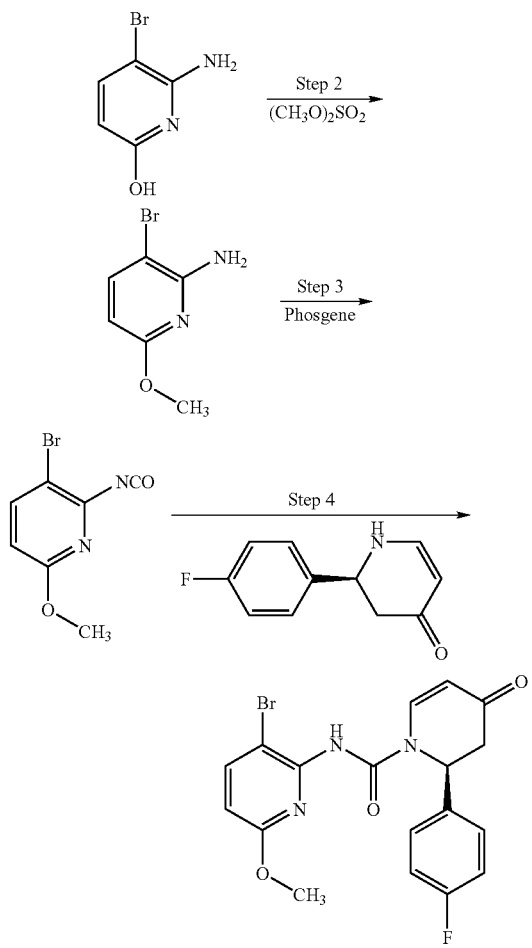

Step 1 6-Amino-5-bromo-pyridin-2-ol

To a solution of 6-amino-pyridin-2-ol (5 g, 45.4 mmol) in glacial acetic acid (60 mL) was added bromine (2.33 mL, 45.4 mmol) under Ar atmosphere. The mixture was stirred for 20 minutes, then water was added and the mixture was extracted with ethyl acetate. The combined organic extracts were washed with brine, dried ($Na_2SO_4$), filtered and concentrated to dryness to obtain crude 6-amino-5-bromo-pyridin-2-ol (4.53 g).

Step 2 3-bromo-6-methoxy-pyridin-2-ylamine

To a solution of 6-amino-5-bromo-pyridin-2-ol (1.0 g) in DMF (30 mL) was added at 0° C. 0.5 M potassium bis(trimethylsilyl)amide in toluene (11.7 mL, 5.83 mmol) under Ar atmosphere. After stirring for 10 minutes, dimethyl sulfate (0.64 mL, 5.26 mmol) was added at 0° C. The mixture was allowed to warm to room temperature, and was stirred for an additional two hours. Buffer (pH 7) was added and mixture was extracted with diethyl ether. The combined organic extracts were washed with brine, dried ($Na_2SO_4$), filtered and concentrated to dryness. Purification of the residue by flash chromatography (hexane/toluene 45:55) gave pure 3-bromo-6-methoxy-pyridin-2-ylamine (260 mg, 13% overall).

Step 3 3-Bromo-2-isocyanato-6-methoxy-pyridine

3-Bromo-2-isocyanato-6-methoxy-pyridine was prepared by reaction of 3-bromo-6-methoxy-pyridin-2-ylamine with phosgene using the procedure of step 2 of Example 1.

Step 4 (S)-2-(4-fluoro-phenyl)-4-oxo-3,4-dihydro-2H-pyridine-1-carboxylic acid (3-bromo-6-methoxy-pyridin-2-yl)-amide (S)-2-(4-fluoro-phenyl)-4-oxo-3,4-dihydro-2H-pyridine-1-carboxylic acid (3-bromo-6-methoxy-pyridin-2-yl)-amide was prepared by reaction of 3-bromo-2-isocyanato-6-methoxy-pyridine with (S)-2-(4-fluoro-phenyl)-2,3-dihydro-1H-pyridin-4-one using the procedure of step 3 of Example 1. MS (M+H) 421.

Example 10

(S)-2-(4-fluoro-phenyl)-4-oxo-3,4-dihydro-2H-pyridine-1-carboxylic acid (2-bromo-4-methanesulfonyl-5-methoxy-phenyl)-amide The synthetic procedure used in this example is outlined in Scheme N.

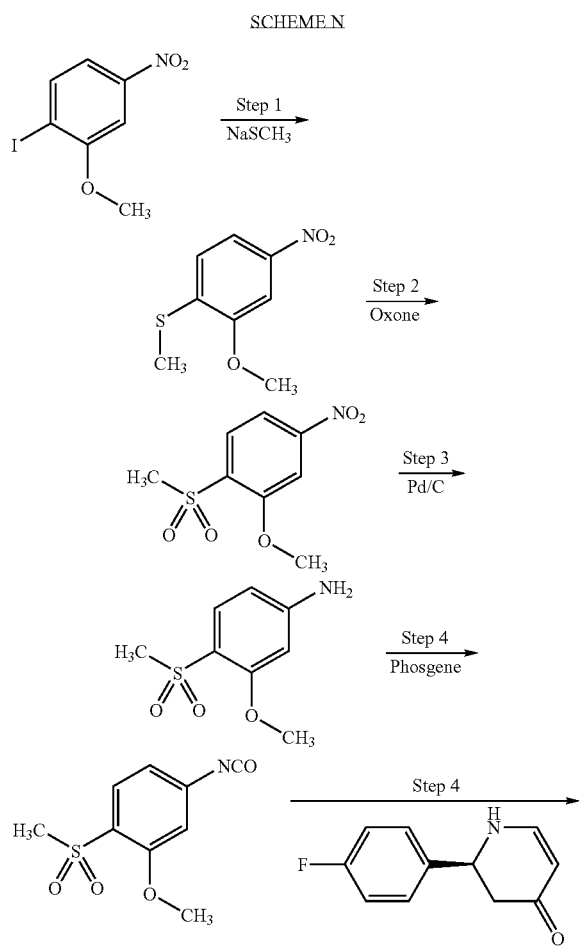

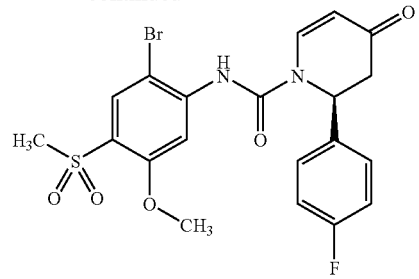

Step 1 2-Methoxy-1-methylsulfanyl-4-nitro-benzene

2-Iodo-5-nitroanisole (5.58 g, 20.0 mmol), $Pd_2(dba)_3$ (0.025 eq, 457 mg), Xantphos (0.05 eq, 578 mg), Hunigs Base (1 eq, 3.48 ml) and sodium methanethiolate (1 eq, 1.40 g) were dissolved in THF. The mixture was heated to reflux overnight. Upon cooling the mixture was filtered through celite. The filtrate was concentrated in vacuo. The residue was purified by flash chromatography (4:1 Hexanes/Ethyl Acetate) to give 2-methoxy-1-methylsulfanyl-4-nitro-benzene (2.72 g, 68.3%) as a yellow crystalline solid.

Step 2 1-Methanesulfonyl-2-methoxy-4-nitro-benzene

2-Methoxy-1-methylsulfanyl-4-nitro-benzene (797 mg, 4.0 mmol) was dissolved in methanol (10 ml) and acetonitrile (10 ml). A solution of Oxone (1.5 eq, 3.7 g) in 8 ml of water was added and the mixture was allowed to stir at room temperature for 4 hours. The reaction mixture was diluted with water and extracted with EtOAc. The combined organic extracts were washed with brine, dried over anhydrous sodium sulfate, filtered and concentrated in vacuo to give 1-methanesulfonyl-2-methoxy-4-nitro-benzene (631 mg, 68.2%) as a yellow crystalline solid.

Step 3 4-Methanesulfonyl-3-methoxy-phenylamine

4-Methanesulfonyl-3-methoxy-phenylamine was prepared by reduction of 1-methanesulfonyl-2-methoxy-4-nitro-benzene following the procedure of step 5 of Example 3.

Step 4 4-Isocyanato-1-methanesulfonyl-2-methoxy-benzene

4-Isocyanato-1-methanesulfonyl-2-methoxy-benzene was prepared by reaction of 4-methanesulfonyl-3-methoxy-phenylamine with phosgene following the procedure of step 6 of Example 3.

Step 5 (S)-2-(4-fluoro-phenyl)-4-oxo-3,4-dihydro-2H-pyridine-1-carboxylic acid (2-bromo-4-methanesulfonyl-5-methoxy-phenyl)-amide (S)-2-(4-fluoro-phenyl)-4-oxo-3,4-dihydro-2H-pyridine-1-carboxylic acid (2-bromo-4-methanesulfonyl-5-methoxy-phenyl)-amide was prepared by reaction of 4-isocyanato-1-methanesulfonyl-2-methoxy-benzene with (S)-2-(4-Fluoro-phenyl)-2,3-dihydro-1H-pyridin-4-one following the procedure of step 7 of Example 3.

Example 11

(S)-2-(4-Fluoro-phenyl)-4-oxo-3,4-dihydro-2H-pyridine-1-carboxylic acid (2-bromo-5-methoxy-4-trifluoromethyl-phenyl)-amide The synthetic procedure used in this example is outlined in Scheme O.

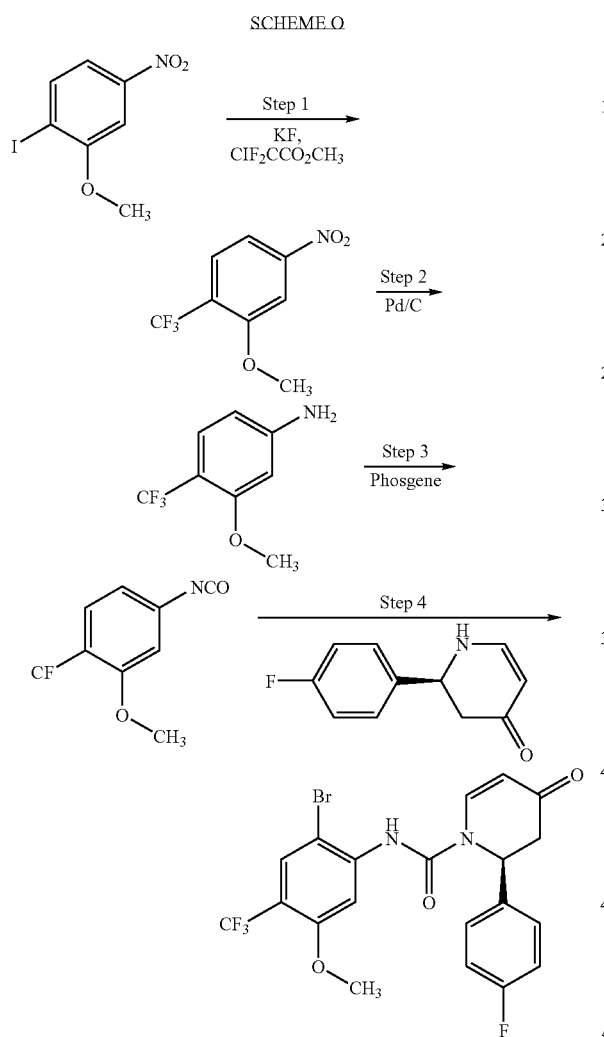

Step 1 2-Methoxy-4-nitro-1-trifluoromethyl-benzene

Following the procedure reported in *JACS* 2003, 125, 12502, 2-iodo-5-nitroanisole (2.79 g, 10.0 mmol), copper(I) iodide (2.2 eq, 4.19 g), and potassium fluoride (2.2 eq, 1.28 g) were dissolved in DMF. $ClF_2CCO_2CH_3$ (4.4 eq, 4.7 ml) was added and the mixture was heated to 120° C. overnight. Upon cooling, the mixture was diluted with water and diethyl ether and filtered through celite. The combined organic extracts were dried over anhydrous sodium sulfate, filtered and concentrated in vacuo. The residue was purified by flash chromatography (gradient 9:1 to 1:1 Hexanes/Ethyl Acetate) to give 2-methoxy-4-nitro-1-trifluoromethyl-benzene (1.13 g, 51.1%) as a yellow oil.

Step 2 3-Methoxy-4-trifluoromethyl-phenylamine

3-Methoxy-4-trifluoromethyl-phenylamine was prepared by reduction of 2-methoxy-4-nitro-1-trifluoromethyl-benzene using the procedure of step 5 of Example 3.

Step 3 4-Isocyanato-2-methoxy-1-trifluoromethyl-benzene

4-Isocyanato-2-methoxy-1-trifluoromethyl-benzene was prepared by reaction of 3-methoxy-4-trifluoromethyl-phenylamine with phosgene following the procedure of step 6 of Example 3.

Step 4 (S)-2-(4-Fluoro-phenyl)-4-oxo-3,4-dihydro-2H-pyridine-1-carboxylic acid (2-bromo-5-methoxy-4-trifluoromethyl-phenyl)-amide (S)-2-(4-Fluoro-phenyl)-4-oxo-3,4-dihydro-2H-pyridine-1-carboxylic acid (2-bromo-5-methoxy-4-trifluoromethyl-phenyl)-amide was prepared from 4-isocyanato-2-methoxy-1-trifluoromethyl-benzene and (S)-2-(4-fluoro-phenyl)-2,3-dihydro-1H-pyridin-4-one following the procedure of step 7 of Example 3.

Example 12

(S)-2-(4-Fluoro-phenyl)-4-oxo-3,4-dihydro-2H-pyridine-1-carboxylic acid (2-bromo-5-methoxy-4-trifluoromethyl-phenyl)-amide The synthetic procedure used in this example is outlined in Scheme P.

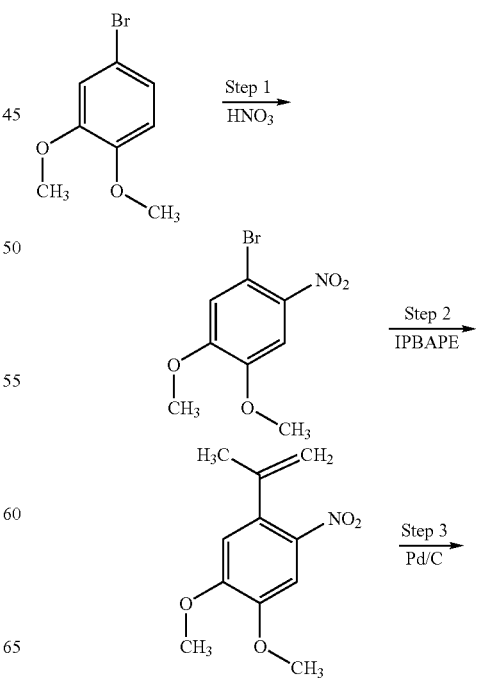

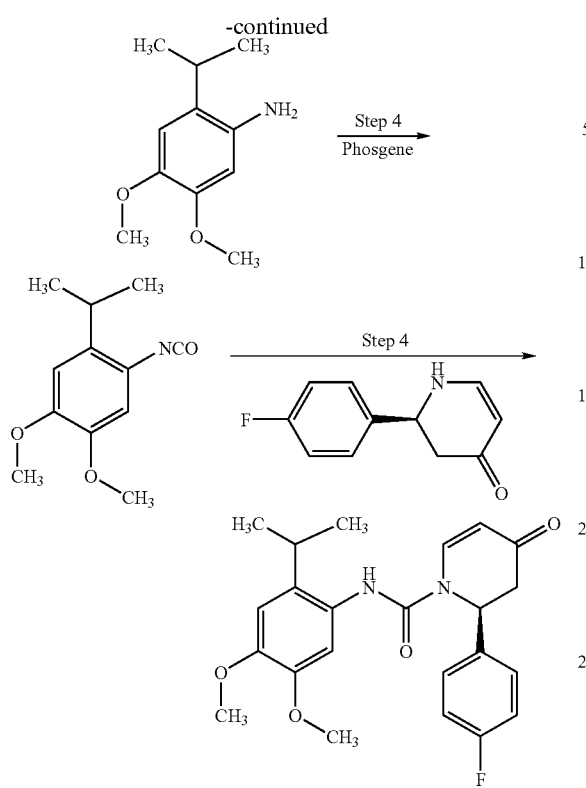

Step 1 1-Bromo-4,5-dimethoxy-2-nitro-benzene

Following the procedure of *J. Org. Chem.* 1960, 25, 721) 4-Bromoveratrole (16.28 g, 75.0 mmol) was slowly added to a stirred solution of concentrated nitric acid (122 ml) and acetic acid (365 ml) maintained at 10° C. The reaction mixture was stirred at 15° C. for one hour, then was diluted with water and extracted with diethyl ether. The combined organic extracts were dried over anhydrous sodium sulfate, filtered and concentrated in vacuo. The residue was crystallized from ethanol to give 1-bromo-4,5-dimethoxy-2-nitro-benzene (13.144 g, 66.9%) as yellow crystals.

Step 2 1-Isopropenyl-4,5-dimethoxy-2-nitro-benzene

1-Bromo-4,5-dimethoxy-2-nitro-benzene (6.55 g, 25.0 mmol), potassium carbonate (2 eq, 6.91 g) and tetrakis(triphenylphosphine)palladium(0) (0.125 eq, 3.61 g) were dissolved in dioxane. Isopropenylboronic acid pinacol ester (1 eq, 4.7 ml) was added and the mixture was heated to 100° C. overnight. Upon cooling the mixture was filtered through celite. The filtrate was concentrated in vacuo, and the residue was purified by flash chromatography (gradient 9:1 to 1:1 Hexanes/Ethyl Acetate) to give 1-isopropenyl-4,5-dimethoxy-2-nitro-benzene (1.59 g, 28.5%) as a yellow oil.

Step 3 2-Isopropyl-4,5-dimethoxy-phenylamine

1-Isopropenyl-4,5-dimethoxy-2-nitro-benzene (446 mg, 2.0 mmol) was dissolved in 50 ml of methanol at room temperature. 10% Palladium on Carbon (200 mg) was added and the mixture was stirred under a balloon of hydrogen overnight. The mixture was filtered through celite. The filtrate was concentrated in vacuo, and the residue was purified by flash chromatography (4:1 Hexanes/Ethyl Acetate) to give 2-isopropyl-4,5-dimethoxy-phenylamine (369 mg, 94.6%) as a tan oil.

Step 4
1-Isocyanato-2-isopropyl-4,5-dimethoxy-benzene

1-Isocyanato-2-isopropyl-4,5-dimethoxy-benzene was prepared by reaction of 2-isopropyl-4,5-dimethoxy-phenylamine with phosgene following the procedure of step 2 of Example 1.

Step 5 (S)-2-(4-fluoro-phenyl)-4-oxo-3,4-dihydro-2H-pyridine-1-carboxylic acid (2-isopropyl-4,5-dimethoxy-phenyl)-amide 1-Isocyanato-2-isopropyl-4,5-dimethoxy-benzene was reacted with (S)-2-(4-fluoro-phenyl)-2,3-dihydro-1H-pyridin-4-one following the procedure of step 3 of Example 1.

Example 13

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
|---|---|
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
|---|---|
| Active compound | 0.2-2 |
| Span 60 | 2 |
| Tween 60 | 2 |
| Mineral oil | 5 |
| Petrolatum | 10 |

| Ingredients | Grams |
|---|---|
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 14

Intracellular Calcium Flux (FLIPR) Assay

Compound and Reagent Preparation

Stock solutions of compounds were prepared from powders as a 10 mM DMSO stock solution. These solutions were stored at RT during the two week period of these experiments to prevent freeze-thaw of the DMSO stocks. The DMSO stocks were added to the appropriate assay buffer at a concentration of 10 µM, and then diluted serially to the final concentrations that were tested. No observable precipitate was formed at any time during this process. The aqueous solutions of compounds as well as ATP (Sigma A7699) and BzATP (Sigma B6396) were prepared fresh for each day of experiment.

Cell culture: 1321N1-hP2X$_7$ and HEK293-rP2X$_7$

1321N1 cells stably expressing the full length human P2X$_7$ gene (1321N1-hP2X$_7$) and HEK293 cells stably expressing the full length rat P2X$_7$ gene (HEK293-rP2X$_7$) were obtained from the Roche Cell Culture Facility. 1321N1-hP2X$_7$ cells were grown in Dulbecco's Modified Eagle's Medium (DMEM) high glucose supplemented with 10% FBS and 250 µg/mL G418. HEK293-rP2X$_7$ cells were grown in DMEM/F-12 supplemented with 10% FBS, 1 mM CaCl$_2$, 2 mM MgCl$_2$, 2 mM L-Glutamine and 500 µg/ml G418. Cells were split such that they never became >70% confluent.

Intracellular Calcium Flux (FLIPR)

On the day prior to the experiment, 1321N1-hP2X$_7$ or HEK293-rP2X$_7$ cells were released into suspension with calcium-free PBS+Versene and washed by centrifugation with calcium-free PBS to remove the Versene. Cells were resuspended in growth medium at a density of $2.5 \times 10^5$ cells/mL and seeded into black walled, clear bottom 96 well plates (50,000 cells/well) approximately 18 hr prior to intracellular calcium flux experiments.

On the day of the experiment, plates were washed with FLIPR buffer (calcium- and magnesium-free Hank's Balanced Salt Solution (HBSS) supplemented with 10 mM Hepes, 2.5 mM probenecid and 2 mM calcium chloride)

using a BIO-TEK 96 channel plate washer and incubated with 2 mM fluo-3 dye at 37° C. for one hr. The dye was then removed by plate washing and the cells were allowed to equilibrate for 20 min at room temperature with antagonist or vehicle (FLIPR buffer). Agonist (100 µM BzATP final concentration for hP2X$_7$; 5 µM BzATP final concentration or rP2X$_7$) was added online with the FLIPR and fluorescence measurements made at 1 sec intervals for 60 sec followed by 3 sec intervals for a further 4 min (5 min total). A final addition of 5 µM ionomycin was made and the maximal BzATP-evoked fluorescence normalized to the maximal ionomycin-evoked fluorescence.

Example 14

Human Whole Blood IL-1β Release Assay

Compound & Reagent Preparation 10 mM stock solutions of compounds in DMSO (Sigma D2650) were prepared and used either fresh or after storage at −20° C. Appropriate (200×) serial dilutions of the compounds were made in DMSO, then freshly diluted 1 to 20 (10×) with Dulbecco's phosphate buffered saline (DPBS; Mediatech Inc., 21-030), such that final DMSO concentration in the blood always equaled 0.5%.

30 mM ATP (Sigma A7699) was prepared immediately before use in 50 mM HEPES (Gibco 15630) and the pH adjusted to 7.2 with 1M sodium hydroxide.

Blood Donors

Human blood donors were medication free and restricted from utilizing alcohol or caffeine for at least the 24 hr preceding collection. The blood was collected into sodium heparin vacutainer tubes and used the same day.

Assay Method

The OptEIA Human IL-1β ELISA Set, OptEIA Coating Buffer, Assay Diluent and TMB Substrate Reagent Set used in the assay were commercially obtained from BD Pharmingen. Blood was diluted 1:1 with Dulbecco's PBS, LPS (Escherichia Coli 0127:B8, Sigma L3129) added to a final concentration of 25 ng/mL and incubated for 2 hr at 37° C. 48 µL of this LPS primed blood was added to 6 µL of the 10× compound in 5% DMSO/PBS in the appropriate well of a 96-well polypropylene plate. The blood and compound were mixed and allowed to incubate for 30 min at 37° C. 6 µl of 30 mM ATP was added to the LPS-primed blood+compound, mixed thoroughly and incubated for a further 30 min at 37° C. 96 µL of ELISA assay buffer was added to each well and the plate centrifuged at 4° C. 1,200 rpm for 10 min. Supernatant was removed and assayed for IL-1β using the OptiEIA kit according to the manufacturer's protocol (Serum may be frozen at −20° C. prior to assay). IC$_{50s}$ were calculated using XLfit.

Example 15

In vivo Assay for Asthma and Lung Function

BALb/cJ mice are immunized with a standard immunization protocol. Briefly, mice (N=8/group) are immunized i.p. with ovalbumin (OVA; 10 µg) in alum on days 0 and 14. Mice are then challenged with aerosolized OVA (5%) on day 21 and 22. Animals receive vehicle (p.o.) or a compound of the invention (100 mg/kg p.o.) all starting on day 20.

Lung function is evaluated on day 23 using the Buxco system to measure PenH in response to an aerosol methacholine challenge. Mice are then euthanized and plasma samples collected at the end of the study.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula I:

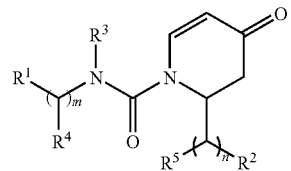

I or pharmaceutically acceptable salts thereof,
wherein:
m is 0 or 1;
n is 0 or 1;
R$^1$ is:
optionally substituted aryl;
optionally substituted heteroaryl; or
adamantyl;
R$^2$ is:
optionally substituted aryl;
optionally substituted heteroaryl;
C$_{3-6}$cycloalkyl;
C$_{1-6}$alkyl; or
C$_{3-6}$ branched alkyl; and
R$^3$, R$^4$ and R$^5$ each independently is:
hydrogen; or
C$_{1-6}$alkyl.

2. The compound of claim 1, wherein m is 0.
3. The compound of claim 2, wherein n is 0.
4. The compound of claim 3, wherein R$^3$, R$^4$ and R$^5$ are hydrogen.
5. The compound of claim 4, wherein R$^1$ is optionally substituted phenyl.
6. The compound of claim 5, wherein R$^1$ is phenyl substituted one, two, three or four times with a substituent or substituents each independently selected from: halo; C$_{1-6}$alkyl; C$_{1-6}$alkoxy; halo-C$_{1-6}$alkyl; halo-C$_{1-6}$alkoxy; C$_{1-6}$alkylsulfonyl; C$_{1-6}$alkylsulfanyl; C$_{1-6}$alkylsulfinyl; phenylsulfonyl wherein the phenyl portion is optionally substituted with C$_{1-6}$alkyl; nitrile; hydroxy; C$_{1-6}$alkylcarbonyl; aminocarbonyl; C$_{1-6}$alkoxycarbonyl; C$_{1-6}$alkoxycarbonyl-C$_{1-6}$alkoxy; hydroxycarbonyl; hydroxycarbonyl-C$_{1-6}$alkoxy; C$_{1-6}$alkylaminocarbonyl-C$_{1-6}$alkoxy; C$_{1-6}$alkoxy-C$_{1-6}$alkoxy; hydroxy-C$_{1-6}$alkoxy; C$_{1-6}$alkylamino-C$_{1-6}$alkoxy; C$_{1-6}$alkylsulfony-C$_{1-6}$alkoxy; hydroxy-C$_{1-6}$alkyl; C$_{3-6}$cycloalkyl-C$_{1-6}$alkoxy; amino; amino-C$_{1-6}$alkyl; C$_{1-6}$alkenyl; C$_{1-6}$alkynyl; morpholinyl; morpholinyl-C$_{1-6}$alkyl; piperazinyl; piperidinyloxy; aminocarbonyl-C$_{1-6}$alkoxy; C$_{1-6}$alkoxyamino-C$_{1-6}$alkyl; hydroxy-C$_{1-6}$alkylamino-C$_{1-6}$alkyl; C$_{1-6}$alkoxycarbonylamino-C$_{1-6}$alkyl; C$_{1-6}$alkylcarbonylamino-C$_{1-6}$alkyl; C$_{1-6}$alkylaminocarbonyl; C$_{1-6}$alkoxycarbonylC$_{1-6}$alkyl; C$_{1-6}$alkylaminocarbonyl-C$_{1-6}$alkyl; C$_{1-6}$alkylamino-C$_{1-6}$alkyl; hydroxycarbonyl-C$_{1-6}$alkyl; or nitro; or two adjacent substituents may form a $C_{1-2}$alkylenedioxy or halo-$C_{1-2}$alkylenedioxy.

7. The compound of claim 5, wherein $R^1$ is phenyl substituted one, two, three or four times with a substituent or substituents each independently selected from: fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; or two adjacent substituents may form methylenedioxy, ethylenedioxy or difluoromethylenedioxy.

8. The compound of claim 5, wherein $R^1$ is phenyl substituted one, two, three or four times with a substituent or substituents each independently selected from: halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; $C_{1-6}$alkoxy-$C_{1-6}$alkoxy; hydroxy-$C_{1-6}$alkoxy; $C_{1-6}$alkylsulfonyl-$C_{1-6}$alkoxy; hydroxy-$C_{1-6}$alkyl; hydroxy-$C_{1-6}$alkylamino; $C_{1-2}$alkylenedioxy; or $C_{3-6}$cycloalkyl-$C_{1-6}$alkoxy.

9. The compound of claim 5, wherein $R^1$ is phenyl substituted one, two, three or four times with a substituent or substituents each independently selected from: fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; hydroxypropoxy; methylenedioxy; or ethylenedioxy.

10. The compound of claim 5, wherein $R^1$ is phenyl optionally substituted one, two or three times with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

11. The compound of claim 5, wherein $R^2$ is optionally substituted phenyl.

12. The compound of claim 5, wherein $R^2$ is phenyl optionally substituted one, two or three times with a substituent or substituents each independently selected from: fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

13. The compound of claim 5, wherein $R^2$ is phenyl substituted once or twice with a substituent or substituents each independently selected from: fluoro; chloro; methyl; methoxy; or nitrile.

14. The compound of claim 5, wherein $R^2$ is phenyl substituted once or twice with fluoro.

15. The compound of claim 1, wherein said compound is of formula II:

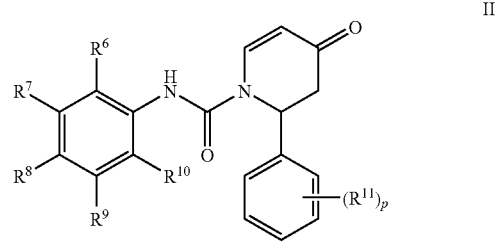

wherein:

p is from 0 to 3;

$R^6, R^7, R^8, R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; $C_{1-6}$alkylsulfanyl; $C_{1-6}$alkylsulfinyl; phenylsulfonyl wherein the phenyl portion is optionally substituted with $C_{1-6}$alkyl; nitrile; hydroxy; alkylcarbonyl; aminocarbonyl; alkoxycarbonyl; alkoxycarbonylalkoxy; hydroxycarbonyl; hydroxycarbonylalkoxy; alkylaminocarbonylalkoxy; alkoxyalkoxy; hydroxyalkoxy; alkylaminoalkoxy; alkylsulfonylalkoxy; hydroxyalkyl; $C_{3-6}$cycloalkyl-$C_{1-6}$alkoxy; amino; aminoalkyl; or nitro; or two adjacent substituents may form a $C_{1-2}$alkylenedioxy or halo-$C_{1-2}$alkylenedioxy; and each $R^{11}$ independently is: halo; $C_{1-6}$alkyl; $C_{1-6}$alkoxy; halo-$C_{1-6}$alkyl; halo-$C_{1-6}$alkoxy; $C_{1-6}$alkylsulfonyl; or nitrile.

16. The compound of claim 15, wherein at least two of $R^6$, $R^7$, $R^8$, $R^9$ and $R^{10}$ are not hydrogen.

17. The compound of claim 15, wherein $R^6, R^7, R^8, R^9$ and $R^{10}$ each independently is: hydrogen; fluoro; chloro; bromo; iodo; methyl; ethyl; methoxy; ethoxy; trifluoromethyl; difluoromethoxy; trifluoromethoxy; methanesulfonyl; methanesulfanyl; methanesulfinyl; toluenesulfonyl; nitrile; acetyl; aminocarbonyl; methoxycarbonyl; methoxycarbonylmethoxy; carboxy; hydroxycarbonylmethoxy; methylaminocarbonylmethoxy; methoxyethoxy; hydroxyethoxy; methylaminoethoxy; methanesulfonylpropyloxy; hydroxymethyl; hydroxyethyl; cyclopropylmethoxy; amino; or nitro; morpholinyl; N,N-dimethylaminocarbonylmethoxy; boc-piperazinyl; N-(2-methoxyethyl)-N-methylaminomethyl; N,N-dimethylaminomethyl; aminomethyl; boc-aminomethyl; methylcarbonylaminomethyl; N,N-di-(2-hydroxyethyl)-aminomethyl; morpholinylmethyl; 2-hydroxy-1-hydroxymethyl-ethyl; methylaminocarbonyl; piperidinyloxy; tert-butoxycarbonylmethyl; N,N-dimethylaminocarbonylmethyl; n-propyl; isopropyl; hydroxycarbonylmethyl; hydroxypropoxy; or two adjacent substituents may form methylenedioxy, ethylenedioxy or difluoromethylenedioxy.

18. The compound of claim 15, wherein $R^6, R^7, R^8, R^9$ and $R^{10}$ each independently is: hydrogen; halo; $C_{1-6}$alkyl; $C_{1-6}$alkoxy; halo-$C_{1-6}$alkyl; halo-$C_{1-6}$alkoxy; $C_{1-6}$alkylsulfonyl; nitrile; alkoxyalkoxy; hydroxyalkoxy; alkylsulfonylalkoxy; hydroxyalkyl; or $C_{3-6}$cycloalkyl-$C_{1-6}$alkoxy.

19. The compound of claim 15, wherein $R^6$, $R^7$, $R^8$, $R^9$ and $R^{10}$ each independently is: hydrogen; fluoro; chloro; bromo; iodo; methyl; ethyl; methoxy; ethoxy; trifluoromethyl; difluoromethoxy; methanesulfonyl; nitrile; methoxyethoxy; hydroxyethoxy; hydroxymethyl; hydroxyethyl; or cyclopropylmethoxy.

20. The compound of claim 15, wherein $R^6$, $R^7$, $R^8$, $R^9$ and $R^{10}$ each independently is: hydrogen; fluoro; chloro; bromo; methyl; ethyl; methoxy; ethoxy; trifluoromethyl; difluoromethoxy; nitrile; methoxyethoxy; hydroxyethoxy; hydroxymethyl; hydroxyethyl; or cyclopropylmethoxy.

21. The compound of claim 15, wherein $R^7$ and $R^{10}$ are hydrogen.

22. The compound of claim 21, wherein $R^6$ is: hydrogen; halo; or methyl.

23. The compound of claim 22, wherein $R^8$ is: hydrogen; methoxy; halo; methyl; or difluoromethoxy.

24. The compound of claim 15, wherein $R^9$ is: methoxy; hydrogen; 2-hydroxy-ethoxy; 2-methoxy-ethoxy; 1-hydroxy-ethyl; or cyclopropylmethyl.

25. The compound of claim 15, wherein p is 0, 1 or 2.

26. The compound of claim 25, wherein $R^{11}$ is halo.

27. The compound of claim 25, wherein $R^{11}$ is fluoro.

28. The compound of claim 15, wherein said compound is of formula III

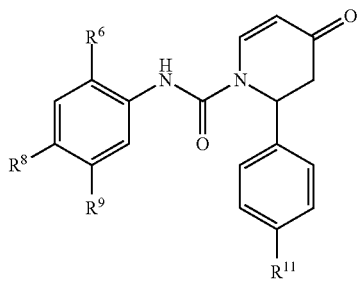

wherein $R^6$, $R^8$, $R^9$ and $R^{11}$ are as recited in claim 15.

29. A pharmaceutical composition comprising:
(a) a pharmaceutically acceptable carrier; and
(b) a compound of claim 1.

30. A method for treating arthritis, said method comprising administering to a subject in need thereof an effective amount of a compound of claim 1.

* * * * *